(12) United States Patent
Beus et al.

(10) Patent No.: US 9,314,472 B2
(45) Date of Patent: Apr. 19, 2016

(54) TREATMENT AND PREVENTION OF MASTITIS

(71) Applicants: Chad S. Beus, Spanish Fork, UT (US); Paul B. Savage, Mapleton, UT (US)

(72) Inventors: Chad S. Beus, Spanish Fork, UT (US); Paul B. Savage, Mapleton, UT (US)

(73) Assignee: BRIGHAM YOUNG UNIVERSITY, Provo, UT (US)

( * ) Notice: Subject to any disclaimer, the term of this patent is extended or adjusted under 35 U.S.C. 154(b) by 0 days.

(21) Appl. No.: 14/056,122

(22) Filed: Oct. 17, 2013

(65) Prior Publication Data

US 2014/0107090 A1    Apr. 17, 2014

Related U.S. Application Data

(60) Provisional application No. 61/715,277, filed on Oct. 17, 2012.

(51) Int. Cl.
*A61K 31/56* (2006.01)
*A61K 31/575* (2006.01)

(52) U.S. Cl.
CPC .................................. *A61K 31/575* (2013.01)

(58) Field of Classification Search
None
See application file for complete search history.

(56) References Cited

U.S. PATENT DOCUMENTS

| | | | |
|---|---|---|---|
| 4,661,341 A | 4/1987 | Benedict et al. |
| 4,842,593 A | 6/1989 | Jordan et al. |
| 4,865,855 A | 9/1989 | Hansen et al. |
| 4,972,848 A | 11/1990 | Di Domenico |
| 5,025,754 A | 6/1991 | Plyler |
| 5,286,479 A | 2/1994 | Garlich et al. |
| 5,310,545 A | 5/1994 | Eisen |
| 5,356,630 A | 10/1994 | Laurencin et al. |
| 5,380,839 A | 1/1995 | McCall et al. |
| 5,552,057 A | 9/1996 | Hughes et al. |
| 5,721,359 A | 2/1998 | Dunn et al. |
| 6,117,332 A | 9/2000 | Hatch et al. |

(Continued)

FOREIGN PATENT DOCUMENTS

| | | |
|---|---|---|
| CN | 101378761 | 3/2009 |
| CN | 102172356 | 9/2011 |

(Continued)

OTHER PUBLICATIONS

Steeneveld et al. Cow-specific treatment of clinical mastitis: an economic approach. J. Diary. Sci. 94: 174-188, 2011.*

(Continued)

*Primary Examiner* — Anna Pagonakis
(74) *Attorney, Agent, or Firm* — Workman Nydegger

(57) ABSTRACT

Treating and Preventing mastitis employing cationic steroidal antimicrobials (CSAs). Treating or preventing clinical mastitis in a mammal includes administering a cationic steroidal anti-microbial compound (CSA) formulation to the intramammary organ of a mammal (e.g., a dairy cow), such as by injection into the mammary organ (e.g., through the teat of the mammary organ), and/or topical application. The dairy cow can be lactating and have a somatic cell count (SCC) less than or equal to 500,000 cells/mL at the time of administering the CSA formulation. Alternatively, the dairy cow can be lactating and have a somatic cell count (SCC) greater than 500,000 cells/mL at the time of administering the CSA formulation. The dairy cow can be taken out of production during the administration of the CSA formulation for a period of time of about 3 days or less, 2 days or less, or 1 day or less.

22 Claims, 15 Drawing Sheets

(56) References Cited

U.S. PATENT DOCUMENTS

| | | | |
|---|---|---|---|
| 6,228,393 B1 | 5/2001 | DiCosmo et al. | |
| 6,350,738 B1 | 2/2002 | Savage et al. | |
| 6,486,148 B2 | 11/2002 | Savage et al. | |
| 6,562,318 B1 | 5/2003 | Filler | |
| 6,673,771 B1 | 1/2004 | Greene et al. | |
| 6,767,904 B2* | 7/2004 | Savage et al. | 514/182 |
| 6,803,066 B2 | 10/2004 | Traeder | |
| 6,872,303 B2 | 3/2005 | Knapp et al. | |
| 6,939,376 B2 | 9/2005 | Shulze et al. | |
| 7,282,214 B2 | 10/2007 | Wilcox et al. | |
| 7,381,439 B2 | 6/2008 | Hilgren et al. | |
| 7,598,234 B2 | 10/2009 | Savage et al. | |
| 7,659,061 B2 | 2/2010 | Hendl et al. | |
| 7,754,705 B2 | 7/2010 | Savage et al. | |
| 7,854,941 B2 | 12/2010 | Urban et al. | |
| 7,993,903 B2 | 8/2011 | Hayakawa et al. | |
| 8,211,879 B2 | 7/2012 | Savage et al. | |
| 8,529,681 B1 | 9/2013 | Hibbs et al. | |
| 8,623,416 B2 | 1/2014 | Zasloff et al. | |
| 8,691,252 B2 | 4/2014 | Savage | |
| 8,784,857 B2 | 7/2014 | Savage | |
| 2002/0091278 A1 | 7/2002 | Savage et al. | |
| 2003/0099717 A1 | 5/2003 | Cabrera | |
| 2004/0009227 A1 | 1/2004 | Yao | |
| 2004/0058974 A1 | 3/2004 | Courtney et al. | |
| 2004/0259445 A1 | 12/2004 | Hilfenhaus et al. | |
| 2005/0032765 A1 | 2/2005 | Savage et al. | |
| 2005/0075321 A1 | 4/2005 | Ahlem et al. | |
| 2005/0244468 A1 | 11/2005 | Huang et al. | |
| 2005/0267051 A1 | 12/2005 | Lee et al. | |
| 2006/0062742 A1 | 3/2006 | Davis et al. | |
| 2006/0269485 A1 | 11/2006 | Friedman et al. | |
| 2007/0106393 A1 | 5/2007 | Miles et al. | |
| 2007/0190066 A1 | 8/2007 | Savage et al. | |
| 2007/0190067 A1 | 8/2007 | Savage et al. | |
| 2007/0190558 A1 | 8/2007 | Savage et al. | |
| 2008/0174035 A1 | 7/2008 | Winterton | |
| 2008/0188819 A1 | 8/2008 | Kloke et al. | |
| 2009/0016973 A1 | 1/2009 | Ratcliff et al. | |
| 2009/0054295 A1 | 2/2009 | Vicari et al. | |
| 2009/0068122 A1 | 3/2009 | Pilch et al. | |
| 2009/0324517 A1 | 12/2009 | Kline | |
| 2010/0330086 A1 | 12/2010 | Savage et al. | |
| 2011/0091376 A1 | 4/2011 | Savage et al. | |
| 2011/0123624 A1 | 5/2011 | Zasloff | |
| 2012/0088733 A1 | 4/2012 | Kim et al. | |
| 2012/0107382 A1 | 5/2012 | Savage et al. | |
| 2013/0022651 A1 | 1/2013 | Savage | |
| 2013/0053507 A1 | 2/2013 | Savage | |
| 2013/0236619 A1 | 9/2013 | Savage | |
| 2013/0243823 A1 | 9/2013 | Genberg et al. | |
| 2013/0243840 A1 | 9/2013 | Savage et al. | |
| 2013/0243842 A1 | 9/2013 | Genberg et al. | |
| 2013/0245760 A1 | 9/2013 | Savage et al. | |
| 2013/0280312 A1 | 10/2013 | De Szalay | |
| 2013/0280391 A1 | 10/2013 | Savage | |
| 2014/0194401 A1 | 7/2014 | Genberg et al. | |
| 2014/0271761 A1 | 9/2014 | Savage et al. | |
| 2014/0274913 A1 | 9/2014 | Savage et al. | |
| 2014/0315873 A1 | 10/2014 | Beus et al. | |
| 2014/0369941 A1 | 12/2014 | Vazquez et al. | |
| 2015/0140063 A1 | 5/2015 | Savage | |
| 2015/0203527 A1 | 7/2015 | Savage | |
| 2015/0239928 A1 | 8/2015 | Savage | |
| 2015/0258121 A1 | 9/2015 | Darien et al. | |
| 2015/0258122 A1 | 9/2015 | Beus et al. | |
| 2015/0258123 A1 | 9/2015 | Savage et al. | |

FOREIGN PATENT DOCUMENTS

| | | |
|---|---|---|
| EP | 0341951 | 11/1989 |
| EP | 1208844 | 5/2002 |
| JP | 02014741 | 1/1990 |
| JP | 06153779 | 6/1994 |
| JP | 07501826 | 2/1995 |
| JP | 09248454 | 9/1997 |
| JP | 2002505292 | 2/2002 |
| JP | 2002255771 | 9/2002 |
| JP | 2002534532 | 10/2002 |
| JP | 2002538093 | 11/2002 |
| JP | 2004506645 | 3/2004 |
| JP | 2010533051 | 10/2010 |
| JP | 2010538074 | 12/2010 |
| JP | 2011527702 | 11/2011 |
| JP | 2014500741 | 1/2014 |
| WO | WO 9524415 | 9/1995 |
| WO | WO 9944616 | 9/1999 |
| WO | WO 0042058 | 7/2000 |
| WO | WO 0214342 | 2/2002 |
| WO | WO02067979 | 9/2002 |
| WO | WO 03015757 | 2/2003 |
| WO | WO 03090799 | 11/2003 |
| WO | WO2004082588 | 9/2004 |
| WO | WO 2004112852 | 12/2004 |
| WO | WO 2007089903 | 8/2007 |
| WO | WO 2007089906 | 8/2007 |
| WO | WO 2007089907 | 8/2007 |
| WO | WO 2007134176 | 11/2007 |
| WO | WO 2008038965 | 4/2008 |
| WO | WO 2009079066 | 6/2009 |
| WO | WO2010006192 | 1/2010 |
| WO | WO 2010036427 | 4/2010 |
| WO | WO 2010062562 | 6/2010 |
| WO | WO2011066260 | 6/2011 |
| WO | WO 2011109704 | 9/2011 |
| WO | WO 2012061651 | 5/2012 |
| WO | WO 2013029055 | 2/2013 |
| WO | WO 2013029059 | 2/2013 |
| WO | WO2013/109236 | 7/2013 |
| WO | WO 2013109236 | 7/2013 |

OTHER PUBLICATIONS

"Structure-Activity Relationship and Drug Design." Remington's Pharmaceutical Sciences (Sixteenth Edition). Mack Publishing, 1980, pp. 420-425.*

Berge et al. "Pharmaceutical Salts." Journal of Pharmaceutical Sciences, 66(1): 1977, 1-19.*

Bridot et al., "Hybrid Gadolinium Oxide Nanoparticles: Multimodal Contrast Agents for in Vivo Imaging", Journal of American Chemical Society, vol. 129, No. 16, pp. 5076-5084, Mar. 31, 2007.

Britton et al, "Imaging bacterial infection with 99mTc-ciprofloxacin (Infection)", Journal of Clinical Pathology, vol. 55, pp. 817-823, Apr. 6, 2015.

Suzuki et al., "Molecular Genetics of Plant Sterol Backbone Synthesis", 2007; Lipids; 42: 47-54.

Van Den Bogaard et al., "Antibiotic Usage in Animals: Impact on Bacterial Resistance and Public Health"; 1999; Drugs; 58 (4): 589-607.

U.S. Appl. No. 13/615,244, filed Sep. 13, 2012, Office Action dated Jan. 16, 2015.

U.S. Appl. No. 14/257,776, filed Apr. 21, 2014, Restriction Requirement dated Jan. 22, 2015.

U.S. Appl. No. 14/364,283, filed Jul. 29, 2014, Office Action dated Feb. 11, 2015.

U.S. Appl. No. 14/339,342, filed Jul. 23, 2014, Office Action dated Mar. 5, 2015.

U.S. Appl. No. 13/554,930, filed Jul. 20, 2012, Final Office Action dated Mar. 16, 2015.

U.S. Appl. No. 13/783,007, filed Mar. 1, 2013, Restriction Requirement dated Mar. 31, 2015.

U.S. Appl. No. 13/000,010, filed Dec. 17, 2010, Office Action dated Apr. 14, 2015.

U.S. Appl. No. 14/257,776, filed Apr. 21, 2014, Office Action dated Apr. 16, 2015.

U.S. Appl. No. 13/783,007, filed Mar. 1, 2013, Savage, Paul B.

U.S. Appl. No. 14/288,126, filed May 27, 2014, Savage, et al.

U.S. Appl. No. 14/339,342, filed Jul. 23, 2014, Vazquez, et al.

U.S. Appl. No. 14/341,304, filed Jul. 25, 2014, Savage, et al.

U.S. Appl. No. 14/364,283, filed Jul. 29, 2014, Vazquez, et al.

(56) References Cited

OTHER PUBLICATIONS

U.S. Appl. No. 14/515,858, filed Oct. 16, 2014, Savage, et al.
U.S. Appl. No. 14/398,094, filed Oct. 30, 2014, Savage, et al.
P. B. Savage, et al., "Thin Films Containing Ceragenins Prevent Biofilm Formation on Endotracheal Tubes", 9th International Federation of Infection Control Congress, Oct. 14, 2008, pp. 1-1.
Xin-Zhong Lai, et al., "Ceragenins: Cholic Acid-Based Mimics of Antimicrobial peptides", Account of Chemical Research vol. 41, No. 10, Oct. 21, 2008, pp. 1233-1240.
K.D. Sinclair, et al., "Development of a broad spectrum polymer-released antimicrobial coating for the prevention of resistant strain bacterial infections", Journal of Biomedical Materials Research Part A, vol. 100A, No. 10, May 24, 2012, pp. 2732-2738.
Emily L. Perry et al., "Assessing peri-implant tissue infection prevention in a percutaneous model", Journal of Biomedical Materials Research Part B: Applied Biomaterials, vol. 02B, Nov. 19, 2009, pp. 397-408.
Savage, et al., "Antibacterial Activities of Thin Films Containing Ceragenins", Microbial Surfaces: Structure, Interactions and Reactivity, ACS, May 30, 2008, pp. 65-78.
P. B. Savage, et al., "Use of a Ceragenin-Based Coating to Prevent Bacterial Colonization of Urinary Catheters", 48th Annual Interscience Conference on Anti-Microbial Agents & Chemotherapy, Oct. 26, 2008, pp. 1-1.
Michael D. Howell, et al., "Ceragenins: A 1-18, class of Antiviral Compounds to Treat Orthopox Infections", Journal of Investigative Dermatology, vol. 129, No. 11, Jun. 11, 2009, pp. 2688-2675.
K. Leszczynska et al., "Potential of ceragenin CSA-13 and its mixture with pluronic F-127 as treatment of topical bacterial infections", Journal of Applied Microbiology, vol. 110, No. 1, Oct. 21, 2010, pp. 229-238.
Isogai E et al: "Ceragenin CSA-13 exhibits antimicrobial activity against cariogenic and periodontopathic bacteria", Oral Microbiology and Immunology, vol. 24, No. 2, Apr. 2009, pp. 170-172.
Van Bambeke et al: "The bacterial envelope as a target for novel anti-MRSA antibiotics", Trends in Pharmacological Sciences, Elsevier, Haywarth, GB, vol. 29, No. 3, Feb. 11, 2008, pp. 124-134.
Qunying Guan et al: "Preparation and Characterization of Cholic Acid-Derived Antimicrobial Agents with Controlled Stabilities", Organic Letters, American Chemical Society, US, vol. 2, No. 18, Sep. 7, 2000, pp. 2837-2840.
Alhanout K et al: "Squalamine as an example of a new potent antimicrobial agents class: a critical review.", Current Medicinal Chemistry 2010, vol. 17, No. 32, 2010, pp. 3909-3917.
International Search Report for PCT Application No. PCT/US2012/047750, Mailed Date: Oct. 5, 2012, Filed Date: Sep. 27, 2012, 3 pages.
Bucki et al., "Salivary mucins inhibit antibacterial activity of the cathelicidin-derived LL-37 peptide but not the cationic steroid CSA-13", Journal of Antimicrobial Chemotherapy (2008) 62: 329-335, 7 pages.
Pitten F-A, et al., "Efficacy of cetylpyridinium chloride used as oropharyngeal antiseptic" Arzenimittel Forschung. Rug Research, ECV Editio Cantor Verlag, Aulendorf, DE, vol. 51, No. 7, Jan. 1, 2001, pp. 588-595.
Paul B. Savage, et al: "Antibacterial Properties of cationic steroid antibiotics", FEMS Microbiology Letters, vol. 217, Nov. 2002, pp. 1-7.
Lai, et al., "Controlled Released of a Bactericidal Ceragenin-Polymer Conjugate", Sep. 227, 2006, p. 1, 46th Annual Interscience Conference on Antimicrobial Agents and Chemotherapy.
Li Chunhong, et al., "Antimicrobial Activities of Amine- and Guanidine-functionalized Cholic Acid Derivatives", Antimicrobial Agents and Chemotherapy, American Society for Microbiology, Washington DC, US, vol. 43, No. 6, Jun. 1999, pp. 1347-1349.
Ding, et al., "Origins of cell selectivity of cationic steroid antibiotics", Journal of American Chemical Society, Oct. 2004, pp. 13642-13648.
Melinda Yin, et al., "Antiangiogenic Treatment Delays Chondrocyte Maturation and Cone Formation During Lim Skeltogenesis", Journal of Vone and Mineral Research, American Society for Bone and Mineral Research, New York, NY, US, vol. 17, No. 1, Jan. 1, 2002.
International Search Report for PCT Application No. PCT/US2009/047485 dated Feb. 17, 2010.
International Search Report for PCT Application No. PCT/US2013/038090, Mailed Date: Jul. 24, 2013.
Qunying Guan et al: "Supporting Information: Preparation and Characterization of Cholic Acid-Derived Antimicrobial Agents with Controlled Stabilities", Organic Letters, Aug. 17, 2000, pp. 1-7, XP55017313, Retrieved from the Internet: URL:http://pubs.acs.org/doi/suppl/10.1021/ol0062704/suppl file/ol0062704 sl.pdf.
Atiq-Ur-Rehman Li C et al: "Preparation of Amino Acid-Appended Cholic Acid Derivatives as Sensitizers of Gram-Negative Bacteria", Tetrahedron Letters, Elsevier, Amsterdam, NL, vol. 40, No. 10, Mar. 5, 1999, pp. 1865-1868, XP004155984, ISSN: 0040-4039, DOI: 10.1016/S0040-4039(99)00075-1.
Chin et al, "Antimicrobial Activities of Ceragenins against Clinicial Isolates of Resistant *Staphylococcus aureas*.", Antimcirobial Agents and Chemotherapy, vol. 51, No. 4, Apr. 2007, p. 1268-1273.
Fritsch et al, "In Vitro Activity of Nine Developmental Cationic Steroid Compounds (Ceragenins) against Clnical Isolates of Clostridium difficile", The 46th Interscience Conference on Antimicrobial Agents and Chemotherapy, Sep. 27, 2006, pp. 1-1.
International Search Report for PCT Application No. PCT/US2011/059225 dated Jan. 31, 2012.
International Search Report for PCT Application No. PCT/US2012/055248 dated Feb. 14, 2013.
International Search Report for PCT Application No. PCT/US2012/055244 dated Dec. 5, 2012.
U.S. Appl. No. 13/288,902, filed Jun. 21, 2012, Restriction Requirement.
U.S. Appl. No. 13/288,902, filed Nov. 7, 2012, Office Action.
U.S. Appl. No. 13/000,010, filed Dec. 4, 2012, Restriction Requirement.
U.S. Appl. No. 13/288,892, filed Dec. 10, 2012, Restriction Requirement.
U.S. Appl. No. 13/288,892, filed May 9, 2013, Office Action.
U.S. Appl. No. 13/288,902, filed Aug. 9, 2013, Notice of Allowance.
U.S. Appl. No. 13/288,892, filed Nov. 29, 2013, Notice of Allowance.
U.S. Appl. No. 13/594,608, filed Jan. 30, 2014, Office Action.
U.S. Appl. No. 13/615,324, filed Jan. 30, 2014, Office Action.
U.S. Appl. No. 13/554,957, filed Apr. 1, 2014, Office Action.
U.S. Appl. No. 13/594,612, filed May 15, 2014, Office Action.
U.S. Appl. No. 13/554,930, filed Jul. 11, 2014, Office Action.
U.S. Appl. No. 13/554,957, filed Aug. 1, 2014, Notice of Allowance.
U.S. Appl. No. 13/783,131, filed Oct. 23, 2014, Office Action.
U.S. Appl. No. 14/694,028, filed Apr. 23, 2015, Beus et al.
U.S. Appl. No. 14/842,582, filed Sep. 1, 2015, Genberg et al.
U.S. Appl. No. 14/848,819, filed Sep. 9, 2015, Genberg et al.
U.S. Appl. No. 14/873,013, filed Oct. 1, 2015, Savage et al.
U.S. Appl. No. 14/926,738, filed Oct. 29, 2015, Vazquez et al.
U.S. Appl. No. 14/750,928, filed Jun. 25, 2015, Genberg et al.
U.S. Appl. No. 14/875,953, filed Oct. 6, 2015, Savage.
U.S. Appl. No. 14/830,356, filed Aug. 19, 2015, Savage.
U.S. Appl. No. 14/866,213, filed Sep. 25, 2015, Savage.
International Search Report for PCT Application No. PCT/US2013/065510, dated Apr. 30, 2015.
International Search Report for PCT Application No. PCT/US2014/034986 dated Aug. 28, 2014.
International Search Report for PCT Application No. PCT/US2015/020166 dated Sep. 2, 2015.
International Search Report for PCT Application No. PCT/US2015/038029 dated Sep. 29, 2015.
Shi et al., "Multi-center randomized double-blind clinicial trail on efficacy of a mouthwash containing 0.1% cetylpiridinium chloride on gingivitis and plaque and its safety", Chinese Journal of Evidence-Based Medicine (Sep. 2003, vol. 3, No. 3, pp. 171-177).

\* cited by examiner

CSA-52

CSA-56

CSA-61

CSA-141

CSA-142

CSA-118

CSA-119

CSA-120

CSA-121

CSA-121a

CSA-122

CSA-123

CSA-124

CSA-130

CSA-131

CSA-132

TREATMENT AND PREVENTION OF MASTITIS

CROSS-REFERENCE TO RELATED APPLICATIONS

This application claims the benefit of U.S. Provisional Application No. 61/715,277, filed Oct. 17, 2012, the disclosure of which is incorporated herein in its entirety.

BACKGROUND OF THE INVENTION

1. The Field of the Invention

The present invention relates to compositions and methods for treating mastitis using cationic steroidal antimicrobial (CSA) compounds.

2. The Relevant Technology

The treatment and prevention of mastitis in dairy cows continues to be of primary importance to those engaged in the dairy farming industry. The combined costs of mastitis to the U.S. dairy farming industry have been estimated at over two billion dollars annually.

Mastitis is caused by infections of the mammary, or milk-producing, glands by a broad spectrum of pathogenic microorganisms. In particular, when the milk-producing glands and surrounding tissues in the udder become infected, the tissues become inflamed with cellular infiltrates and associated toxic substances. The cellular infiltrates and associated toxins, along with the infecting organisms themselves, can cause a dramatic reduction in the quality of milk produced by the animal. The infiltrates, toxins, and microorganisms can also affect the quantity of milk produced by the animal, possibly even resulting in the stoppage of production. Occasionally, the infection can spread systemically to other organ and tissue sites via the blood or lymphatic systems. The spreading infection can, in extreme cases, seriously debilitate or kill the infected animal.

Given the importance of the mastitis problem to dairy farmers, several methods have been proposed to combat this problem. One method frequently used to combat the problem has been to separate out the infected animals from the herd, and then to treat the infected animals with antibiotics. Antibiotics can be administered either directly (via an injection) or indirectly (via feed). However, the secondary problem of antibiotic residues in the treated animals and their milk products has come under increased scrutiny from federal and state regulatory agencies. Additionally, public outcry over the use of antibiotics and the presence of antibiotics residues in meat and milk products has severely limited the market for such products.

Thus there is a need to find an alternative to, and decrease the dependence on, antibiotics in managing udder health of lactating mammals such as dairy cows.

SUMMARY

Disclosed herein are methods for treating and preventing mastitis using cationic steroidal antimicrobials (CSAs). According to one embodiment, method for treating or preventing clinical mastitis in a mammal includes administering a cationic steroidal anti-microbial compound (CSA) formulation to the intra-mammary organ of a mammal. For example, the CSA formulation can be administered by injection into the mammary organ (e.g., through the teat of the mammary organ). A non-limiting example of a mammal that can benefit from the treatments disclosed herein is a dairy cow.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings, in which.

DETAILED DESCRIPTION

Figure 1A:
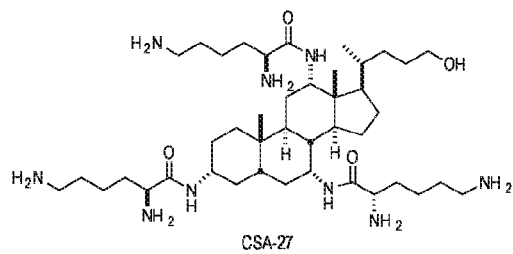
FIG. 1A illustrates exemplary hydrolysable cationic steroidal anti-microbial ("CSA") compounds.
Figure 1A:
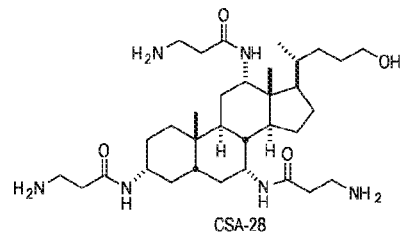
Figure 1A:
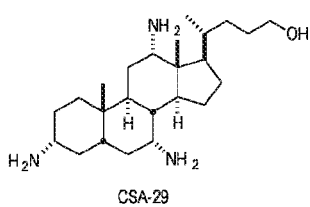
Figure 1A:
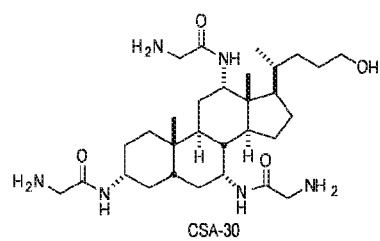
Figure 1A:
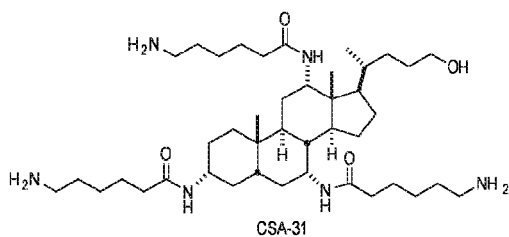
Figure 1A:
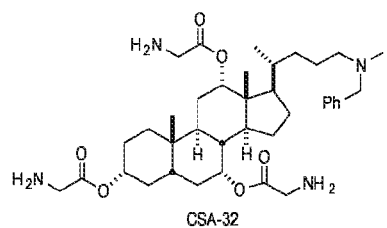
Figure 1A:
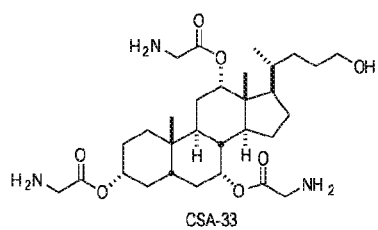
Figure 1A:
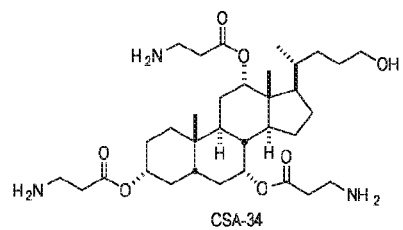
Figure 1A:
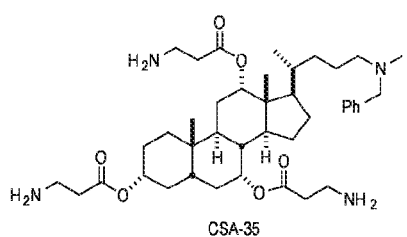
Figure 1A:
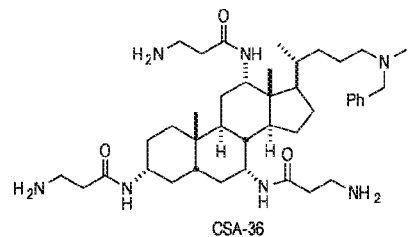
Figure 1A:
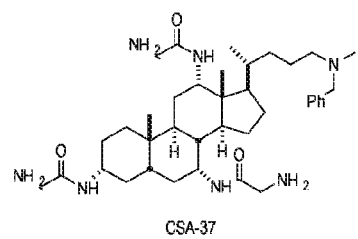
Figure 1A:
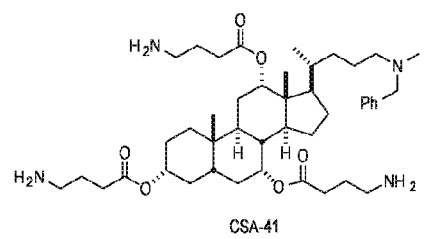
Figure 1A:
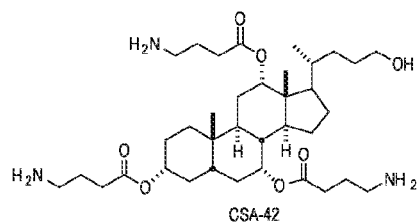
Figure 1A:
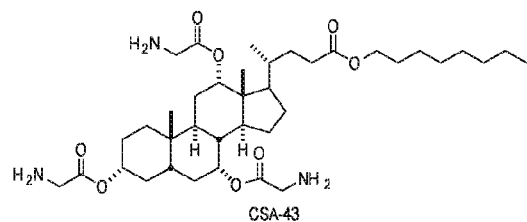
Figure 1A:
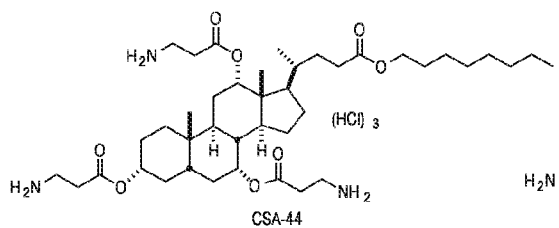
Figure 1A:
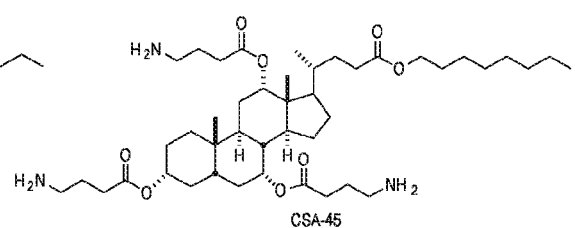
Figure 1A:
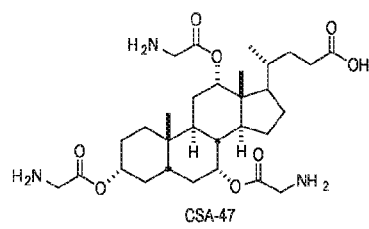
Figure 1A:
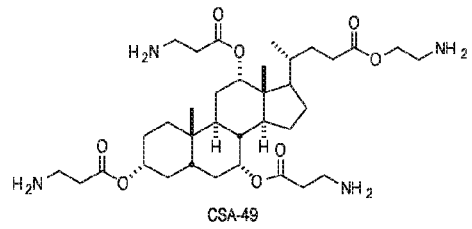
Figure 1A:
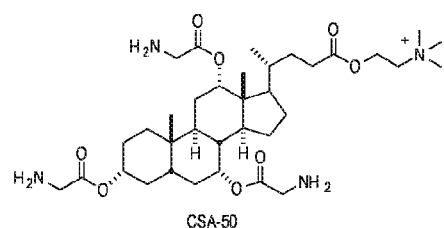
Figure 1A:
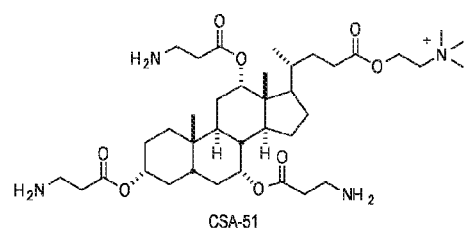
Figure 1A:
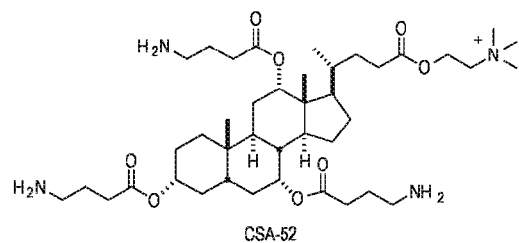
Figure 1A:
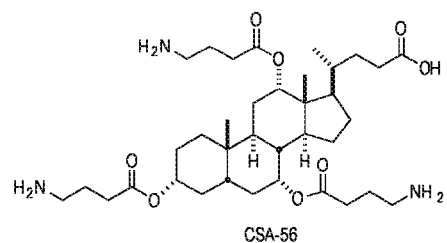
Figure 1A:
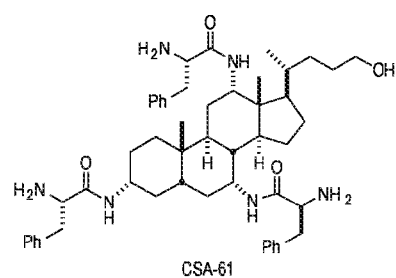
Figure 1A:
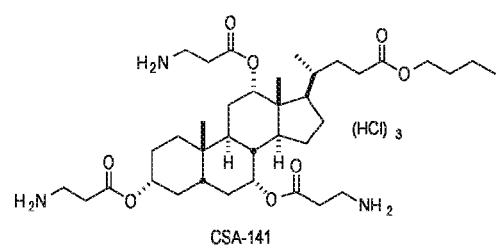
Figure 1A:
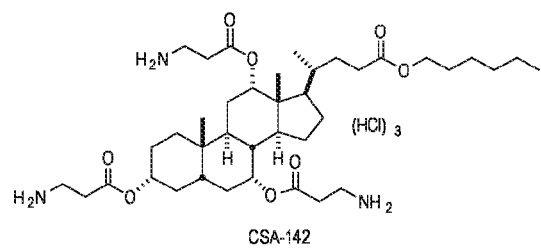

Disclosed herein are compositions and methods for treating mastitis using cationic steroidal antimicrobials (CSAs). Ceragenin compounds, also referred to herein as cationic steroidal anti-microbial compounds (CSAs), are synthetically produced small molecule chemical compounds that include a sterol backbone having various charged groups (e.g., amine and cationic groups) attached to the backbone. The backbone can be used to orient the amine or guanidine groups on one face, or plane, of the sterol backbone. For example, a scheme showing a compound having primary amino groups on one face, or plane, of a backbone is shown below in Scheme I:

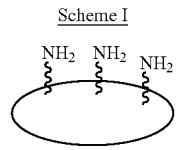

Scheme I

Ceragenins are cationic and amphiphilic, based upon the functional groups attached to the backbone. They are facially amphiphilic with a hydrophobic face and a polycationic face. Without wishing to be bound to any particular theory, the anti-microbial ceragenin compounds described herein act as anti-microbial agents (e.g., anti-bacterials, anti-fungals, and anti-virals). It is believed, for example, that the anti-microbial ceragenin compounds described herein act as anti-bacterials by binding to the cellular membrane of bacteria and other microbes and inserting into the cell membrane forming a pore that allows the leakage of ions and cytoplasmic materials that are critical to the microbe's survival and leading to the death of the affected microbe. In addition, the anti-microbial ceragenin compound described herein may also act to sensitize bacteria to other antibiotics. For example, at concentrations of the anti-microbial ceragenin compounds below the corresponding minimum bacteriostatic concentration, the ceragenins cause bacteria to become more susceptible to other antibiotics by increasing the permeability of the membrane of the bacteria. The charged groups are responsible for disrupting the bacterial cellular membrane and impart the anti-microbial properties.

The present invention relates to treating and/or preventing mastitis by administering a CSA formulation to the mammary organ of a mammal. In some embodiments the CSA formulation is administered locally by injection or topical application of a CSA. The injection can be a liquid injection administered through the teat directly into the mammary organ. Alternatively, the administration may be a teat dip that is topically applied to the teat to prevent infections.

For purposes of this invention, clinical mastitis is a mammary infection with a somatic cell count (SCC) greater than or equal to 500,000 cells/ml and subclinical mastitis is an infection with a SCC less than or equal to 500,000 cells/ml.

The CSA compounds administered to treat mastitis as described herein have been found to be surprisingly and unexpectedly effective at treating mastitis as compared to antibiotics and antimicrobial peptides. CSAs have surprisingly been found to be effective against a broad spectrum of microbes when administered intra-mammary for the treatment of mastitis. CSAs were found to be highly successful at treating and/or preventing mastitis caused by gram positive bacteria, gram negative bacteria, and fungi. For example, CSAs were found to kill *Staphylococci, E. coli*, and *Prototheca*.

The broad-spectrum efficacy of CSAs against mastitis is particularly important for treating dairy cows. Mastitis is known to occur from a broad spectrum of microbes and dairy farmers often treat the mastitis without knowing what type of microbe is causing the condition. Because the CSA compounds are effective against a broad spectrum of microbes, the CSA compounds can treat or prevent mastitis with fewer compounds or treatment attempts. This is particularly important for prevention measures. Avoiding the trial and error treatments that typically occur in treating mastitis allows the treatments to be carried out more quickly and reduces or eliminates the need to separate the animal from production, thereby resulting in substantial savings of lost milk production.

Because the CSA treatments of the present invention do not require the use of an antibiotic, the CSA treatments can be performed without reducing the quality of the milk produced. The CSA treatments can be performed on non-lactating animals (i.e., dry animals) or animals in milk production that have a subclinical somatic cell count (SCC).

Another unexpected result of the use of CSAs to treat mastitis is the avoidance of inflammation of the mammary organ. Studies indicate that CSAs can be administered in amounts sufficient to treat and/or prevent mastitis without causing inflammation or toxic side effects. Inflammation is a known problem with some types of mastitis treatments such as nisin. Thus CSA have exhibited superior properties compared to known compounds by having broad spectrum efficacy without causing inflammation or contaminating the milk.

DEFINITIONS

Unless otherwise defined, all technical and scientific terms used herein have the same meaning as commonly understood by one of ordinary skill in the art to which these embodiments belong. The terminology used in the description herein is for describing particular embodiments only and is not intended to be limiting of the embodiments. As used in the specification and the appended claims, the singular forms "a," "an," and "the" are intended to include the plural forms as well, unless the context clearly indicates otherwise. All publications, patent applications, patents, and other references mentioned herein are incorporated by reference in their entirety.

Terms and phrases used in this application, and variations thereof, especially in the appended claims, unless otherwise expressly stated, should be construed as open ended as opposed to limiting. As examples of the foregoing, the term "including" should be read to mean "including, without limitation," "including but not limited to," or the like; the term "comprising" as used herein is synonymous with "including," "containing," or "characterized by," and is inclusive or open-ended and does not exclude additional, unrecited elements or method steps; the term "having" should be interpreted as "having at least"; the term "includes" should be interpreted as "includes but is not limited to"; the term "example" is used to provide exemplary instances of the item in discussion, not an exhaustive or limiting list thereof; and use of terms like "preferably," "preferred," "desired," or "desirable," and words of similar meaning should not be understood as implying that certain features are critical, essential, or even important to the structure or function of the invention, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should be read as "and/or" unless expressly stated otherwise.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium.

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present embodiments. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the embodiments are approximations, the numerical values set forth in the specific examples are reported as precisely as possible. Any numerical value, however, inherently contains certain errors necessarily resulting from the standard deviation found in their respective testing measurements. Every numerical range given throughout this specification and claims will include every narrower numerical range that falls within such broader numerical range, as if such narrower numerical ranges were all expressly written herein. Where a range of values is provided, it is understood that the upper and lower limit, and each intervening value between the upper and lower limit of the range is encompassed within the embodiments.

As used herein, any "R" group(s) such as, without limitation, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ represent substituents that can be attached to the indicated atom. Unless otherwise specified, an R group may be substituted or unsubstituted.

The term "ring" as used herein can be heterocyclic or carbocyclic. The term "saturated" used herein refers to a fused ring having each atom in the fused ring either hydrogenated or substituted such that the valency of each atom is filled. The term "unsaturated" used herein refers to a fused ring where the valency of each atom of the fused ring may not be filled with hydrogen or other substituents. For example, adjacent carbon atoms in the fused ring can be doubly bound to each other. Unsaturation can also include deleting at least one of the following pairs and completing the valence of the ring carbon atoms at these deleted positions with a double bond; such as $R_5$ and $R_9$; $R_8$ and $R_{10}$; and $R_{13}$ and $R_{14}$.

Whenever a group is described as being "substituted" that group may be substituted with one, two, three or more of the indicated substituents, which may be the same or different, each replacing a hydrogen atom. If no substituents are indicated, it is meant that the indicated "substituted" group may be substituted with one or more group(s) individually and independently selected from alkyl, alkenyl, alkynyl, cycloalkyl, cycloalkenyl, cycloalkynyl, acylalkyl, alkoxyalkyl, aminoalkyl, amino acid, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen (e.g., F, Cl, Br, and I), thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, oxo, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group, $R^aO(CH_2)_mO—$, $R^b(CH_2)_nO—$, $R^cC(O)O(CH_2)_pO—$, and protected derivatives thereof. The substituent may be attached to the group at more than one attachment point. For example, an aryl group may be substituted with a heteroaryl group at two attachment points to form a fused multicyclic aromatic ring system. Biphenyl and naphthalene are two examples of an aryl group that is substituted with a second aryl group.

As used herein, "$C_a$" or "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, cycloalkynyl, aryl, heteroaryl or heteroalicyclyl group. That is, the alkyl, alkenyl, alkynyl, ring of the cycloalkyl, ring of the cycloalkenyl, ring of the cycloalkynyl, ring of the aryl, ring of the heteroaryl or ring of the heteroalicyclyl can contain from "a" to "b", inclusive, carbon atoms. Thus, for example, a "$C_1$ to $C_4$ alkyl" group refers to all alkyl groups having from 1 to 4 carbons, that is, $CH_3—$, $CH_3CH_2—$, $CH_3CH_2CH_2—$, $(CH_3)_2CH—$, $CH_3CH_2CH_2CH_2—$, $CH_3CH_2CH(CH_3)—$ and $(CH_3)_3C—$. If no "a" and "b" are designated with regard to an alkyl, alkenyl, alkynyl, cycloalkyl cycloalkenyl, cycloalkynyl, aryl, heteroaryl or heteroalicyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 25 carbon atoms (whenever it appears herein, a numerical range such as "1 to 25" refers to each integer in the given range; e.g., "1 to 25 carbon atoms" means that the alkyl group may consist of 1 carbon atom, 2 carbon atoms, 3 carbon atoms, etc., up to and including 25 carbon atoms, although the present definition also covers the occurrence of the term "alkyl" where no numerical range is designated). The alkyl group may also be a medium size alkyl having 1 to 15 carbon atoms. The alkyl group could also be a lower alkyl having 1 to 6 carbon atoms. The alkyl group of the compounds may be designated as "$C_4$" or "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isohutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. The alkenyl group may have 2 to 25 carbon atoms (whenever it appears herein, a numerical range such as "2 to 25" refers to each integer in the given range; e.g., "2 to 25 carbon atoms" means that the alkenyl group may consist of 2 carbon atom, 3 carbon atoms, 4 carbon atoms, etc., up to and including 25 carbon atoms, although the present definition also covers the occurrence of the term "alkenyl" where no numerical range is designated). The alkenyl group may also be a medium size alkenyl having 2 to 15 carbon atoms. The alkenyl group could also be a lower alkenyl having 1 to 6 carbon atoms. The alkenyl group of the compounds may be designated as "$C_4$" or "$C_2$-$C_4$ alkyl" or similar designations. An alkenyl group may be unsubstituted or substituted.

As used herein, "alkynyl" refers to an alkyl group that contains in the straight or branched hydrocarbon chain one or more triple bonds. The alkynyl group may have 2 to 25 carbon atoms (whenever it appears herein, a numerical range such as "2 to 25" refers to each integer in the given range; e.g., "2 to 25 carbon atoms" means that the alkynyl group may consist of 2 carbon atom, 3 carbon atoms, 4 carbon atoms, etc., up to and including 25 carbon atoms, although the present definition also covers the occurrence of the term "alkynyl" where no numerical range is designated). The alkynyl group may also be a medium size alkynyl having 2 to 15 carbon atoms. The alkynyl group could also be a lower alkynyl having 2 to 6 carbon atoms. The alkynyl group of the compounds may be designated as "$C_4$" or "$C_2$-$C_4$ alkyl" or similar designations. An alkynyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group (although the definition of $C_6$-$C_{10}$ aryl covers the occurrence of "aryl" when no numerical range is designated). Examples of aryl groups include, but are not limited to, benzene, naphthalene and azulene. An aryl group may be substituted or unsubstituted.

As used herein, "aralkyl" and "aryl(alkyl)" refer to an aryl group connected, as a substituent, via a lower alkylene group. The aralkyl group may have 6 to 20 carbon atoms (whenever it appears herein, a numerical range such as "6 to 20" refers to each integer in the given range; e.g., "6 to 20 carbon atoms" means that the aralkyl group may consist of 6 carbon atom, 7 carbon atoms, 8 carbon atoms, etc., up to and including 20 carbon atoms, although the present definition also covers the occurrence of the term "aralkyl" where no numerical range is designated). The lower alkylene and aryl group of an aralkyl may be substituted or unsubstituted. Examples include but are not limited to benzyl, 2-phenylalkyl, 3-phenylalkyl, and naphthylalkyl.

"Lower alkylene groups" refer to a $C_1$-$C_{25}$ straight-chained alkyl tethering groups, such as —$CH_2$— tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—), and butylene (—$CH_2CH_2CH_2CH_2$—). A lower alkylene group can be substituted by replacing one or more hydrogen of the lower alkylene group with a substituent(s) listed under the definition of "substituted."

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multicyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

As used herein, "cycloalkynyl" refers to a mono- or multicyclic hydrocarbon ring system that contains one or more triple bonds in at least one ring. If there is more than one triple bond, the triple bonds cannot form a fully delocalized pi-electron system throughout all the rings. When composed of two or more rings, the rings may be joined together in a fused fashion. A cycloalkynyl group may be unsubstituted or substituted.

As used herein, "alkoxy" or "alkyloxy" refers to the formula —OR wherein R is an alkyl, an alkenyl, an alkynyl, a cycloalkyl, a cycloalkenyl or a cycloalkynyl as defined above. A non-limiting list of alkoxys are methoxy, ethoxy, n-propoxy, 1-methylethoxy (isopropoxy), n-butoxy, iso-butoxy, sec-butoxy and tert-butoxy. An alkoxy may be substituted or unsubstituted.

As used herein, "acyl" refers to a hydrogen, alkyl, alkenyl, alkynyl, aryl, or heteroaryl connected, as substituents, via a carbonyl group. Examples include formyl, acetyl, propanoyl, benzoyl, and acryl. An acyl may be substituted or unsubstituted.

As used herein, "alkoxyalkyl" or "alkyloxyalkyl" refers to an alkoxy group connected, as a substituent, via a lower alkylene group. Examples include alkyl-O-alkyl- and alkoxyalkyl- with the terms alkyl and alkoxy defined herein.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

The term "amino" as used herein refers to a —$NH_2$ group.
As used herein, the term "hydroxy" refers to a —OH group.
A "cyano" group refers to a "CN" group.
A "carbonyl" or an "oxo" group refers to a C=O group.
The term "azido" as used herein refers to a —$N_3$ group.
As used herein, "aminoalkyl" refers to an amino group connected, as a substituent, via a lower alkylene group. Examples include $H_2$N-alkyl- with the term alkyl defined herein.

As used herein, "alkylcarboxyalkyl" refers to an alkyl group connected, as a substituent, to a carboxy group that is connected, as a substituent, to an alkyl group. Examples include alkyl-C(=O)O-alkyl- and alkyl-O—C(=O)-alkyl- with the term alkyl as defined herein.

As used herein, "C-carboxyalkyl" refers to a carboxy group connected, as a substituent, to an alkyl group. Examples include HO—(C=O)-alkyl, with the term alkyl as defined herein.

As used herein, "alkylaminoalkyl" refers to an alkyl group connected, as a substituent, to an amino group that is connected, as a substituent, to an alkyl group. Examples include alkyl-NH-alkyl-, with the term alkyl as defined herein.

As used herein, "dialkylaminoalkyl" or "di(alkyl)aminoalkyl" refers to two alkyl groups connected, each as a substituent, to an amino group that is connected, as a substituent, to an alkyl group. Examples include with the term alkyl as defined herein.

As used herein, "alkylaminoalkylamino" refers to an alkyl group connected, as a substituent, to an amino group that is connected, as a substituent, to an alkyl group that is connected, as a substituent, to an amino group. Examples include alkyl-NH-alkyl-NH—, with the term alkyl as defined herein.

As used herein, "alkylaminoalkylaminoalkylamino" refers to an alkyl group connected, as a substituent, to an amino group that is connected, as a substituent, to an alkyl group that is connected, as a substituent, to an amino group that is connected, as a substituent, to an alkyl group. Examples include alkyl-NH-alkyl-NH-alkyl-, with the term alkyl as defined herein.

As used herein, "arylaminoalkyl" refers to an aryl group connected, as a substituent, to an amino group that is connected, as a substituent, to an alkyl group. Examples include aryl-NH-alkyl-, with the terms aryl and alkyl as defined herein.

As used herein, "aminoalkyloxy" refers to an amino group connected, as a substituent, to an alkyloxy group. Examples include H2N-alkyl-O— and H2N-alkoxy-, with the terms alkyl and alkoxy as defined herein.

As used herein, "aminoalkyloxyalkyl" refers to an amino group connected, as a substituent, to an alkyloxy group connected, as a substituent, to an alkyl group. Examples include H2N-alkyl-O-alkyl- and H2N-alkoxy-alkyl- with the terms alkyl and alkoxy as defined herein.

As used herein, "aminoalkylcarboxy" refers to an amino group connected, as a substituent, to an alkyl group connected, as a substituent, to a carboxy group. Examples include H2N-alkyl-C(=O)O— and H2N-alkyl-O—C(=O)— with the term alkyl as defined herein.

As used herein, "aminoalkylaminocarbonyl" refers to an amino group connected, as a substituent, to an alkyl group connected, as a substituent, to an amino group connected, as a substituent, to a carbonyl group. Examples include H2N-alkyl-NH—C(=O)— with the term alkyl as defined herein.

As used herein, "aminoalkylcarboxamido" refers to an amino group connected, as a substituent, to an alkyl group connected, as a substituent, to a carbonyl group connected, as a substituent to an amino group. Examples include H2N-alkyl-C(=O)—NH— with the term alkyl as defined herein.

As used herein, "azidoalkyloxy" refers to an azido group connected as a substituent, to an alkyloxy group. Examples include N3-alkyl-O— and N3-alkoxy- with the terms alkyl and alkoxy as defined herein.

As used herein, "cyanoalkyloxy" refers to a cyano group connected as a substituent, to an alkyloxy group. Examples include NC-alkyl-O— and NC-alkoxy- with the terms alkyl and alkoxy as defined herein.

As used herein, "guanidinoalkyloxy" refers to a guanidinyl group connected, as a substituent, to an alkyloxy group. Examples include

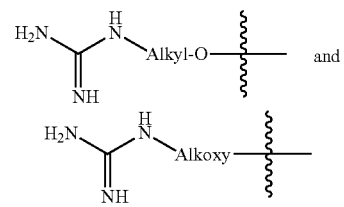

with the terms "alkyl" and "alkoxy" as defined herein.

As used herein, "guanidinoalkylcarboxy" refers to a guanidinyl group connected, as a substituent, to an alkyl group connected, as a substituent, to a carboxy group. Examples include

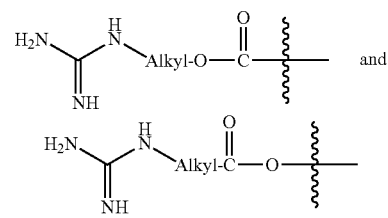

with the term "alkyl" as defined herein.

As used herein, "quaternaryammoniumalkylcarboxy" refers to a quaternized amino group connected, as a substituent, to an alkyl group connected, as a substituent, to a carboxy group. Examples include

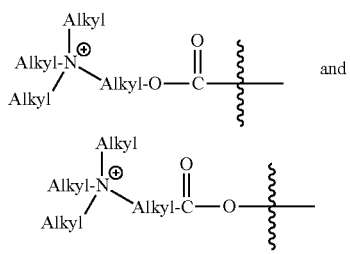

with the term "alkyl" as defined herein.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens.

As used herein, the term "amino acid" refers to any amino acid (both standard and non-standard amino acids), including, but not limited to, α-amino acids, β-amino acids, γ-amino acids and δ-amino acids. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine.

A linking group is a divalent moiety used to link one steroid to another steroid. In some embodiments, the linking group is used to link a first CSA with a second CSA (which may be the same or different). An example of a linking group is ($C_1$-$C_{10}$) alkyloxy-($C_1$-$C_{10}$) alkyl.

The terms "P.G." or "protecting group" or "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis,* 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (BOC), acetyl, or isobutyryl); arylalkylcarbonyls and arylalkoxycarbonyls (e.g., benzyloxycarbonyl); substituted methyl ether (e.g. methoxymethyl ether); substituted ethyl ether; a substituted benzyl ether; tetrahydropyranyl ether; silyls (e.g., trimethylsilyl, triethylsilyl, triisopropylsilyl, t-xbutyldimethylsilyl, triiso-propylsilyloxymethyl, [2-(trimethylsilyl)ethoxy]methyl or t-butyldiphenylsilyl); esters (e.g. benzoate ester); carbonates (e.g. methoxymethylcarbonate); sulfonates (e.g. tosylate or mesylate); acyclic ketal (e.g. dimethyl acetal); cyclic ketals (e.g., 1,3-dioxane, 1,3-dioxolanes, and those described herein); acyclic acetal; cyclic acetal (e.g., those described herein); acyclic hemiacetal; cyclic hemiacetal; cyclic dithioketals (e.g., 1,3-dithiane or 1,3-dithiolane); orthoesters (e.g., those described herein) and triarylmethyl groups (e.g., trityl; monomethoxytrityl (MMTr); 4,4'-dimethoxytrityl (DMTr); 4,4',4''-trimethoxytrityl (TMTr); and those described herein). Amino-protecting groups are known to those skilled in the art. In general, the species of protecting group is not critical, provided that it is stable to the conditions of any subsequent reaction(s) on other positions of the compound and can be removed at the appropriate point without adversely affecting the remainder of the molecule. In addition, a protecting group may be substituted for another after substantive synthetic transformations are complete. Clearly, where a compound differs from a compound disclosed herein only in that one or more protecting groups of the disclosed compound has been substituted with a different protecting group, that Ceragenin compounds include, but are not limited to, compounds having cationic groups (e.g., amine or guanidine groups) covalently attached to a steroid backbone or scaffold at any carbon position, e.g., cholic acid. In various embodiments, a group is covalently attached at anyone, or more, of positions $R_3$, $R_7$, and $R_{12}$ of the sterol backbone. In additional embodiments, a group is absent from any one or more of positions $R_3$, $R_7$, and $R_{12}$ of the sterol backbone.

Anti-microbial CSA compounds described herein may also include a tether or "tail moiety" attached to the sterol backbone. The tail moiety may have variable chain length or size and may be one of charged, uncharged, polar, non-polar, hydrophobic, amphipathic, and the like. In various embodiments, a tail moiety may be attached at $R_{17}$ of Formula (II). A tail moiety may include the heteroatom (O or N) covalently coupled to the sterol backbone.

The tail moiety may, for example, be configured to alter the hydrophobicity/hydrophilicity of the ceragenin compound. Ceragenin compounds of the present disclosure having different degrees of hydrophobicity/hydrophilicity may, for example, have different rates of uptake into different target microbes. Likewise, altering the hydrophobicity/hydrophilicity of the ceragenin compounds described herein may affect the retention of the ceragenin compounds in certain media.

In some embodiments, compounds include, but are not limited to, compounds having amine or guanidine groups covalently attached to a steroid backbone or scaffold at any carbon position, e.g., cholic acid. In various embodiments, a group is covalently attached at anyone, or more, of positions C3, C7 and C12 of the steroid backbone or scaffold. In additional embodiments, a group is absent from anyone, or more, of positions C3, C7 and C12 of the steroid backbone or scaffold. Compounds that include such groups can include a tether, the tether having variable chain length or size. As used herein, the terms "tether" or "tethered," when used in reference to a compound, refers to the chain of atoms between the steroid backbone or scaffold and a terminal amino or guanidine group. In various embodiments, a tether is covalently attached at anyone, or more, of positions C3, C7 and C12. In additional embodiments, a tether is lacking at anyone, or more, of positions C3, C7 and C12. A tether length may include the heteroatom (O or N) covalently attached to the steroid backbone In some embodiments, other ring systems can also be used, e.g., 5-member fused rings. Compounds with backbones having a combination of 5- and 6-membered rings are also contemplated. Amine or guanidine groups can be separated from the backbone by at least one, two, three, four or more atoms. The backbone can be used to orient the amine or guanidine groups on one face, or plane, of the steroid.

As used in this specification and the appended claims, the singular forms "a", "an", and "the" include plural referents unless the context clearly dictates otherwise.

Compounds and Compositions:

Compounds useful in accordance with this disclosure are described herein, both generically and with particularity, and in U.S. Pat. Nos. 6,350,738, 6,486,148, 6,767,904, 7,598,234, and 7,754,705, which are incorporated herein by reference. Compounds include steroid derivatives, such as cationic steroid antimicrobial ("CSA") compounds that exhibit one or more antimicrobal activities or functions for treating mastitis. The skilled artisan will recognize the compounds within the generic formulas set forth herein. Additional compounds of the disclosure having one or more activities or functions are described and can be characterized using the assays set forth herein and in the art.

FIG. 1A illustrates exemplary hydrolysable CSA compounds.

Figure 1B:
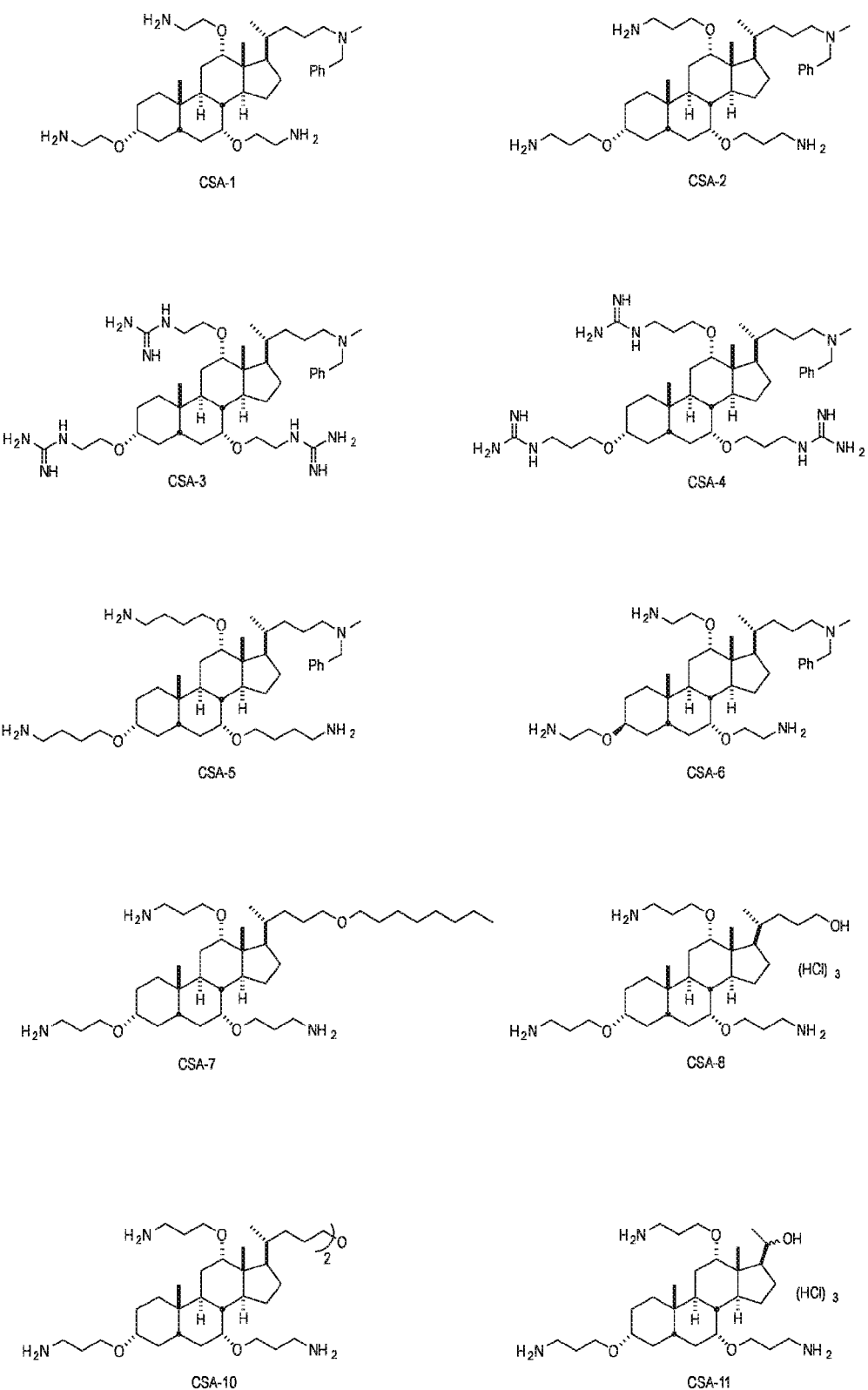
FIG. 1B illustrates exemplary non-hydrolysable CSA compounds.
Figure 1B:
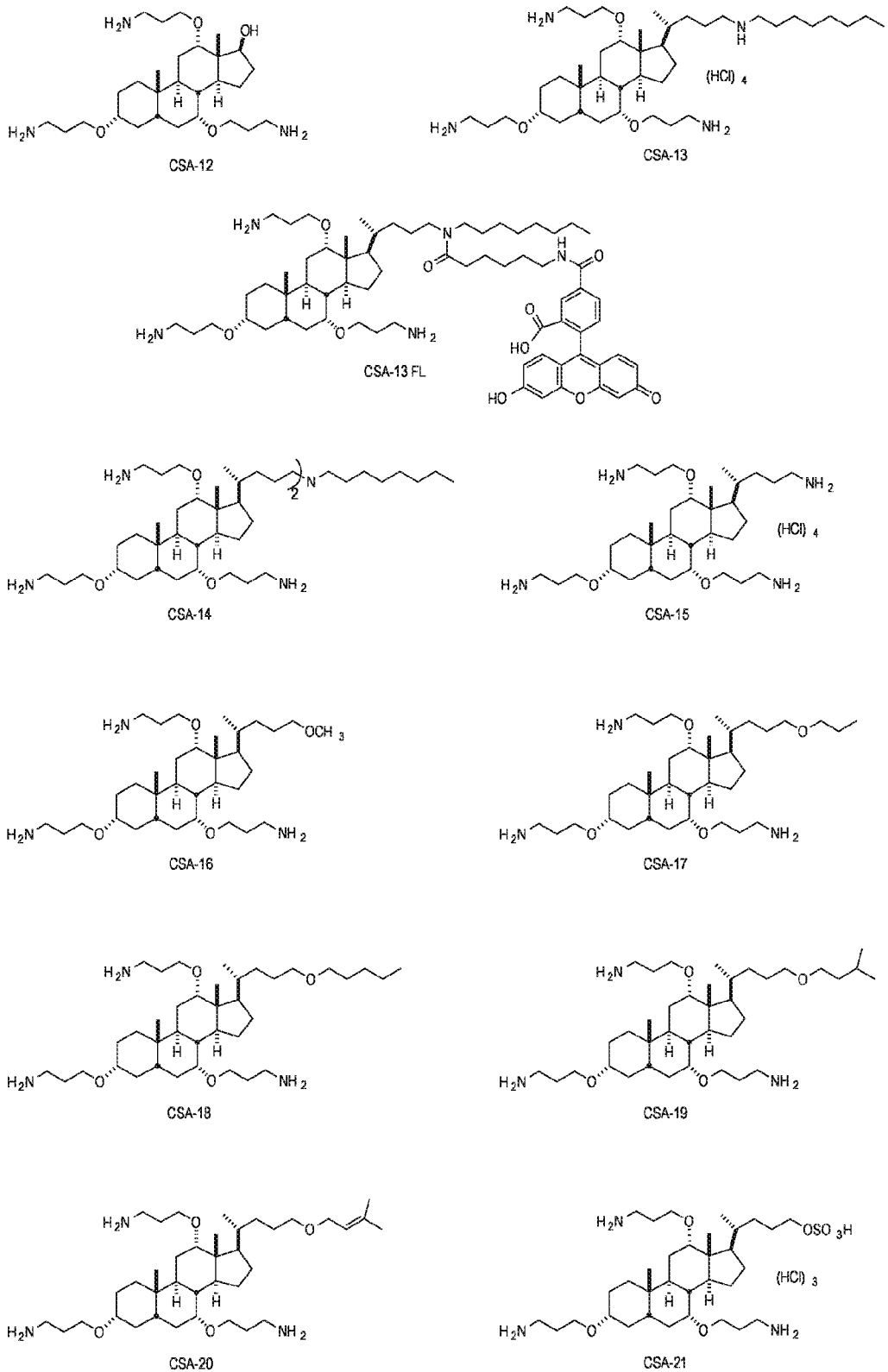
Figure 1B:
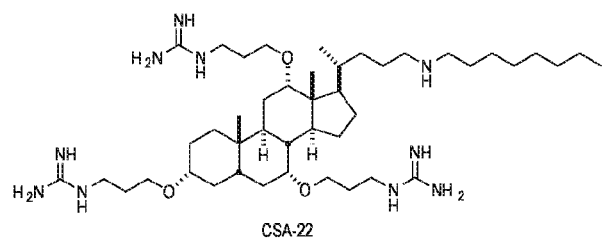
Figure 1B:
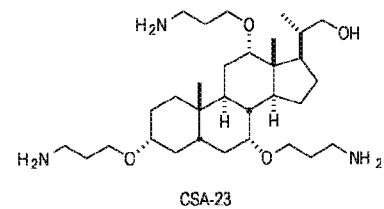
Figure 1B:
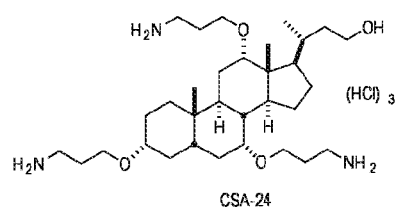
Figure 1B:
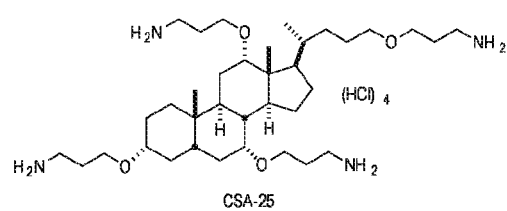
Figure 1B:
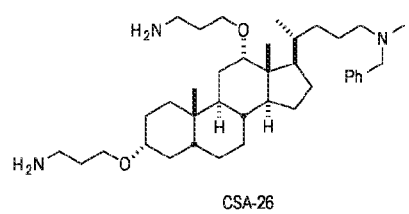
Figure 1B:
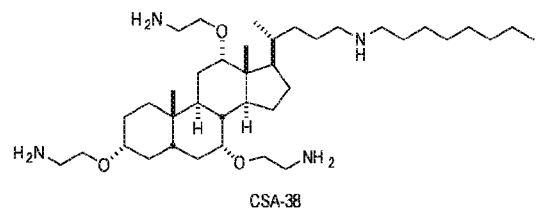
Figure 1B:
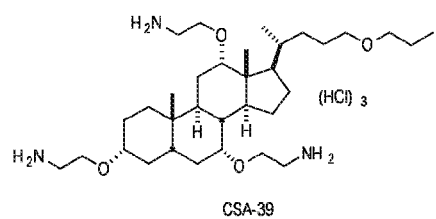
Figure 1B:
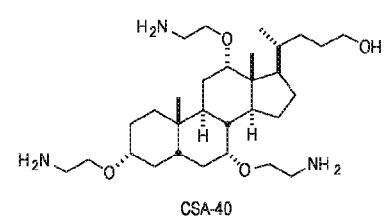
Figure 1B:
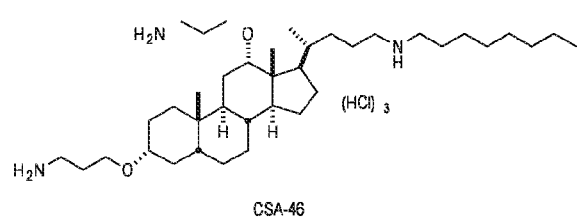
Figure 1B:
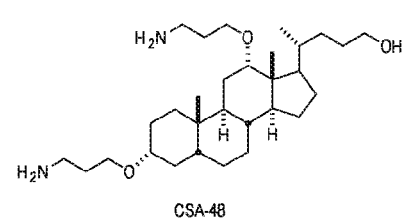
Figure 1B:
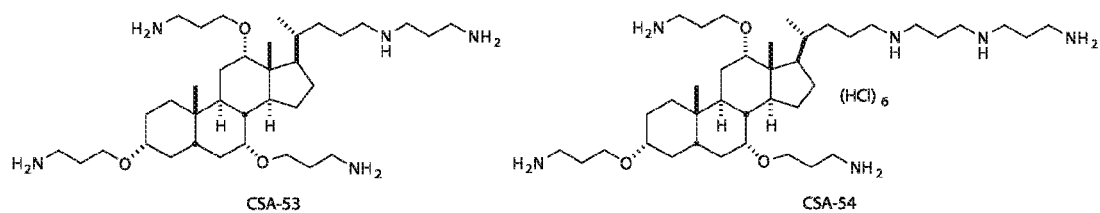
Figure 1B:
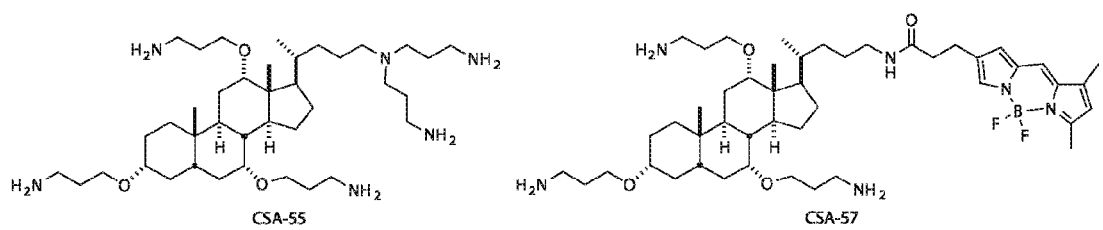
Figure 1B:
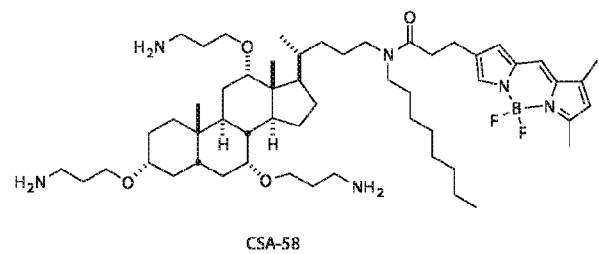
Figure 1B:
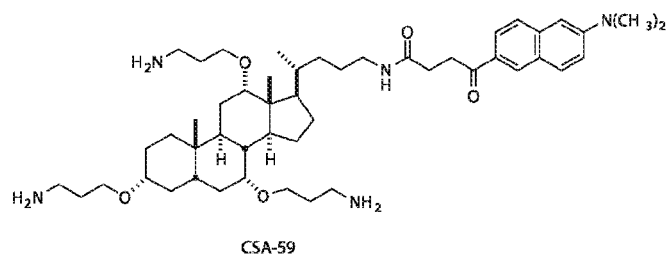
Figure 1B:
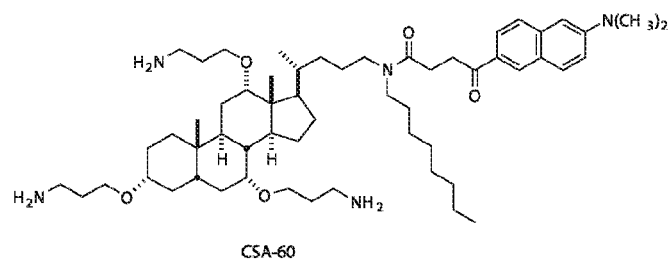
Figure 1B:
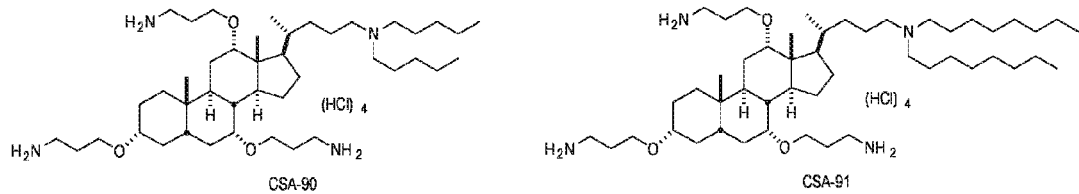
Figure 1B:
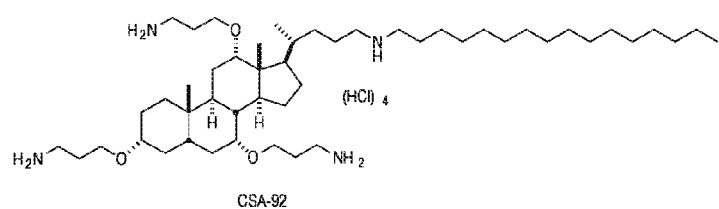
Figure 1B:
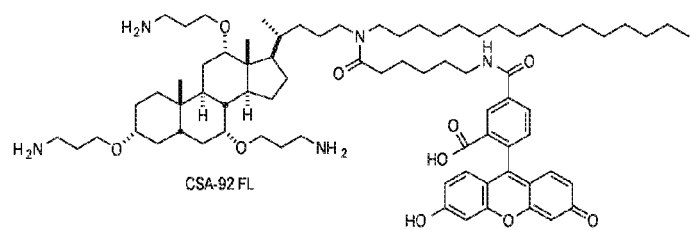
Figure 1B:
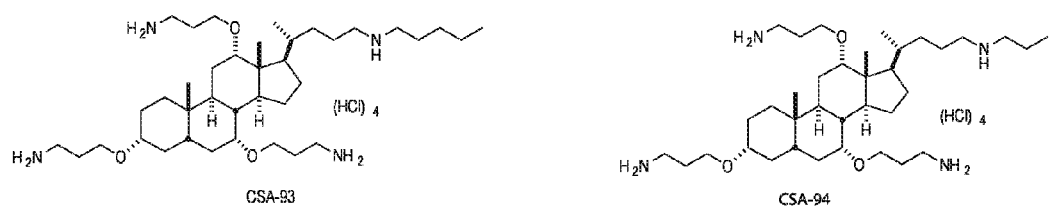
Figure 1B:
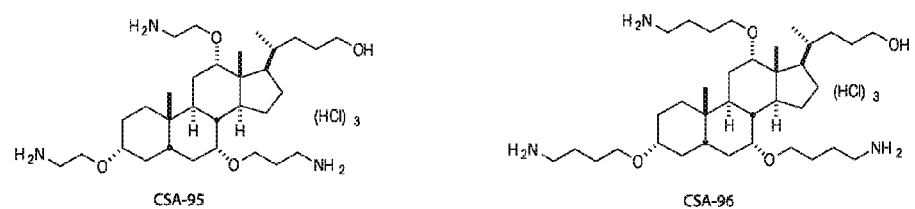
Figure 1B:
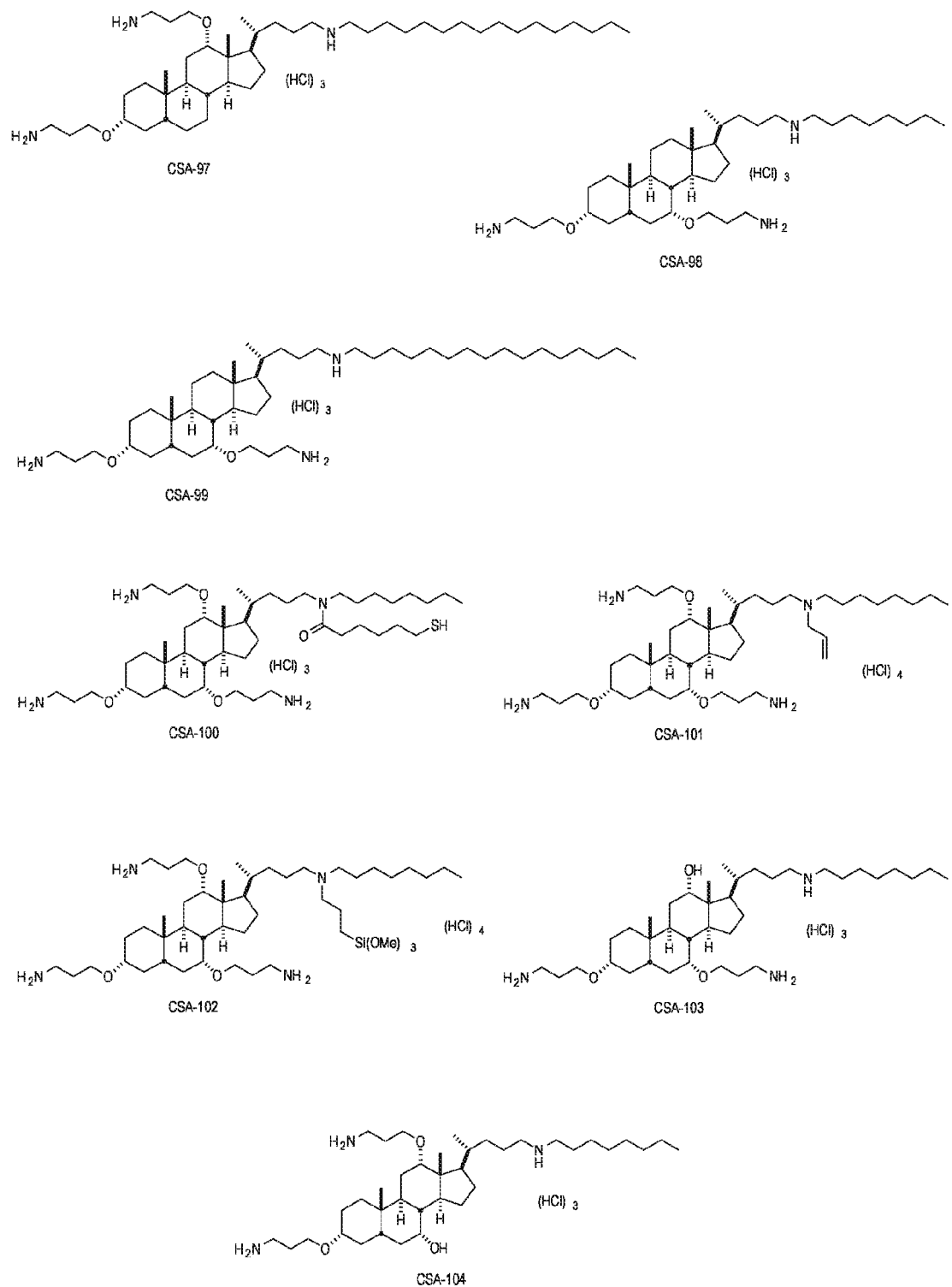
Figure 1B:
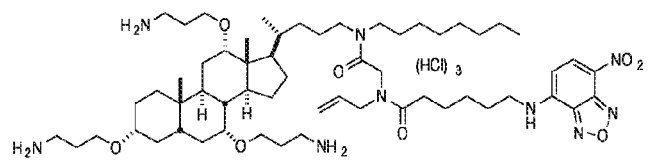
Figure 1B:
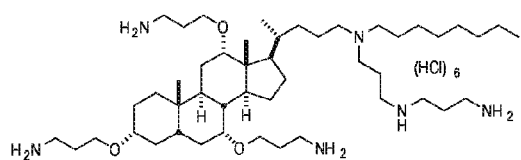
Figure 1B:
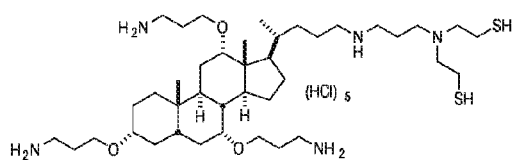
Figure 1B:
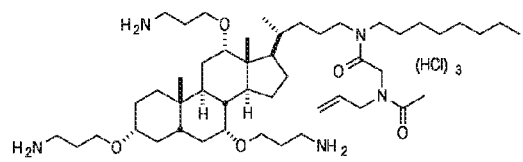
Figure 1B:
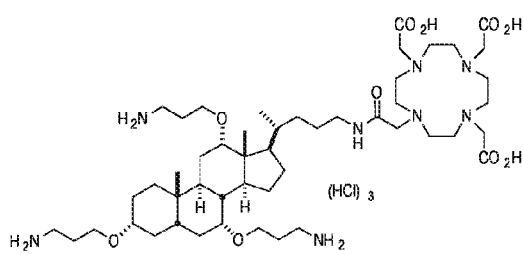
Figure 1B:
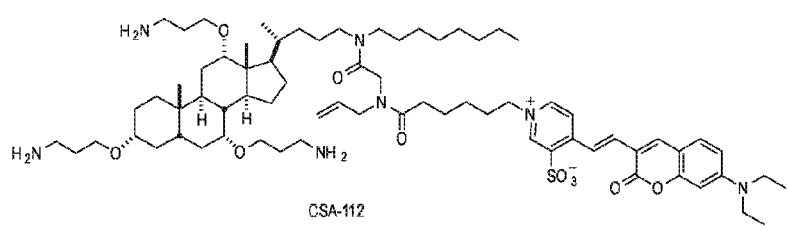
Figure 1B:
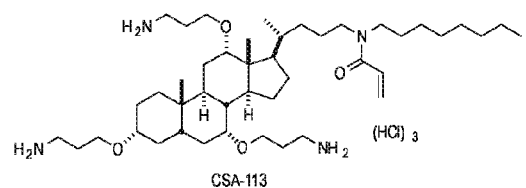
Figure 1B:
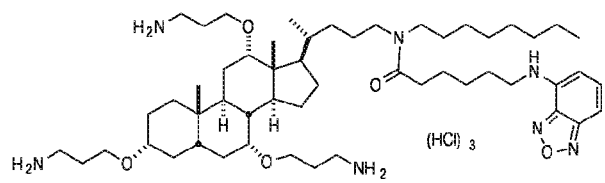
Figure 1B:
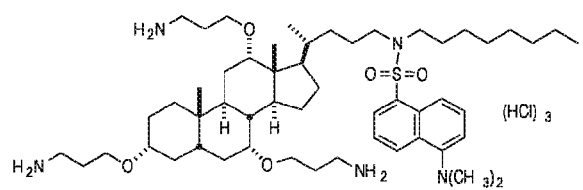
Figure 1B:
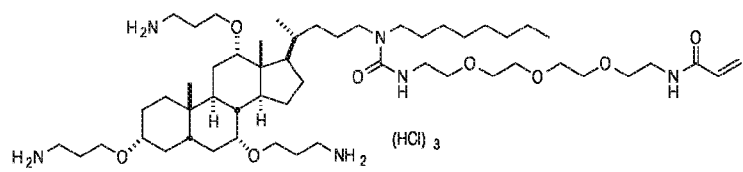
Figure 1B:
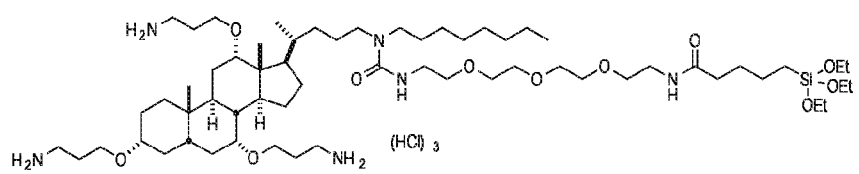
Figure 1B:
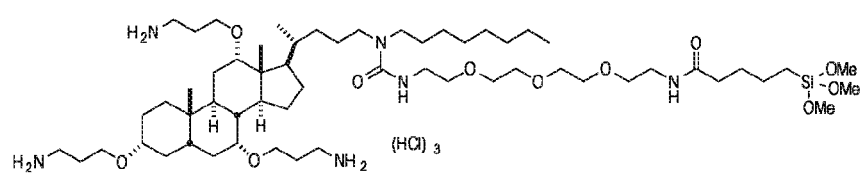
Figure 1B:
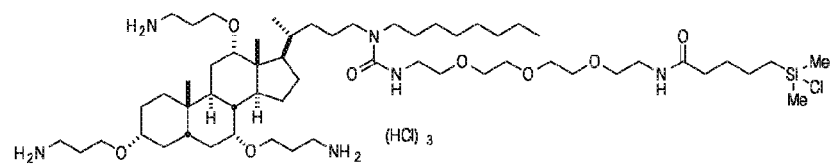
Figure 1B:
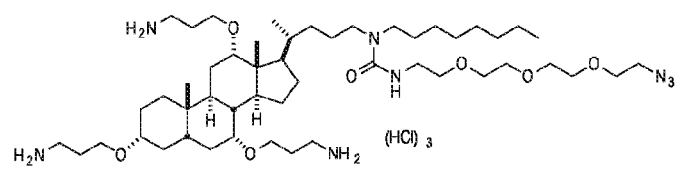
Figure 1B:
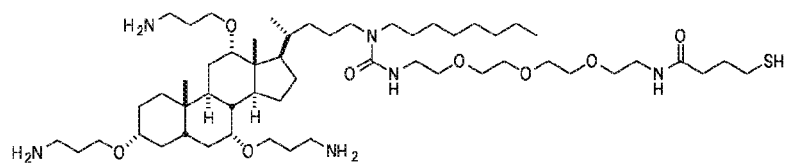
Figure 1B:
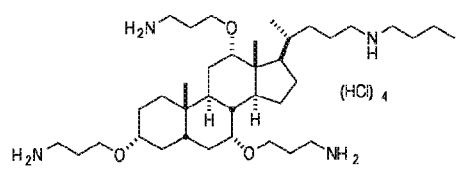
Figure 1B:
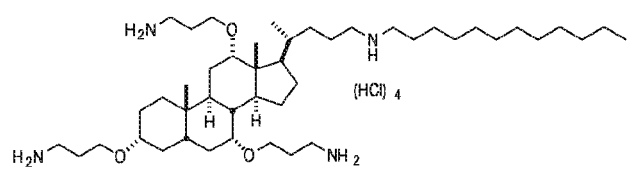
Figure 1B:
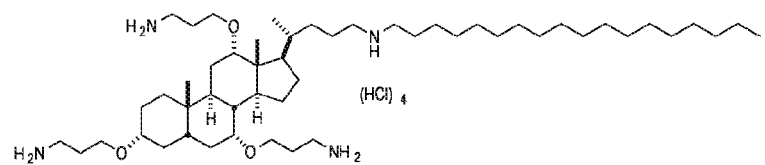
Figure 1B:
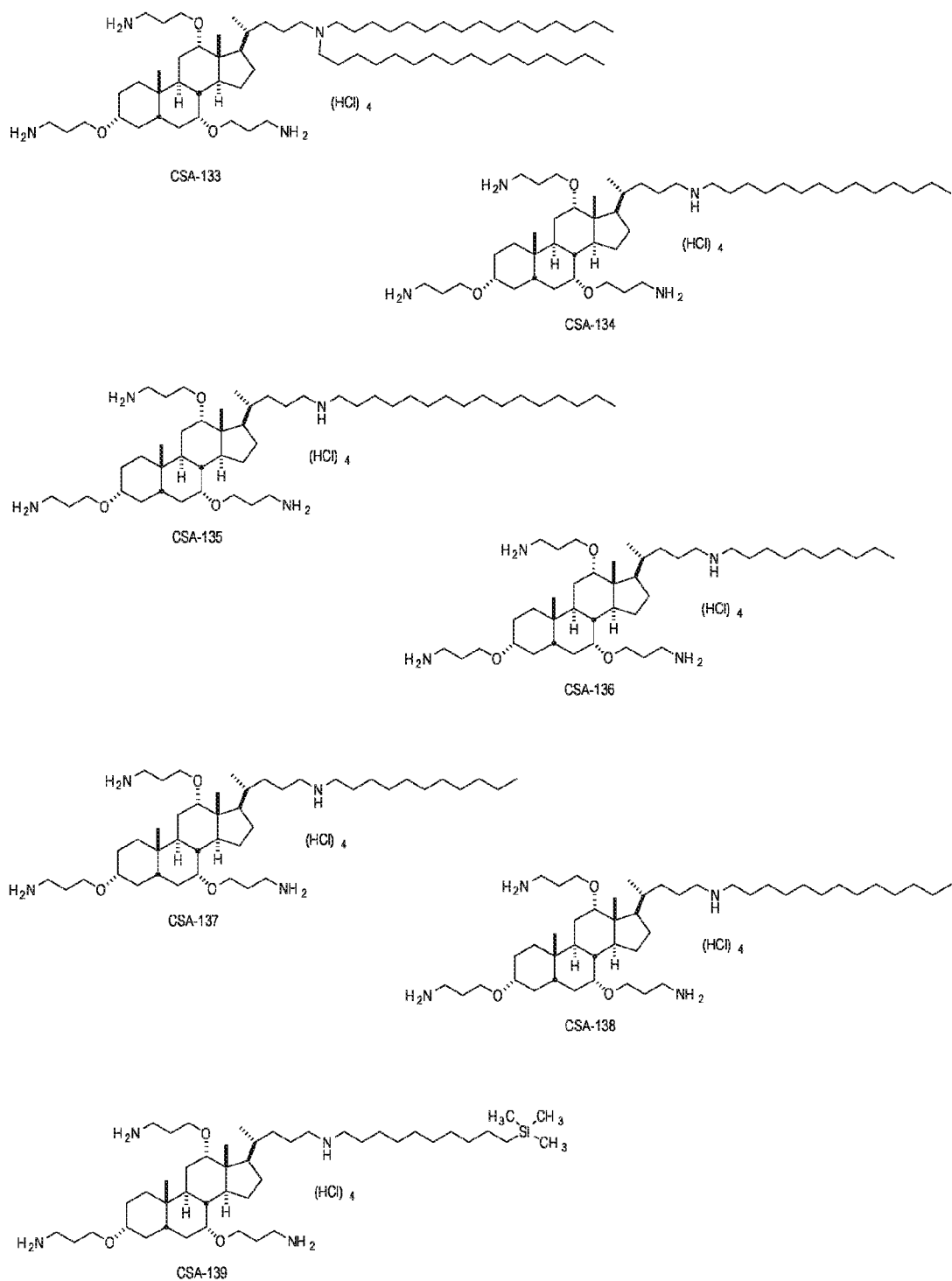

FIG. 1B illustrates exemplary non-hydrolysable CSA compounds.

Some embodiments disclosed herein relate to a compound selected from Formula (I) or a pharmaceutically acceptable salt of the foregoing and can have the structure:

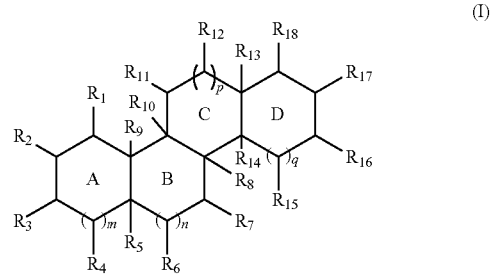

(I)

where m, n, p, and q are independently 0 or 1; $R^1$-$R^{18}$ represent substituents that are attached to the indicated atom on the steroid backbone (i.e., steroid group); and at least two, preferably at least three, of $R^1$-$R^{18}$ each include a cationic group.

In one embodiment, each of rings A, B, C, and D is independently saturated, or is fully or partially unsaturated, provided that at least two of rings A, B, C, and D are saturated; m, n, p, and q are independently 0 or 1; $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, a substituted or unsubstituted alkyl, substituted or unsubstituted hydroxyalkyl, substituted or unsubstituted alkyloxyalkyl, substituted or unsubstituted alkylcarboxyalkyl, substituted or unsubstituted alkylaminoalkyl, substituted or unsubstituted alkylaminoalkylamino, substituted or unsubstituted alkylaminoalkylaminoalkylamino, a substituted or unsubstituted aminoalkyl, a substituted or unsubstituted aryl, a substituted or unsubstituted arylaminoalkyl, substituted or unsubstituted haloalkyl, substituted or unsubstituted alkenyl, substituted or unsubstituted alkynyl, oxo, a linking group attached to a second steroid, a substituted or unsubstituted aminoalkyloxy, a substituted or unsubstituted aminoalkyloxyalkyl, substituted or unsubstituted aminoalkylcarboxy, a substituted or unsubstituted aminoalkylaminocarbonyl, a substituted or unsubstituted aminoalkylcarboxamido, a substituted or unsubstituted di(alkyl)aminoalkyl, a substituted or unsubstituted C-carboxyalkyl, $H_2N$—$HC(Q_5)$-$C(O)$—$O$—, $H_2N$—$HC(Q_5)$-$C(O)$—$N(H)$—, substituted or unsubstituted azidoalkyloxy, substituted or unsubstituted cyanoalkyloxy, P.G.-$HN$—$HC(Q_5)$-$C(O)$—$O$—, substituted or unsubstituted guanidinoalkyloxy, substituted or unsubstituted quaternaryammoniumalkylcarboxy, and substituted or unsubstituted guanidinoalkyl carboxy, where $Q_5$ is a side chain of any amino acid (including a side chain of glycine, i.e., H), and P.G. is an amino protecting group; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, a substituted or unsubstituted alkyl, substituted or unsubstituted hydroxyalkyl, substituted or unsubstituted alkyloxyalkyl, a substituted or unsubstituted aminoalkyl, a substituted or unsubstituted aryl, substituted or unsubstituted haloalkyl, substituted or unsubstituted alkenyl, substituted or unsubstituted alkynyl, oxo, a linking group attached to a second steroid, a substituted or unsubstituted aminoalkyloxy, a substituted or unsubstituted aminoalkylcarboxy, a substituted or unsubstituted aminoalkylaminocarbonyl, a substituted or unsubstituted di(alkyl)aminoalkyl, a substituted or unsubstituted C-carboxyalkyl, $H_2N$—$HC(Q_5)$-$C(O)$—$O$—, $H_2N$—$HC(Q_5)$-$C(O)$—$N(H)$—, substituted or unsubstituted azidoalkyloxy, substituted or unsubstituted cyanoalkyloxy, P.G.-$HN$—$HC(Q_5)$-$C(O)$—$O$—, substituted or unsubstituted guanidinoalkyloxy, and substituted or unsubstituted guanidinoalkylcarboxy, where $Q_5$ is a side chain of any amino acid, P.G. is an amino protecting group; provided that at least two or three of $R_{1\text{-}4}$, $R_6$, $R_7$, $R_{11}$, $R_{12}$, $R_{15}$, $R_{16}$, $R_{17}$, and $R_{18}$ are independently selected from the group consisting of a substituted or unsubstituted aminoalkyl, a substituted or unsubstituted aminoalkyloxy, substituted or unsubstituted alkylcarboxyalkyl, substituted or unsubstituted alkylaminoalkylamino, substituted or unsubstituted alkylaminoalkylaminoalkylamino, a substituted or unsubstituted arylaminoalkyl, a substituted or unsubstituted aminoalkylcarboxy, a substituted or unsubstituted aminoalkyloxyaminoalkylaminocarbonyl, a substituted or unsubstituted aminoalkylaminocarbonyl, a substituted or unsubstituted aminoalkylcarboxyamido, a substituted or unsubstituted quaternaryammoniumalkylcarboxy, a substituted or unsubstituted di(alkyl)aminoalkyl, a substituted or unsubstituted C-carboxyalkyl, $H_2N$—$HC(Q_5)$-$C(O)$—$O$—, $H_2N$—$HC(Q_5)$-$C(O)$—$N(H)$—, substituted or unsubstituted azidoalkyloxy, substituted or unsubstituted cyanoalkyloxy, P.G.-$HN$—$HC(Q_5)$-$C(O)$—$O$—, substituted or unsubstituted guanidinoalkyloxy, a substituted or unsubstituted guanidinoalkylcarboxy, or a pharmaceutically acceptable salt thereof.

In some embodiments, $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, a substituted or unsubstituted $(C_1$-$C_{18})$ alkyl, substituted or unsubstituted $(C_1$-$C_{18})$ hydroxyalkyl, substituted or unsubstituted $(C_1$-$C_{18})$ alkyloxy-$(C_1$-$C_{18})$ alkyl, substituted or unsubstituted $(C_1$-$C_{18})$ alkylcarboxy-$(C_1$-$C_{18})$ alkyl, substituted or unsubstituted $(C_1$-$C_{18})$ alkylamino-$(C_1$-$C_{18})$alkyl, substituted or unsubstituted $(C_1$-$C_{18})$ alkylamino-$(C_1$-$C_{18})$ alkylamino, substituted or unsubstituted $(C_1$-$C_{18})$ alkylamino-$(C_1$-$C_{18})$ alkylamino-$(C_1$-$C_{18})$ alkylamino, a substituted or unsubstituted $(C_1$-$C_{18})$ aminoalkyl, a substituted or unsubstituted aryl, a substituted or unsubstituted arylamino-$(C_1$-$C_{18})$ alkyl, substituted or unsubstituted $(C_1$-$C_{18})$ haloalkyl, substituted or unsubstituted $(C_2$-$C_6)$ alkenyl, substituted or unsubstituted $(C_2$-$C_6)$ alkynyl, oxo, a linking group attached to a second steroid, a substituted or unsubstituted $(C_1$-$C_{18})$ aminoalkyloxy, a substituted or unsubstituted $(C_1$-$C_{18})$ aminoalkyloxy-$(C_1$-$C_{18})$ alkyl, a substituted or unsubstituted $(C_1$-$C_{18})$ aminoalkylcarboxy, a substituted or unsubstituted $(C_1$-$C_{18})$ aminoalkylaminocarbonyl, a substituted or unsubstituted $(C_1$-$C_{18})$ aminoalkylcarboxamido, a substituted or unsubstituted di($C_1$-$C_{18}$ alkyl)aminoalkyl, a substituted or unsubstituted C-carboxy$(C_1$-$C_{18})$alkyl, $H_2N$—$HC(Q_5)$-$C(O)$—$O$—, $H_2N$—$HC(Q_5)$-$C(O)$—$N(H)$—, substituted or unsubstituted $(C_1$-$C_{18})$ azidoalkyloxy, substituted or unsubstituted $(C_1$-$C_{18})$ cyanoalkyloxy, P.G.-$HN$—$HC(Q_5)$-$C(O)$—$O$—, substituted or unsubstituted $(C_1$-$C_{18})$ guanidinoalkyloxy, substituted or unsubstituted $(C_1$-$C_{18})$ quaternaryammoniumalkylcarboxy, and substituted or unsubstituted $(C_1$-$C_{18})$ guanidinoalkyl carboxy, where $Q_5$ is a side chain of any amino acid (including a side chain of glycine, i.e., H), and P.G. is an amino protecting group; and $R_5$, $R_8$, $R_9$, $R_{10}$, $R_{13}$, $R_{14}$ and $R_{17}$ are independently deleted when one of rings A, B, C, or D is unsaturated so as to complete the valence of the carbon atom at that site, or $R_5$, $R_8$, $R_9$, $R_{10}$, $R_{13}$, and $R_{14}$ are independently selected from the group consisting of hydrogen, hydroxyl, a substituted or unsubstituted $(C_1$-$C_{18})$ alkyl, substituted or unsubstituted $(C_1$-$C_{18})$ hydroxyalkyl, substituted or unsubstituted $(C_1$-$C_{18})$ alkyloxy-$(C_1$-$C_{18})$ alkyl, a substituted or unsubstituted $(C_1$-$C_{18})$ aminoalkyl, a substituted or unsubstituted aryl, substituted or unsubstituted $(C_1$-$C_{18})$ haloalkyl, substituted or unsubstituted $(C_2$-$C_6)$ alkenyl, substituted or unsubstituted $(C_2$-$C_6)$ alkynyl, oxo, a linking group attached to a second steroid, a substituted or unsubstituted $(C_1$-$C_{18})$ aminoalkyloxy, a substituted or unsubstituted $(C_1$-$C_{18})$ aminoalkylcarboxy, a substituted or unsubstituted $(C_1$-$C_{18})$ aminoalkylaminocarbonyl, di($C_1$-$C_{18}$ alkyl)aminoalkyl, a substituted or unsubstituted C-carboxy$(C_1$-$C_{18})$alkyl, $H_2N$—$HC(Q_5)$-$C(O)$—$O$—, $H_2N$—$HC(Q_5)$-$C(O)$—$N(H)$—, substituted or unsubstituted azidoalkyloxy, substituted or unsubstituted $(C_1$-$C_{18})$ cyanoalkyloxy, P.G.-$HN$—$HC(Q_5)$-$C(O)$—$O$—, substituted or unsubstituted $(C_1$-$C_{18})$ guanidinoalkyloxy, and substituted or unsubstituted $(C_1$-$C_{18})$ guanidinoalkylcarboxy, where Q5 is a side chain of any amino acid, and P.G. is an amino protecting group; provided that at least two or three of $R_{1\text{-}4}$, $R_6$, $R_7$, $R_{11}$, $R_{12}$, $R_{15}$, $R_{16}$, $R_{17}$, and $R_{18}$ are independently selected from the group consisting of a substituted or unsubstituted ($C_1$-$C_{18}$) aminoalkyl, a substituted or unsubstituted ($C_1$-$C_{18}$) aminoalkyloxy, substituted or unsubstituted ($C_1$-$C_{18}$) alkylcarboxy-($C_1$-$C_{18}$) alkyl, substituted or unsubstituted ($C_1$-$C_{18}$) alkylamino-($C_1$-$C_{18}$) alkylamino, substituted or unsubstituted ($C_1$-$C_{18}$) alkylamino-($C_1$-$C_{18}$) alkylamino ($C_1$-$C_{18}$) alkylamino, a substituted or unsubstituted ($C_1$-$C_{18}$) aminoalkylcarboxy, a substituted or unsubstituted arylamino ($C_1$-$C_{18}$) alkyl, a substituted or unsubstituted ($C_1$-$C_{18}$) aminoalkyloxy ($C_1$-$C_{18}$) aminoalkylaminocarbonyl, a substituted or unsubstituted ($C_1$-$C_{18}$) aminoalkylaminocarbonyl, a substituted or unsubstituted ($C_1$-$C_{18}$) aminoalkylcarboxyamido, a substituted or unsubstituted ($C_1$-$C_{18}$) quaternaryammoniumalkylcarboxy, substituted or unsubstituted di($C_1$-$C_{18}$ alkyl)aminoalkyl, a substituted or unsubstituted C-carboxy ($C_1$-$C_{18}$)alkyl, $H_2N$—$HC(Q_5)$-$C(O)$—$O$—, $H_2N$—$HC(Q_5)$-$C(O)$—$N(H)$—, substituted or unsubstituted ($C_1$-$C_{18}$) azidoalkyloxy, substituted or unsubstituted ($C_1$-$C_{18}$) cyanoalkyloxy, P.G.-HN—HC(Q5)-C(O)—O—, substituted or unsubstituted ($C_1$-$C_{18}$) guanidinoalkyloxy, a substituted or unsubstituted ($C_1$-$C_{18}$) guanidinoalkylcarboxy, or a pharmaceutically acceptable salt thereof.

In some embodiments, $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$)alkyl, unsubstituted ($C_1$-$C_{18}$) alkylamino-($C_1$-$C_{18}$) alkylamino, unsubstituted ($C_1$-$C_{18}$) alkylamino-($C_1$-$C_{18}$) alkylamino-($C_1$-$C_{18}$) alkylamino, an unsubstituted ($C_1$-$C_{18}$) aminoalkyl, an unsubstituted aryl, an unsubstituted arylamino-($C_1$-$C_{18}$) alkyl, oxo, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkylaminocarbonyl, an unsubstituted ($C_1$-$C_{18}$) aminoalkylcarboxamido, an unsubstituted di($C_1$-$C_{18}$ alkyl)aminoalkyl, an unsubstituted C-carboxy($C_1$-$C_{18}$)alkyl, unsubstituted ($C_1$-$C_{18}$) guanidinoalkyloxy, unsubstituted ($C_1$-$C_{18}$) quaternaryammoniumalkylcarboxy, and unsubstituted ($C_1$-$C_{18}$) guanidinoalkyl carboxy; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$)alkyl, unsubstituted ($C_1$-$C_{18}$) alkylamino-($C_1$-$C_{18}$) alkylamino, unsubstituted ($C_1$-$C_{18}$) alkylamino-($C_1$-$C_{18}$) alkylamino-($C_1$-$C_{18}$) alkylamino, an unsubstituted ($C_1$-$C_{18}$) aminoalkyl, an unsubstituted aryl, an unsubstituted arylamino-($C_1$-$C_{18}$) alkyl, oxo, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkylaminocarbonyl, an unsubstituted ($C_1$-$C_{18}$) aminoalkylcarboxamido, an unsubstituted di($C_1$-$C_{18}$ alkyl)aminoalkyl, an unsubstituted C-carboxy($C_1$-$C_{18}$)alkyl, unsubstituted ($C_1$-$C_{18}$) guanidinoalkyloxy, unsubstituted ($C_1$-$C_{18}$) quaternaryammoniumalkylcarboxy, and unsubstituted ($C_1$-$C_{15}$) guanidinoalkyl carboxy; provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of hydrogen, hydroxyl, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$)alkyl, unsubstituted ($C_1$-$C_{18}$) alkylamino-($C_1$-$C_{18}$) alkylamino, unsubstituted ($C_1$-$C_{18}$) alkylamino-($C_1$-$C_{18}$) alkylamino-($C_1$-$C_{18}$) alkylamino, an unsubstituted ($C_1$-$C_{18}$) aminoalkyl, an unsubstituted aryl, an unsubstituted arylamino-($C_1$-$C_{18}$) alkyl, oxo, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkylaminocarbonyl, an unsubstituted ($C_1$-$C_{18}$) aminoalkylcarboxamido, an unsubstituted di($C_1$-$C_{18}$ alkyl)aminoalkyl, an unsubstituted C-carboxy($C_1$-$C_{18}$)alkyl, unsubstituted ($C_1$-$C_{18}$) guanidinoalkyloxy, unsubstituted ($C_1$-$C_{18}$) quaternaryammoniumalkylcarboxy, unsubstituted ($C_1$-$C_{18}$) guanidinoalkyl carboxy, or a pharmaceutically acceptable salt thereof.

In some embodiments, the compound of Formula (I) or pharmaceutically acceptable salt can be represented by Formula (IA):

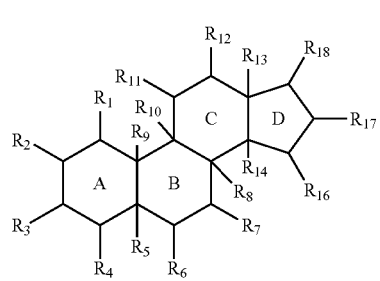

(IA)

In some embodiments, each of rings A, B, C, and D is independently saturated.

In some embodiments, one or more of rings A, B, C, and D are heterocyclic.

In some embodiments, rings A, B, C, and D are non-heterocyclic.

In some embodiments, $R_1$, $R_7$, $R_{12}$, and $R_{15}$ are independently selected from the group consisting of hydrogen, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$)alkyl, unsubstituted ($C_1$-$C_{18}$) alkylamino-($C_1$-$C_{18}$) alkylamino, unsubstituted ($C_1$-$C_{18}$) alkylamino-($C_1$-$C_{18}$) alkylamino-($C_1$-$C_{18}$) alkylamino, an unsubstituted ($C_1$-$C_{18}$) aminoalkyl, an unsubstituted arylamino-($C_1$-$C_{15}$) alkyl, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkylaminocarbonyl, an unsubstituted ($C_1$-$C_{18}$) aminoalkylcarboxamido, an unsubstituted di($C_1$-$C_{18}$ alkyl)aminoalkyl, unsubstituted ($C_1$-$C_{18}$) guanidinoalkyloxy, unsubstituted ($C_1$-$C_{18}$) quaternaryammoniumalkylcarboxy, and unsubstituted ($C_1$-$C_{18}$) guanidinoalkyl carboxy; and $R_1$, $R_2$, $R_4$, $R_5$, $R_6$, $R_8$, $R_9$, $R_{10}$, $R_{11}$, $R_{13}$, $R_{14}$, $R_{15}$, $R_{16}$, and $R_{17}$ are independently selected from the group consisting of hydrogen and unsubstituted ($C_1$-$C_6$) alkyl.

In some embodiments, $R_3$, $R_7$, $R_{12}$, and $R_{18}$ are independently selected from the group consisting of hydrogen, an unsubstituted ($C_1$-$C_6$) alkyl, unsubstituted ($C_1$-$C_6$) hydroxyalkyl, unsubstituted ($C_1$-$C_{16}$) alkyloxy-($C_1$-$C_5$) alkyl, unsubstituted ($C_1$-$C_{16}$) alkylcarboxy-($C_1$-$C_5$) alkyl, unsubstituted ($C_1$-$C_{16}$) alkylamino-($C_1$-$C_5$)alkyl, unsubstituted ($C_1$-$C_{16}$)

alkylamino-($C_1$-$C_5$) alkylamino, unsubstituted ($C_1$-$C_{16}$) alkylamino-($C_1$-$C_{16}$) alkylamino-($C_1$-$C_5$) alkyl amino, an unsubstituted ($C_1$-$C_{16}$) aminoalkyl, an unsubstituted arylamino-($C_1$-$C_5$) alkyl, an unsubstituted ($C_1$-$C_5$) aminoalkyloxy, an unsubstituted ($C_1$-$C_{16}$) aminoalkyloxy-($C_1$-$C_5$) alkyl, an unsubstituted ($C_1$-$C_5$) aminoalkylcarboxy, an unsubstituted ($C_1$-$C_5$) aminoalkylaminocarbonyl, an unsubstituted ($C_1$-$C_5$) aminoalkylcarboxamido, an unsubstituted di($C_1$-$C_5$ alkyl)amino-($C_1$-$C_5$) alkyl, unsubstituted ($C_1$-$C_5$) guanidinoalkyloxy, unsubstituted ($C_1$-$C_{16}$) quaternaryammoniumalkylcarboxy, and unsubstituted ($C_1$-$C_{16}$) guanidinoalkylcarboxy;

In some embodiments, $R_1$, $R_2$, $R_4$, $R_5$, $R_6$, $R_8$, $R_{10}$, $R_{11}$, $R_{14}$, $R_{16}$, and $R_{17}$ are each hydrogen; and $R_9$ and $R_{13}$ are each methyl.

In some embodiments, $R_3$, $R_7$, $R_{12}$, and $R_{18}$ are independently selected from the group consisting of aminoalkyloxy; aminoalkylcarboxy; alkylaminoalkyl; alkoxycarbonylalkyl; alkylcarbonylalkyl; di(alkyl)aminoalkyl; alkoxycarbonylalkyl; and alkylcarboxyalkyl.

In some embodiments, $R_3$, $R_7$, and $R_{12}$ are independently selected from the group consisting of aminoalkyloxy and aminoalkylcarboxy; and $R_{18}$ is selected from the group consisting of alkylaminoalkyl; alkoxycarbonylalkyl; alkylcarbonyloxyalkyl; di(alkyl)aminoalkyl; alkylaminoalkyl; alkyoxycarbonylalkyl; and alkylcarboxyalkyl.

In some embodiments, $R_3$, $R_7$, and $R_{12}$ are the same.
In some embodiments, $R_3$, $R_7$, and $R_{12}$ are aminoalkyloxy.
In some embodiments, $R_3$, $R_7$, and $R_{12}$ are aminoalkylcarboxy.
In some embodiments, $R_{18}$ is alkylaminoalkyl.
In some embodiments, $R_{18}$ is alkoxycarbonylalkyl.
In some embodiments, $R_{18}$ is di(alkyl)aminoalkyl.
In some embodiments, $R_{18}$ is alkylcarboxyalkyl.

In some embodiments, $R_3$, $R_7$, $R_{12}$, and $R_{18}$ are independently selected from the group consisting of amino-$C_3$-alkyloxy; amino-$C_3$-alkyl-carboxy; $C_8$-alkylamino-$C_5$-alkyl; $C_8$-alkoxy-carbonyl-$C_4$-alkyl; $C_8$-alkyl-carbonyl-$C_4$-alkyl; di-($C_5$-alkyl)amino-$C_5$-alkyl; $C_{13}$-alkylamino-$C_5$-alkyl; $C_6$-alkoxy-carbonyl-$C_4$-alkyl; $C_6$-alkyl-carboxy-$C_4$-alkyl; and $C_{16}$-alkylamino-$C_5$-alkyl.

In various aspects, at least two, or at least three, of m, n, p, and q are 1. In some embodiments, m, n, and p are each 1 and q is 0.

According to other embodiments, compounds can have a structure as shown in Formula (II), which is closely related to, but not identical to, Formula (I):

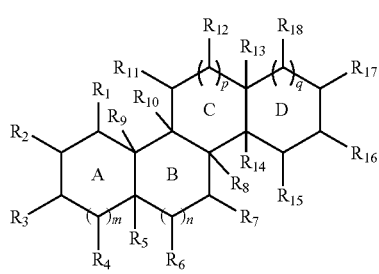

(II)

where each of fused rings A, B, C, and D is independently saturated, or is fully or partially unsaturated, provided that at least two of A, B, C, and D are saturated, wherein rings A, B, C, and D form a ring system; each of m, n, p, and q is independently 0 or 1 (i.e., each ring may independently be 5-membered or 6-membered); each of $R_1$ through $R_4$, $R_6$, $R_7$, $R_{11}$, $R_{12}$, $R_{15}$, $R_{16}$, $R_{17}$, and $R_{18}$ is independently selected from the group consisting of hydrogen, hydroxyl, a substituted or unsubstituted ($C_1$-$C_{10}$) alkyl, ($C_1$-$C_{10}$) hydroxyalkyl, ($C_1$-$C_{10}$)$^{alkyloxy}$-($C_1$-$C_{10}$) alkyl, ($C_1$-$C_{10}$) alkylcarboxy-($C_1$-$C_{10}$) alkyl, ($C_1$-$C_{10}$) alkylamino-($C_1$-$C_{10}$) alkyl, ($C_1$-$C_{10}$) alkylamino-($C_1$-$C_{10}$) alkylamino, ($C_1$-$C_{10}$) alkylamino-($C_1$-$C_{10}$) alkylamino-($C_1$-$C_{10}$) alkylamino-($C_1$-$C_{10}$) alkylamino, a substituted or unsubstituted ($C_1$-$C_{10}$) aminoalkyl, a substituted or unsubstituted aryl, a substituted or unsubstituted arylamino-($C_1$-$C_{10}$) alkyl, ($C_1$-$C_{10}$) haloalkyl, $C_2$-$C_6$ alkenyl, $C_2$-$C_6$ alkynyl, oxo, a linking group attached to a second steroid, a substituted or unsubstituted ($C_1$-$C_{10}$) aminoalkyloxy, a substituted or unsubstituted ($C_1$-$C_{10}$) aminoalkyloxy-($C_1$-$C_{10}$) alkyl, a substituted or unsubstituted ($C_1$-$C_{10}$) aminoalkylcarboxy, a substituted or unsubstituted ($C_1$-$C_{10}$) aminoalkylaminocarbonyl, a substituted or unsubstituted ($C_1$-$C_{10}$) aminoalkylcarboxamido, $H_2N$—$HC(Q_5)$-$C(O)$—$O$—, $H_2N$—$HC(Q_5)$-$C(O)$—$N(H)$—, ($C_1$-$C_{10}$) azidoalkyloxy, ($C_1$-$C_{10}$) cyanoalkyloxy, P.G.-HN—$HC(Q_5)$-$C(O)$—$O$—, ($C_1$-$C_{10}$) guanidinoalkyloxy, ($C_1$-$C_{10}$) quaternaryammoniumalkylcarboxy, and ($C_1$-$C_{10}$) guanidinoalkyl carboxy, where $Q_5$ is a side chain of any amino acid (including a side chain of glycine, i.e., H), P.G. is an amino protecting group, and each of $R_5$, $R_8$, $R_9$, $R_{10}$, $R_{13}$, and $R_{14}$ may be independently deleted when one of fused rings A, B, C, or D is unsaturated so as to complete the valency of the carbon atom at that site, or selected from the group consisting of hydrogen, hydroxyl, a substituted or unsubstituted ($C_1$-$C_{10}$) alkyl, ($C_1$-$C_{10}$) hydroxyalkyl, ($C_1$-$C_{10}$) alkyloxy-($C_1$-$C_{10}$) alkyl, a substituted or unsubstituted ($C_1$-$C_{10}$) aminoalkyl, a substituted or unsubstituted aryl, ($C_1$-$C_{10}$) haloalkyl, $C_2$-$C_6$ alkenyl, $C_2$-$C_6$ alkynyl, oxo, a linking group attached to a second steroid, a substituted or unsubstituted ($C_1$-$C_{10}$) aminoalkyloxy, a substituted or unsubstituted ($C_1$-$C_{10}$) aminoalkylcarboxy, a substituted or unsubstituted ($C_1$-$C_{10}$) aminoalkylaminocarbonyl, $H_2N$—$HC(Q_5)$-$C(O)$—$O$—, $H_2N$—$HC(Q_5)$-$C(O)$—$N(H)$—, ($C_1$-$C_{10}$) azidoalkyloxy, ($C_1$-$C_{10}$) cyanoalkyloxy, P.G.-HN—$HC(Q_5)$-$C(O)$—$O$—, ($C_1$-$C_{10}$) guanidinoalkyloxy, and ($C_1$-$C_{10}$) guanidinoalkylcarboxy, where $Q_5$ is a side chain of any amino acid, P.G. is an amino protecting group, provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of a substituted or unsubstituted ($C_1$-$C_{10}$) aminoalkyl, a substituted or unsubstituted ($C_1$-$C_{10}$) aminoalkyloxy, ($C_1$-$C_{10}$) alkylcarboxy-($C_1$-$C_{10}$) alkyl, ($C_1$-$C_{10}$) alkylamino-($C_1$-$C_{10}$) alkylamino, ($C_1$-$C_{10}$) alkylamino-($C_1$-$C_{10}$) alkylamino-($C_1$-$C_{10}$) alkylamino, a substituted or unsubstituted ($C_1$-$C_{10}$) aminoalkylcarboxy, a substituted or unsubstituted arylamino($C_1$-$C_{10}$) alkyl, a substituted or unsubstituted ($C_1$-$C_{10}$) aminoalkyloxy-($C_1$-$C_{10}$) aminoalkylaminocarbonyl, a substituted or unsubstituted ($C_1$-$C_{10}$) aminoalkylaminocarbonyl, a substituted or unsubstituted ($C_1$-$C_5$) aminoalkylcarboxyamido, a ($C_1$-$C_{10}$) quaternaryammonium alkylcarboxy, $H_2N$—$HC(Q_5)$-$C(O)$—$O$—, $H_2N$—$HC(Q_5)$-$C(O)$—$N(H)$—, ($C_1$-$C_{10}$) azidoalkyloxy, cyanoalkyloxy, P.G.-HN—$HC(Q_5)$-$C(O)$—$O$—, ($C_1$-$C_{10}$) guanidinoalkyloxy, a ($C_1$-$C_{10}$) guanidinoalkylcarboxy, or a pharmaceutically acceptable salt thereof.

In Formula (II), at least two or three of $R_3$, $R_7$, or $R_{12}$ may independently include a cationic moiety attached to the Formula (II) structure via a hydrolysable linkage. Optionally, a tail moiety may be attached to Formula (II) at $R_{17}$. The tail moiety may be charged, uncharged, polar, non-polar, hydrophobic, amphipathic, and the like. Although not required, at least two or three of m, n, p, and q are 1. In a preferred embodiment, m, n, and p=1 and q=0. Examples of such structures are shown in FIGS. 1A-1B.

In some embodiments, the compound of Formula (II) or pharmaceutically acceptable salt can be represented by Formula (IIA):

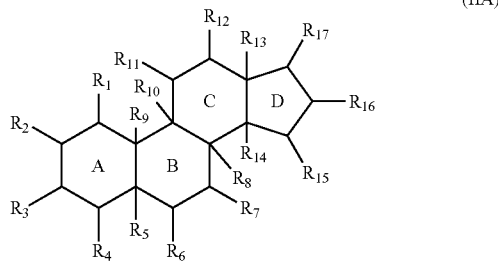

(IIA)

wherein fused rings A, B, C, and D are independently saturated or fully or partially unsaturated; and each of $R_1$ through $R_4$, $R_6$, $R_7$, $R_{11}$, $R_{12}$, $R_{15}$, $R_{16}$, and $R_{17}$ is independently selected from the group consisting of hydrogen, hydroxyl, a substituted or unsubstituted $(C_1-C_{10})$ alkyl, $(C_1-C_{10})$ hydroxyalkyl, $(C_1-C_{10})$ alkyloxy-$(C_1-C_{10})$ alkyl, $(C_1-C_{10})$ alkylcarboxy-$(C_1-C_{10})$ alkyl, $C_1-C_{10})$ alkylamino-$(C_1-C_{10})$ alkyl, $(C_1-C_{10})$ alkylamino-$(C_1-C_{10})$ alkylamino, $(C_1-C_{10})$ alkylamino-$(C_1-C_{10})$ alkylamino-$(C_1-C_{10})$ alkylamino, a substituted or unsubstituted $(C_1-C_{10})$ aminoalkyl, a substituted or unsubstituted aryl, a substituted or unsubstituted arylamino-$(C_1-C_{10})$ alkyl, $(C_1-C_{10})$ haloalkyl, $C_2-C_6$ alkenyl, $C_2-C_6$ alkynyl, oxo, a linking group attached to a second steroid, a substituted or unsubstituted $(C_1-C_{10})$ aminoalkyloxy, a substituted or unsubstituted $(C_1-C_{10})$ aminoalkyloxy-$(C_1-C_{10})$ alkyl, a substituted or unsubstituted $(C_1-C_{10})$ aminoalkylcarboxy, a substituted or unsubstituted $(C_1-C_{10})$ aminoalkylaminocarbonyl, a substituted or unsubstituted $(C_1-C_{10})$ aminoalkylcarboxamido, H2N—HC(Q5)-C(O)—O—, H2N—HC(Q5)-C(O)—N(H)—, $(C_1-C_{10})$ azidoalkyloxy, $(C_1-C_{10})$ cyanoalkyloxy, P.G.-HN—HC(Q5)-C(O)—O—, $(C_1-C_{10})$ guanidinoalkyloxy, $(C_1-C_{10})$ quaternaryammoniumalkylcarboxy, and $(C_1-C_{10})$ guanidinoalkyl carboxy, where Q5 is a side chain of any amino acid (including the side chain of glycine, i.e., H), PG. is an amino protecting group, and $R_5$, $R_8$, $R_9$, $R_{10}$, $R_{13}$, and $R_{14}$ is each independently: deleted when one of fused rings A, B, C, or D is unsaturated so as to complete the valency of the carbon atom at that site, or selected from the group consisting of hydrogen, hydroxyl, 10 a substituted or unsubstituted $(C_1-C_{10})$ alkyl, $(C_1-C_{10})$ hydroxyalkyl, $(C_1-C_{10})$ alkyloxy-$(C_1-C_{10})$ alkyl, a substituted or unsubstituted $(C_1-C_{10})$ aminoalkyl, a substituted or unsubstituted aryl, $C_1-C_{10}$ haloalkyl, $C_2-C_6$ alkenyl, $C_2-C_6$ alkynyl, oxo, a linking group attached to a second steroid, a substituted or unsubstituted $(C_1-C_{10})$ aminoalkyloxy, a substituted or unsubstituted $(C_1-C_{10})$ aminoalkylcarboxy, a substituted or unsubstituted $(C_1-C_{10})$ aminoalkylaminocarbonyl, H2N—HC(Q5)-C(O)—O—, H2N—HC(Q5)-C(O)—N(H)($C_1-C_{10}$) azidoalkyloxy, $(C_1-C_{10})$ cyanoalkyloxy, P.G.-HN—HC(Q5)-C(O)—O—, $(C_1-C_{10})$ guanidinoalkyloxy, and $(C_1-C_{10})$ guanidinoalkylcarboxy, where Q5 is a side chain of any amino acid, PG. is an amino protecting group, and provided that at least two of $R_1$ through $R_{14}$ are independently selected from the group consisting of a substituted or unsubstituted $(C_1-C_{10})$aminoalkyloxy, $(C_1-C_{10})$ alkylcarboxy-$(C_1-C_{10})$ alkyl, $(C_1-C_{10})$ alkylamino-$(C_1-C_{10})$ alkylamino, $(C_1-C_{10})$ alkylamino-$(C_1-C_{10})$ alkylamino-$(C_1-C_{10})$ alkylamino, a substituted or unsubstituted $(C_1-C_{10})$ aminoalkylcarboxy, a substituted or unsubstituted arylamino$(C_1-C_{10})$ alkyl, a substituted or unsubstituted $(C_1-C_{10})$ aminoalkyloxy-$(C_1-C_{10})$ alkyl, a substituted or unsubstituted $(C_1-C_{10})$ aminoalkylaminocarbonyl, $(C_1-C_{10})$ quaternary ammonium alkylcarboxy, H2N—HC(Q5)-C(O)—O—, H2N—HC(Q5)-C(O)—N(H)—, $(C_1-C_{10})$azidoalkyloxy, $(C_1-C_{10})$ cyanoalkyloxy, PG.-HN—HC(Q5)-C(O)—O—, $(C_1-C_{10})$ guanidinoalkyloxy, and $(C_1-C_{10})$ guanidinoalkylcarboxy; or a pharmaceutically acceptable salt thereof.

In some embodiments, compounds comprise a ring system of at least 4 fused rings, where each of the rings has from 5-7 atoms. The ring system has two faces, and contains 3 chains attached to the same face. Each of the chains contains a nitrogen-containing group that is separated from the ring system by at least one atom; the nitrogen-containing group is an amino group, e.g., a primary amino group, or a guanidino group. The compound can also contain a hydrophobic group, such as a substituted $(C_{3-10})$ aminoalkyl group, a $(C_1-C_{10})$ alkyloxy $(C_3-C_{10})$ alkyl group, or a $(C_1-C_{10})$ alkylamino $(C_{3-10})$ alkyl group, attached to the steroid backbone. For example, the compound may have the Formula (V), where each of the three chains containing nitrogen-containing groups is independently selected from $R_1$ through $R_4$, $R_6$, $R_7$, $R_{11}$, $R_{12}$, $R_{15}$, $R_{16}$, $R_{17}$, and $R_{18}$, where: each of fused rings A, B, C, and D is independently saturated, or is fully or partially unsaturated, provided that at least two of A, B, C, and D are saturated, wherein rings A, B, C, and D form a ring system; each of m, n, p, and q is independently 0 or 1; each of $R_1$ through $R_4$, $R_6$, $R_7$, $R_{11}$, $R_{12}$, $R_{15}$, $R_{16}$, $R_{17}$, and $R_{18}$ is independently selected from the group consisting of hydrogen, hydroxyl, a substituted or unsubstituted $(C_1-C_{10})$ alkyl, $(C_1-C_{10})$ hydroxyalkyl, $(C_1-C_{10})$ alkyloxy-$(C_1-C_{10})$ alkyl, $(C_1-C_{10})$alkylcarboxy-$(C_1-C_{10})$ alkyl, $(C_1-C_{10})$ alkylamino-$(C_1-C_{10})$ alkyl, $(C_1-C_{10})$ alkylamino-$(C_1-C_{10})$ alkylamino, alkylamino-$(C_1-C_{10})$ alkylamino-$(C_1-C_{10})$ alkylamino, a substituted or unsubstituted $(C_1-C_{10})$ aminoalkyl, a substituted or unsubstituted aryl, a substituted or unsubstituted arylamino-$(C_1-C_{10})$ alkyl, $(C_1-C_{10})$ haloalkyl, $C_2-C_6$ alkenyl, $C_2-C_6$ alkynyl, oxo, a linking group attached to a second steroid, a substituted or unsubstituted $(C_1-C_{10})$ aminoalkyloxy, a substituted or unsubstituted $(C_1-C_{10})$ aminoalkyloxy-$(C_1-C_{10})$ alkyl, a substituted or unsubstituted $(C_1-C_{10})$ aminoalkylcarboxy, a substituted or unsubstituted $(C_1-C_{10})$ aminoalkylaminocarbonyl, a substituted or unsubstituted $(C_1-C_{10})$ aminoalkylcarboxamido, H2N—HC(Q5)-C(O)—O—, H2N—HC(Q5)-C(0)-N(H)—, $(C_1-C_{10})$ azidoalkyloxy, $(C_1-C_{10})$ cyanoalkyloxy, P.G.-HN—HC(Q_5)-C(0)-0-, $(C_1-C_{10})$ guanidinoalkyloxy, $(C_1-C_{10})$ quaternaryammoniumalkylcarboxy, and $(C_1-C_{10})$ guanidinoalkyl carboxy, where Q5 is a side chain of any amino acid (including a side chain of glycine, i.e., H). PG. is an amino protecting group: and each of $R_5$, $R_8$, $R_9$, $R_{10}$, $R_{13}$, and $R_{14}$ is independently: deleted when one of fused rings A, B, C, or D is unsaturated so as to complete the valency of the carbon atom at that site, or selected from the group consisting of hydrogen, hydroxyl, a substituted or unsubstituted $(C_1-C_{10})$ alkyl, $(C_1-C_{10})$ hydroxyalkyl, $(C_1-C_{10})$ alkyloxy-$(C_1-C_{10})$ alkyl, a substituted or unsubstituted $(C_1-C_{10})$ aminoalkyl, a substituted or unsubstituted aryl, $C_1-C_{10}$ haloalkyl, $C_2-C_6$ alkenyl, $C_2-C_6$ alkynyl, oxo, a linking group attached to a second steroid, a substituted or unsubstituted $(C_1-C_{10})$ aminoalkyloxy, a substituted or unsubstituted $(C_1-C_{10})$ aminoalkylcarboxy, a substituted or unsubstituted $(C_1-C_{10})$ aminoalkylaminocarbonyl, H2N—HC(Q5)-C(0)-O—, H2N—HC(Q5)-C(O)—N(H)—, $(C_1-C_{10})$ azidoalkyloxy, $(C_1-C_{10})$ cyanoalkyloxy, P.G.-HN—HC(Q5)-C(O)—O—, $(C_1-C_{10})$ guanidinoalkyloxy, and (—) guanidinoalkylcarboxy, where Q5 is a side chain of any amino acid, PG. is an amino protecting group, provided that at least three of $R_1$ through $R_4$, $R_6$, $R_7$, $R_{11}$, $R_{12}$, $R_{15}$, $R_{16}$, $R_{17}$, and $R_{18}$ are disposed on the same face of the ring system and are independently selected from the group consisting of a substituted or unsubstituted ($C_1$-$C_{10}$) aminoalkyl, a substituted or unsubstituted ($C_1$-$C_{10}$) aminoalkyloxy, ($C_1$-$C_{10}$) alkylcarboxy-($C_1$-$C_{10}$) alkyl, ($C_1$-$C_{10}$) alkylamino-($C_1$-$C_{10}$) alkylamino, ($C_1$-$C_{10}$) alkylamino-($C_1$-$C_{10}$) alkylamino-($C_1$-$C_{10}$) alkylamino, a substituted or unsubstituted ($C_1$-$C_{10}$) aminoalkylcarboxy, a substituted or unsubstituted arylamino-($C_1$-$C_{10}$) alkyl, a substituted or unsubstituted ($C_1$-$C_{10}$) aminoalkyloxy-($C_1$-$C_{10}$) aminoalkylaminocarbonyl, a substituted or unsubstituted ($C_1$-$C_{10}$) aminoalkylaminocarbonyl, a substituted or unsubstituted ($C_1$-$C_5$) aminoalkylcarboxamido, a ($C_1$-$C_{10}$) quatemaryammoniumalkylcarboxy, H2N—HC(Q5)-C(O)—O—, H2N—HC(Q5)C(O)—N(H)—, ($C_1$-$C_{10}$) azidoalkyloxy, ($C_1$-$C_{10}$) cyanoalkylox, P.G.-HN—HC(Q5)-C(O)—O—, ($C_1$-$C_{10}$) guanidinoalkyloxy, and a ($C_1$-$C_{10}$) guanidinoalkylcarboxy; or a pharmaceutically acceptable salt thereof. In various aspects, at least two, or at least, three, of m, n, p, and q are 1.

In some embodiments, the compounds or pharmaceutically acceptable salts thereof of Formula (I) can be also represented by Formula (IB):

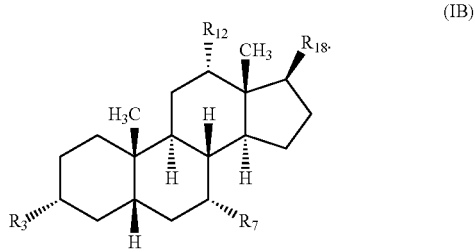

In some embodiments, the compounds or pharmaceutically acceptable salts thereof of Formula (IB) are selected from the group consisting of:

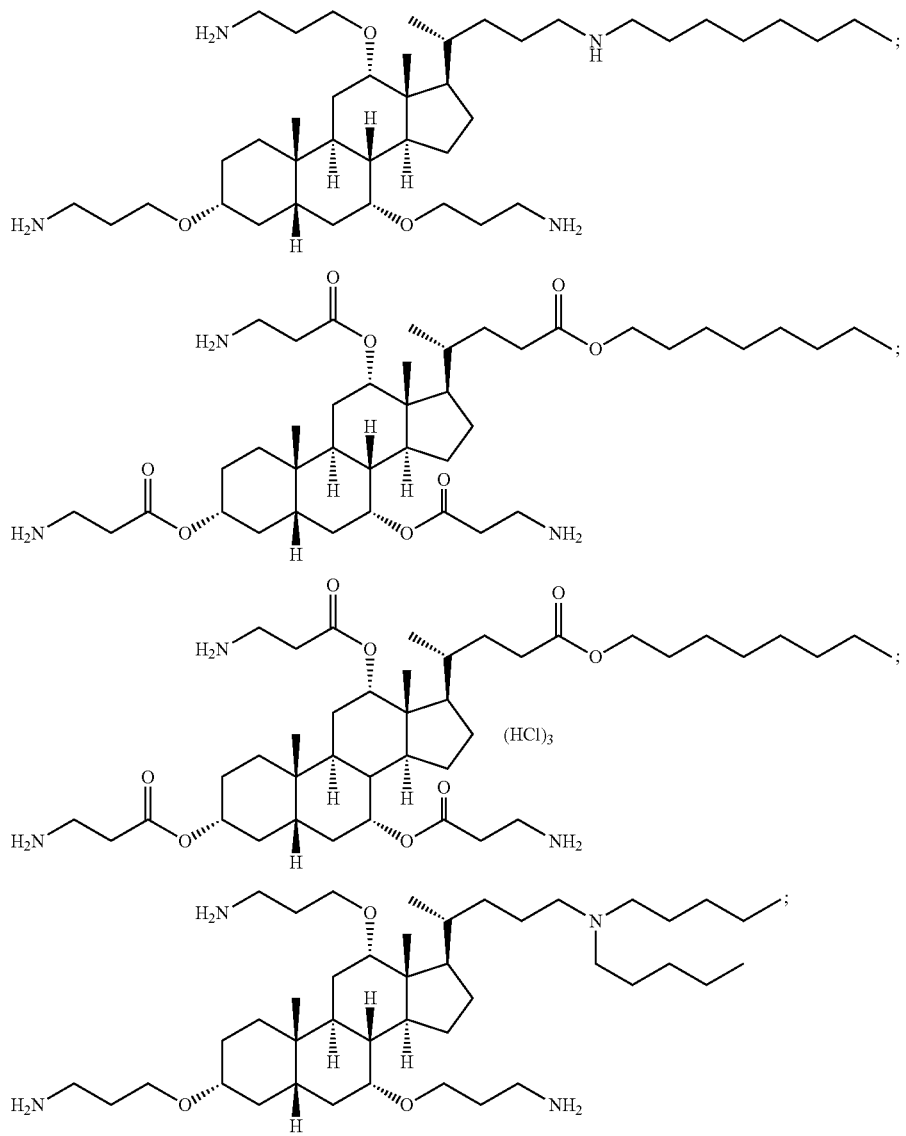

-continued

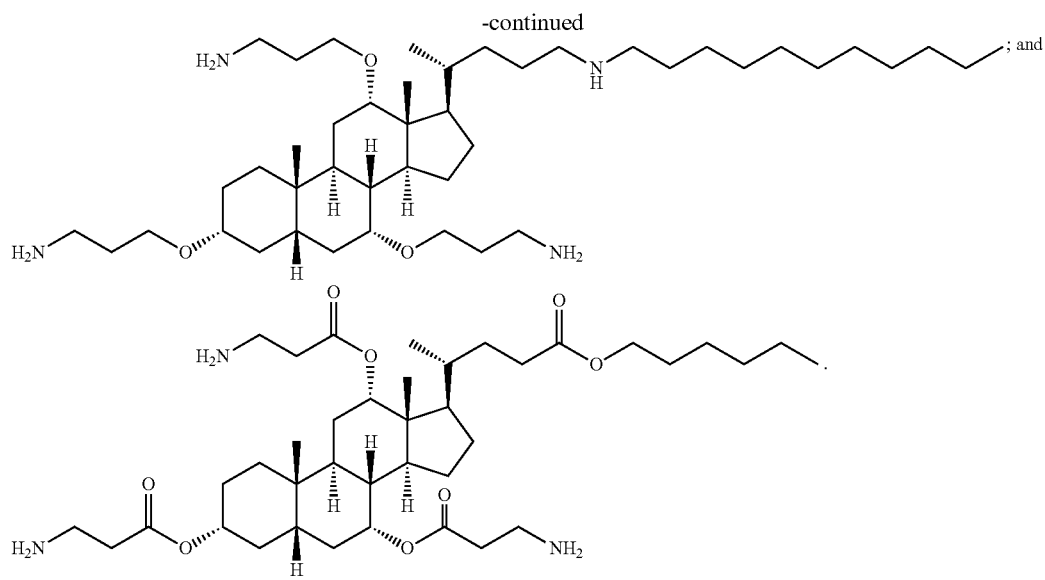

In some embodiments, the compounds or pharmaceutically acceptable salts thereof of Formula (IB) is

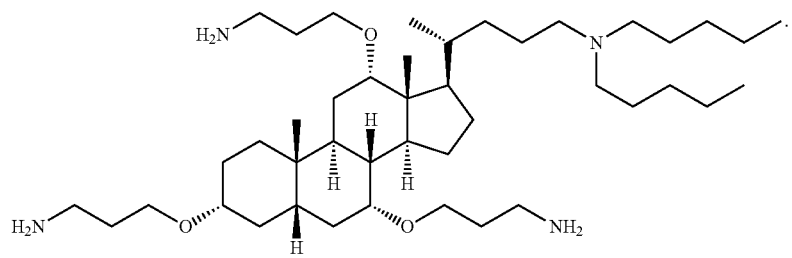

In some embodiments, the pharmaceutically acceptable salt is a hydrochloride salt.

In some embodiments, the pharmaceutically acceptable salt is a tri-hydrochloride salt.

Pharmaceutically Acceptable Salts

The compounds and compositions disclosed herein are optionally prepared as pharmaceutically acceptable salts. The term "pharmaceutically acceptable salt" as used herein is a broad term, and is to be given its ordinary and customary meaning to a skilled artisan (and is not to be limited to a special or customized meaning), and refers without limitation to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, and phosphoric acid. Pharmaceutical salts can also be obtained by reacting a compound with an organic acid such as aliphatic or aromatic carboxylic or sulfonic acids, for example formic acid, acetic acid, propionic acid, glycolic acid, pyruvic acid, malonic acid, maleic acid, fumaric acid, trifluoroacetic acid, benzoic acid, cinnamic acid, mandelic acid, succinic acid, lactic acid, malic acid, tartaric acid, citric acid, ascorbic acid, nicotinic acid, methanesulfonic acid, ethanesulfonic acid, p-toluensulfonic acid, salicylic acid, stearic acid, muconic acid, butyric acid, phenylacetic acid, phenylbutyric acid, valproic acid, 1,2-ethanedisulfonic acid, 2-hydroxyethanesulfonic acid, benzenesulfonic acid, 2-naphthalenesulfonic acid, or naphthalenesulfonic acid. Pharmaceutical salts can also be obtained by reacting a compound with a base to form a salt such as an ammonium salt, an alkali metal salt, such as a lithium, sodium or a potassium salt, an alkaline earth metal salt, such as a calcium, magnesium or aluminum salt, a salt of organic bases such as dicyclohexylamine, N-methyl-D-glucamine, tris(hydroxymethyl)methylamine, $C_1$-$C_7$ alkylamine, cyclohexylamine, dicyclohexylamine, triethanolamine, ethylenediamine, ethanolamine, diethanolamine, triethanolamine, tromethamine, and salts with amino acids such as arginine and lysine; or a salt of an inorganic base, such as aluminum hydroxide, calcium hydroxide, potassium hydroxide, sodium carbonate, sodium hydroxide, or the like.

Pharmaceutical Compositions

While it is possible for the compounds described herein to be administered alone, it may be preferable to formulate the compounds as pharmaceutical compositions. As such, in yet another aspect, pharmaceutical compositions useful in the methods and uses of the disclosed embodiments are provided. More particularly, the pharmaceutical compositions described herein may be useful, inter alia, for treating or preventing mastitis. A pharmaceutical composition is any composition that may be administered to a subject in order to treat or ameliorate a condition. In some embodiments, the pharmaceutical composition is for veterinary use. The subject receiving the treatment may be a mammal. The mammal is preferably a diary cow but may also be pigs, sheep, goats, horses, camels, buffalo, cats, dogs, rats, mice, and humans.

As used herein the terms "pharmaceutically acceptable" and "physiologically acceptable" mean a biologically compatible formulation, gaseous, liquid or solid, or mixture thereof, which is suitable for one or more routes of administration, in vivo delivery, or contact. A formulation is compatible in that it does not destroy activity of an active ingredient therein (e.g., a CSA), or induce adverse side effects that far outweigh any prophylactic or therapeutic effect or benefit.

In an embodiment, the pharmaceutical compositions may be formulated with pharmaceutically acceptable excipients such as carriers, solvents, stabilizers, adjuvants, diluents, etc., depending upon the particular mode of administration and dosage form. The pharmaceutical compositions should generally be formulated to achieve a physiologically compatible pH, and may range from a pH of about 3 to a pH of about 11, preferably about pH 3 to about pH 7, depending on the formulation and route of administration. In alternative embodiments, it may be preferred that the pH is adjusted to a range from about pH 5.0 to about pH 8. More particularly, the pharmaceutical compositions may comprise a therapeutically or prophylactically effective amount of at least one compound as described herein, together with one or more pharmaceutically acceptable excipients. Optionally, the pharmaceutical compositions may comprise a combination of the compounds described herein, or may include a second active ingredient useful in the treatment or prevention of bacterial infection (e.g., anti-bacterial or anti-microbial agents).

Formulations, e.g., for parenteral or oral administration, are most typically solids, liquid solutions, emulsions or suspensions, while inhalable formulations for pulmonary administration are generally liquids or powders, with powder formulations being generally preferred. A preferred pharmaceutical composition may also be formulated as a lyophilized solid that is reconstituted with a physiologically compatible solvent prior to administration. Alternative pharmaceutical compositions may be formulated as syrups, creams, ointments, tablets, and the like.

The term "pharmaceutically acceptable excipient" refers to an excipient for administration of a pharmaceutical agent, such as the compounds described herein. The term refers to any pharmaceutical excipient that may be administered without undue toxicity.

Pharmaceutically acceptable excipients are determined in part by the particular composition being administered, as well as by the particular method used to administer the composition. Accordingly, there exists a wide variety of suitable formulations of pharmaceutical compositions (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants such as ascorbic acid; chelating agents such as EDTA; carbohydrates such as dextrin, hydroxyalkylcellulose, hydroxyalkylmethylcellulose, stearic acid; liquids such as oils, water, saline, glycerol and ethanol; wetting or emulsifying agents; pH buffering substances; and the like. Liposomes are also included within the definition of pharmaceutically acceptable excipients.

The pharmaceutical compositions described herein may be formulated in any form suitable for the intended method of administration. When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as cross-linked povidone, maize starch, or alginic acid; binding agents, such as povidone, starch, gelatin or acacia; and lubricating agents, such as magnesium stearate, stearic acid or talc.

Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, pharmaceutical compositions may be formulated as suspensions comprising a compound of the embodiments in admixture with at least one pharmaceutically acceptable excipient suitable for the manufacture of a suspension.

In yet another embodiment, pharmaceutical compositions may be formulated as dispersible powders and granules suitable for preparation of a suspension by the addition of suitable excipients.

Excipients suitable for use in connection with suspensions include suspending agents, such as sodium carboxymethylcellulose, methylcellulose, hydroxypropyl methylcellulose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); polysaccharides and polysaccharide-like compounds (e.g. dextran sulfate); glycoaminoglycans and glycosaminoglycan-like compounds (e.g., hyaluronic acid); and thickening agents, such as carbomer, beeswax, hard paraffin or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical compositions may also be in the form of oil-in water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions may be in the form of a sterile injectable preparation, such as a sterile injectable aqueous emulsion or oleaginous suspension. This emulsion or suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,2-propanediol (propylene glycol).

The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or diglycerides. In addition, fatty acids such as oleic acid may likewise be used in the preparation of injectables.

To obtain a stable water-soluble dose form of a pharmaceutical composition, a pharmaceutically acceptable salt of a compound described herein may be dissolved in an aqueous solution of an organic or inorganic acid, such as 0.3 M solution of succinic acid, or more preferably, citric acid. if a soluble salt form is not available, the compound may be dissolved in a suitable co-solvent or combination of co-solvents. Examples of suitable co-solvents include alcohol, propylene glycol, polyethylene glycol 300, polysorbate 80, glycerin and the like in concentrations ranging from about 0 to about 60% of the total volume. In one embodiment, the active compound is dissolved in DMSO and diluted with water.

The pharmaceutical composition may also be in the form of a solution of a salt form of the active ingredient in an appropriate aqueous vehicle, such as water or isotonic saline or dextrose solution. Also contemplated are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In one embodiment, the compounds described herein may be formulated for oral administration in a lipid-based formulation suitable for low solubility compounds. Lipid-based formulations can generally enhance the oral bioavailability of such compounds.

As such, a pharmaceutical composition comprises a therapeutically or prophylactically effective amount of a compound described herein, together with at least one pharmaceutically acceptable excipient selected from the group consisting of-medium chain fatty acids or propylene glycol esters thereof (e.g., propylene glycol esters of edible fatty acids such as caprylic and capric fatty acids) and pharmaceutically acceptable surfactants such as polyoxyl 40 hydrogenated castor oil.

In an alternative preferred embodiment, cyclodextrins may be added as aqueous solubility enhancers. Preferred cyclodextrins include hydroxypropyl, hydroxyethyl, glucosyl, maltosyl and maltotriosyl derivatives of α-, β-, and γ-cyclodextrin. A particularly preferred cyclodextrin solubility enhancer is hydroxypropyl-o-cyclodextrin (BPBC), which may be added to any of the above-described compositions to further improve the aqueous solubility characteristics of the compounds of the embodiments. In one embodiment, the composition comprises about 0.1% to about 20% hydroxypropyl-o-cyclodextrin, more preferably about 1% to about 15% hydroxypropyl-o-cyclodextrin, and even more preferably from about 2.5% to about 10% hydroxypropyl-o-cyclodextrin. The amount of solubility enhancer employed will depend on the amount of the compound of the embodiments in the composition.

In some exemplary embodiments, a CSA comprises a multimer (e.g., a dimer, trimer, tetramer, or higher order polymer). In some exemplary embodiments, the CSAs can be incorporated into pharmaceutical compositions or formulations. Such pharmaceutical compositions/formulations are useful for administration to a subject, in vivo or ex vivo. Pharmaceutical compositions and formulations include carriers or excipients for administration to a subject.

Such formulations include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone.

A pharmaceutical composition contains a total amount of the active ingredient(s) sufficient to achieve an intended therapeutic effect.

Methods and Uses:

Disclosed herein are compositions comprising at least one cationic steroid antimicrobial (CSA), or a pharmaceutically acceptable sat thereof, for use in the treatment of mastitis. Some embodiments are methods of preventing or inhibiting mastitis in a subject in need of treatment for mastitis, where the mammal has a clinical case or a subclinical case of mastitis. The method includes identifying a subject in need of treatment or prevention of mastitis and administering at least one CSA formulation. Examples of subjects in need of prevention of mastitis are dairy cows that are lactating and have clinical mastitis. A dairy cow with clinical mastitis may be separated from a herd for treatment or may be treated while producing milk for consumption. Since the CSA formulations are effective without an anti-biotic, the treatments described herein can be used without contaminating the milk with anti-biotic. This allows the dairy cow to be treated without the loss of production associated with many other forms of mastitis treatment.

In an example, the dairy cow can be lactating and have a somatic cell count (SCC) less than or equal to 500,000 cells/mL at the time of administering the CSA formulation. Alternatively, the dairy cow can be lactating and have a somatic cell count (SCC) greater than 500,000 cells/mL at the time of administering the CSA formulation. In some cases, the dairy cow can be taken out of production during the administration of the CSA formulation, e.g., for a period of time of about 3 days or less, 2 days or less, or 1 day or less.

The CSA compositions can also be administered to lactating subclinical animals (i.e., mammals with below clinical numbers of somatic cells). In this embodiment, the CSA composition is used to prevent clinical mastitis. Because the CSA compounds can be used without affecting milk production, while not contaminating the milk with antibiotic, the CSA compositions are useful for preventative treatments of mastitis.

In some embodiments, the CSA compositions can be administered to non-lactating or "dry" subjects. The mammary organ of a mammal can become infected with mastitis causing bacteria prior to lactating. Administering the CSA compound to the subject before lactation commences can prevent mastitis at the onset of lactation.

The compositions disclosed herein can be administered intra-mammary in any way suitable for delivering a therapeutic amount of the compound. The compounds can be administered by injection, orally, topically or by other suitable method. In some embodiments the CSA formulation is injected intra-mammary. For example, injections can be carried out using a syringe. The injections may be performed through the teat of the mammary organ. For treating clinical mastitis, injections can be beneficial because of the high dosage that can be applied locally to the affected area. In some embodiments, the CSA formulation can be administered as a teat dip in which the teat is coated with the CSA formulation. Teat dip is particularly suited for preventative measures and can be used on clinical or subclinical animals and/or lactating or non-lactating animals.

One of ordinary skill in the art to which these exemplary embodiments belong will understand that the compositions may be administered in numerous ways. For example, typical administration is by injecting a CSA formulation directly into the mammary organ of the subject (e.g., the udder of a cow). However, other routes of administration can also be performed so long as the compound is delivered intra-mammary in the effective concentrations for treating the mastitis. In some exemplary embodiments, administration may be intravenous, oral, or topical.

The delivery forms can be homogeneous, e.g., forms in which the composition is in solution, or heterogeneous, e.g., forms in which the composition is contained within liposomes or microspheres. The forms can produce an immediate effect, and can alternatively, or additionally, produce an extended effect. For example, liposomes, or microspheres, or other similar means of providing an extended release of the composition, can be used to extend the period during which the composition is exposed to the targeted area; non-encapsulated compositions can also be provided for an immediate effect.

Dosages

The formulations may, for convenience, be prepared or provided as a unit dosage form. Preparation techniques include bringing into association the active ingredient (e.g., CSA) and a pharmaceutical carrier(s) or excipient(s). In general, formulations are prepared by uniformly and intimately associating the active ingredient with liquid carriers or finely divided solid carriers or both, and then, if necessary, shaping the product. For example, a tablet may be made by compression or molding. Compressed tablets may be prepared by compressing, in a suitable machine, an active ingredient (e.g., a CSA) in a free-flowing form such as a powder or granules, optionally mixed with a binder, lubricant, inert diluent, preservative, surface-active or dispersing agent. Molded tablets may be produced by molding, in a suitable apparatus, a mixture of powdered compound (e.g., CSA) moistened with an inert liquid diluent. The tablets may optionally be coated or scored and may be formulated so as to provide a slow or controlled release of the active ingredient therein.

Compounds (e.g., CSAs), including pharmaceutical formulations can be packaged in unit dosage forms for ease of administration and uniformity of dosage. A "unit dosage form" as used herein refers to a physically discrete unit suited as unitary dosages for the subject to be treated; each unit containing a predetermined quantity of compound optionally in association with a pharmaceutical carrier (excipient, diluent, vehicle or filling agent) which, when administered in one or more doses, is calculated to produce a desired effect (e.g., prophylactic or therapeutic effect or benefit). Unit dosage forms can contain a daily dose or unit, daily sub-dose, or an appropriate fraction thereof, of an administered compound (e.g., CSA). Unit dosage forms also include, for example, capsules, troches, cachets, lozenges, tablets, ampules and vials, which may include a composition in a freeze-dried or lyophilized state; a sterile liquid carrier, for example, can be added prior to administration or delivery in vivo. Unit dosage forms additionally include, for example, ampules and vials with liquid compositions disposed therein. Unit dosage forms further include compounds for transdermal administration, such as "patches" that contact with the epidermis of the subject for an extended or brief period of time. The individual unit dosage forms can be included in multi-dose kits or containers. Pharmaceutical formulations can be packaged in single or multiple unit dosage forms for ease of administration and uniformity of dosage.

Compounds (e.g., CSAs) can be administered in accordance with the methods at any frequency as a single bolus or multiple dose e.g., one, two, three, four, five, or more times hourly, daily, weekly, monthly, or annually or between about 1 to 10 days, weeks, months, or for as long as appropriate. Exemplary frequencies are typically from 1-7 times, 1-5 times, 1-3 times, 2-times or once, daily, weekly or monthly. Timing of contact, administration ex vivo or in vivo delivery can be dictated by the infection, pathogenesis, symptom, pathology or adverse side effect to be treated. For example, an amount can be administered to the subject substantially contemporaneously with, or within about 1-60 minutes or hours of the onset of a symptom or adverse side effect, pathogenesis, or vaccination. Long-acting pharmaceutical compositions may be administered twice a day, once a day, once every two days, three times a week, twice a week, every 3 to 4 days, or every week depending on half-life and clearance rate of the particular formulation. For example, in an embodiment, a pharmaceutical composition contains an amount of a compound as described herein that is selected for administration to a patient on a schedule selected from: twice a day, once a day, once every two days, three times a week, twice a week, and once a week.

Doses may vary depending upon whether the treatment is therapeutic or prophylactic, the onset, progression, severity, frequency, duration, probability of or susceptibility of the symptom, the type pathogenesis to which treatment is directed, clinical endpoint desired, previous, simultaneous or subsequent treatments, general health, age, gender or race of the subject, bioavailability, potential adverse systemic, regional or local side effects, the presence of other disorders or diseases in the subject, and other factors that will be appreciated by the skilled artisan (e.g., medical or familial history). Dose amount, frequency or duration may be increased or reduced, as indicated by the clinical outcome desired, status of the infection, symptom or pathology, any adverse side effects of the treatment or therapy. The skilled artisan will appreciate the factors that may influence the dosage, frequency and timing required to provide an amount sufficient or effective for providing a prophylactic or therapeutic effect or benefit. The exact dosage will be determined by the practitioner, in light of factors related to the subject that requires treatment. Dosage and administration are adjusted to provide sufficient levels of the active agent(s) or to maintain the desired effect. It will be appreciated that treatment as described herein includes preventing a disease, ameliorating symptoms, slowing disease progression, reversing damage, or curing a disease.

The dosage may range broadly, depending upon the desired effects, the therapeutic indication, and the mode of administration. Alternatively dosages may be based and calculated upon the surface area of the patient, as understood by those of skill in the art. Although the exact dosage will be determined on a drug-by-drug basis, some generalizations regarding the dosage can be made. In some embodiments, the dosage regimen for local or systemic delivery (based on the weight of the subject) may be about 1 µg/g, 5 µg/g, 10 µg/g, 50 µg/g, 100 µg/g, 200 µg/g, 500 µg/g, 750 µg/g, 1000 µg/g, or less than any of the aforementioned numbers, or a range bounded by any two of the aforementioned numbers. In some embodiments, between about 0.001 mg to about 3000 mg of the active ingredient is delivered is administered locally or systemically. In some embodiments, about 5-15 mg of active ingredient is administered locally or systemically. In other embodiments, about 0.001 mg, 0.01 mg, 0.1 mg, 1 mg, 5 mg, 10 mg, 15 mg, 25 mg, 50 mg, 100 mg, 500 mg, 1000 mg, or less than any of the aforementioned numbers, or a range bounded by any two of the aforementioned numbers is administered locally or systemically. The dosage may be a single one or a series of two or more given in the course of one or more days, as is needed by the subject. In some embodiments, the compounds will be administered for a period of continuous therapy, for example for a week or more, or for months or years.

In instances where animal and/or human dosages for different compounds having been established for at least some condition, those same dosages may be used, or dosages that are between about 0.1% and 500%, more preferably between about 25% and 250% of the established animal and/or human dosage. For examples, dosages for INFUSE® BMP-2 and/or OP-1 BMP-7 are known and can be used to infer dosages for use in the disclosed embodiments. Where no animal and/or human dosage is established, as will be the case for newly-discovered pharmaceutical compositions, a suitable animal and/or human dosage can be inferred from ED50 or ID50 values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or conditions.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

As described herein, the methods of the embodiments also include the use of a compound or compounds as described herein together with one or more additional therapeutic agents for the treatment of disease conditions. Thus, for example, the combination of active ingredients may be: (1) co-formulated and administered or delivered simultaneously in a combined formulation; (2) delivered by alternation or in parallel as separate formulations; or (3) by any other combination therapy regimen known in the art. When delivered in alternation therapy, the methods described herein may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

Kits

Other embodiments include kits comprising CSA compositions and instructions on disclosed methods. In some embodiments, kits include compounds (e.g., CSA), combination compositions and pharmaceutical compositions/formulations thereof, packaged into a suitable packaging material. In one embodiment, a kit includes packaging material, a CSA, and instructions. In various aspects, the instructions are for administering the CSA to: provide a subject with treatment or protection against mastitis; treat a subject for mastitis; decrease susceptibility of a subject to a pathogenesis; or decrease or prevent an adverse side effect caused by a pathogenesis.

The term "packaging material" refers to a physical structure housing one or more components of the kit. The packaging material can maintain the components sterilely, and can be made of material commonly used for such purposes (e.g., paper, corrugated fiber, glass, plastic, foil, ampules, vials, tubes, etc.). A kit can contain a plurality of components, e.g., two or more compounds alone or in combination with growth factors, optionally sterile.

A kit optionally includes a label or insert including a description of the components (type, amounts, doses, etc.), instructions for use in vitro, in vivo, or ex vivo, and any other components therein. Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a disk (e.g., floppy diskette, hard disk, ZIP disk), optical disk such as CD- or DVD-ROM/RAM, DVD, MP3, magnetic tape, or an electrical storage media such as RAM and ROM or hybrids of these such as magnetic/optical storage media, FLASH media or memory type cards.

Disagglomeration of CSA Particles

The CSA compounds disclosed herein may sometimes form agglomerates or particles that are micron-sized or larger, particularly if they are not easily solubilized in the carrier used to form liquid compositions, such as compositions that are injectable or suitable for topical application. When the CSA compounds form agglomerates, their surface area and associated chemical activity is reduced. For example, in agglomerates that are 10 microns in size, a majority of the CSA molecules are contained in the interior of the particulate and are therefore not bioactive or available. Only the CSA molecules on the surface of the agglomerates are able to interact with an kill microbes.

According to one embodiment, the CSA compound can be mixed with one or more disagglomeration agents, such as a dispersant, surfactant or thickening agent, prior to being mixed into the main solvent or liquid carrier to prevent or reduce agglomeration of the CSA molecules. Instead, the CSA molecules can remain largely non-agglomerated, or least form smaller agglomerates, such as nano-sized agglomerates of increased surface area. Preventing or reducing agglomeration greatly increases surface area and reactivity of the CSA compound.

It has also been found that the order of mixing affects the propensity of the CSA molecules to form agglomerates. If the disagglomeration agent is mixed with a composition that already contains a liquid carrier and CSA agglomerates, disagglomeration is difficult. However, if the disagglomeration agent is first mixed with the CSA compound to form an intermediate mixture which is then mixed or dispersed into a liquid carrier, formation of agglomerates is greatly reduced or eliminated.

Examples of disagglomeration agents include, but are not limited to, modified celluloses, modified surfactants, modified non-oxidizing vehicles, and organic acids. More specific examples include modified nonionic hydroxyethyl cellulose, natural polyoxyethylene sorbitol ester, hydroxyethyl cellulose, 2-hydroxyethyl cellulose with molecular weights between 90,000 and 750,000 with a viscosity between 50-500 cps in solutions between 1% and 5% water at temperatures between 20° C. and 25° C., modified aqueous solutions of polysorbate nonionic surfactants, polyoxyethylene sorbitan mono-, di-, and tri-($C_{12}$-$C_{18}$)-alkanoates, polyoxyethylene (20) sorbitan trioleate sold under the tradename TWEEN™ 85, polyoxyethylene(20) sorbitan monoolcate sold under the tradename TWEEN™ 80, polyoxy-ethylene(20) sorbitan monostearate sold under the tradename TWEEN™60, polyoxyethyl-ene (20) sorbitan monopalmitate sold under the tradename TWEEN™ 40, and polyoxyethyl-ene(20) sorbitan monolaurate sold under the tradename TWEEN™ 20, hydroxymethyl cellulose, cellulose, methylcellulose, hydroxypropyl cellulose, methyl cellulose, carboxy methylcellulose, emulsifying waxes, alkyl triammonium methosulfate, ceteraryloctanoate, polyols, polyalkylene glycols having alkylene moieties containing about 2-3 carbon atoms, and polyethylene glycols.

EXAMPLES

Example 1

Effectiveness

CSA-44/Propylene Glycol Formulation

A first dose characterization study was conducted using CSA-44 hydrochloride with and without propylene glycol based in the formulation. This study enabled the selection of a dose to be used in a dose confirmation (field) study, which was conducted using two propylene glycol formulations and 60 mg of CSA-44 hydrochloride per 10 ml syringe.

The objective of this study was to evaluate the effectiveness of intramammary administered CSA-44, with and without propylene glycol as part of the formulation, for the treatment of clinical mastitis in lactating dairy cows.

A total of 42 cow quarters from Blue Star Dairy (BSD) were enrolled. Cows in their second or greater lactation, with an elevated somatic cell count (SCC) and either a positive milk culture for a mastitis pathogen or signs of clinical mastitis were assigned to one of two treatment groups: 1) ceftiofur hydrochloride administered 2-7 times, per label directions; and 2) 60 mg of CSA-44 per quarter, cows were infused eight to ten times at a 12-hour interval. A quarter was considered cured if there were no clinical signs of mastitis 10 days post-treatment, milk was visibly normal, and somatic cell count (SCC) was less than 350,000 cells. Using these criteria, cure rates for Group CSA treated cows were 87% for Staph. spp. (CNS and *Staph. aureus*), 90% for *Escherichia coli*, and 78% for Strep spp. (*Streptococcus dysgalactiae, Strep. uberis*, and *Streptococcus* sp).

Analysis of susceptibility results of concentration-dependent antimicrobial activity and time-kill analysis data from previous studies documented the antimicrobial activity of ceragenins (CSA formulations). Based on the results generated, defining clinical cure as a return to normal milk quality and SCC less than 350,000 10 days post-treatment, the optimal dosage of CSA-44 was postulated to be 120 mg of CSA-44. A dosage of 120 mg of CSA-44 (provided as CSA-44 HCl in a propylene glycol vehicle) per 10 mL syringe was administered three times by intramammary infusion at a 24-hour interval.

CSA-44/Saline Formulation

A second dose characterization study was conducted using a non-final (saline) formulation of CSA-44 hydrochloride. The study enabled the selection of a dose to be used in the dose confirmation (field) study, which was conducted using the saline formulation of CSA-44 hydrochloride.

The objective of this study was to evaluate the effectiveness of intramammary administered CSA-44, as a saline based formulation, for the treatment of clinical mastitis in lactating dairy cows.

The objective was to evaluate the effectiveness of intramammary infusion of CSA-44 hydrochloride sterile suspension three times at a 24-hour interval at 120.0 mg dosage in the affected quarter in comparison to a negative control or 200 mg of cephapirin sodium activity in a stable peanut oil gel for the treatment of clinical mastitis in lactating dairy cattle.

A total of 151 cows from 2 herds were enrolled. Cows were enrolled in the study when they had visually abnormal milk (clots, flakes, or watery secretion) or if udder swelling, heat, pain or redness were present and milk was not yet visually abnormal, but the California Mastitis Test (CMT) gave results of 2 or greater. A pre-treatment milk sample was obtained from each affected quarter(s) and cultured for the presence of organisms associated with mastitis; the culture data were not available prior to treatment assignments.

Cows were assigned in blocks of three to receive either 120 mg CSA-44 HCl, 200 mg cephapirin sodium, or no treatment. Enrollment was restricted to cows with one quarter affected with clinical mastitis.

CSA-44 (120 mg) or cephapirin sodium (200 mg) was administered as an intramammary infusion three times or two times, respectively, at a 24-hour interval beginning on the day of enrollment (Day 0). Cows assigned to the control group were left untreated. A total of 151 cows from 2 herds were enrolled. Cows in their second or greater lactation, with an elevated somatic cell count (SCC) and either a positive milk culture for a mastitis pathogen or signs of clinical mastitis were assigned to one of three treatment groups. A quarter was considered cured if there were no clinical signs of mastitis, visibly normal milk, and a negative milk culture 11 days post-treatment. Using these criteria, cure rates for all mastitis cases were 28.0% (Control-0 mg), 63.0% (cephapirin sodium, 200 mg), and 75.0% (CSA-44, 120 mg).

Figure 2A:
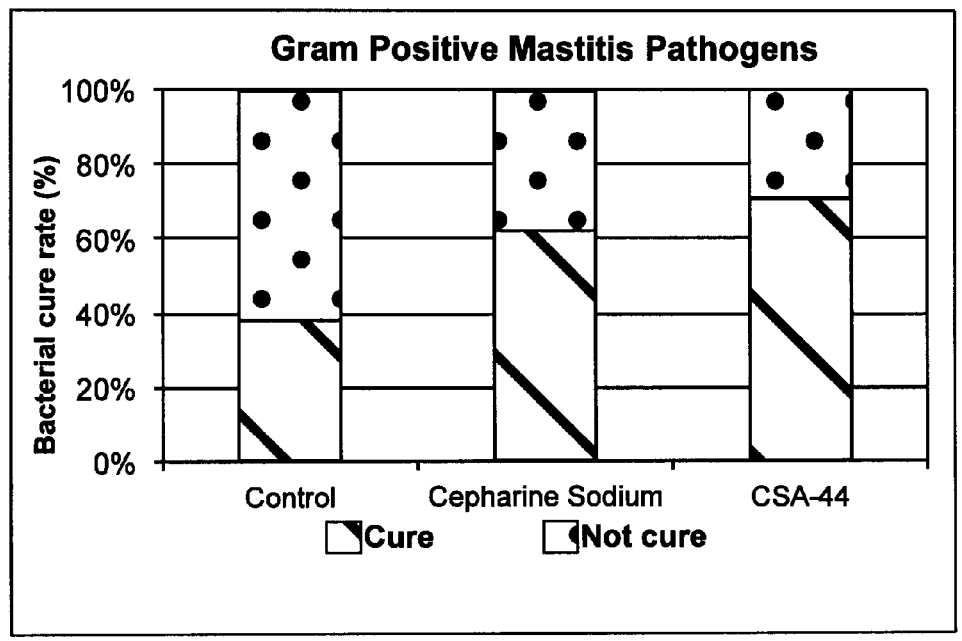
FIG. 2A is a graph that illustrates and compares cure rates for clinical mastitis caused by gram positive bacteria in lactating dairy cattle when untreated (control), when treated with cepharine sodium, and when treated with CSA-44.

Test data for gram positive bacteria are set forth in Table 1 below and graphically illustrated in FIG. 2A.

TABLE 1

| Administered Drug | Gram Positive | | |
|---|---|---|---|
| | Cure (number) | Not Cure (number) | % Cure |
| Control | 8 | 13 | 38 |
| Cephapirin Sodium | 21 | 13 | 62 |
| CSA-44 | 29 | 12 | 70 |

Figure 2B:
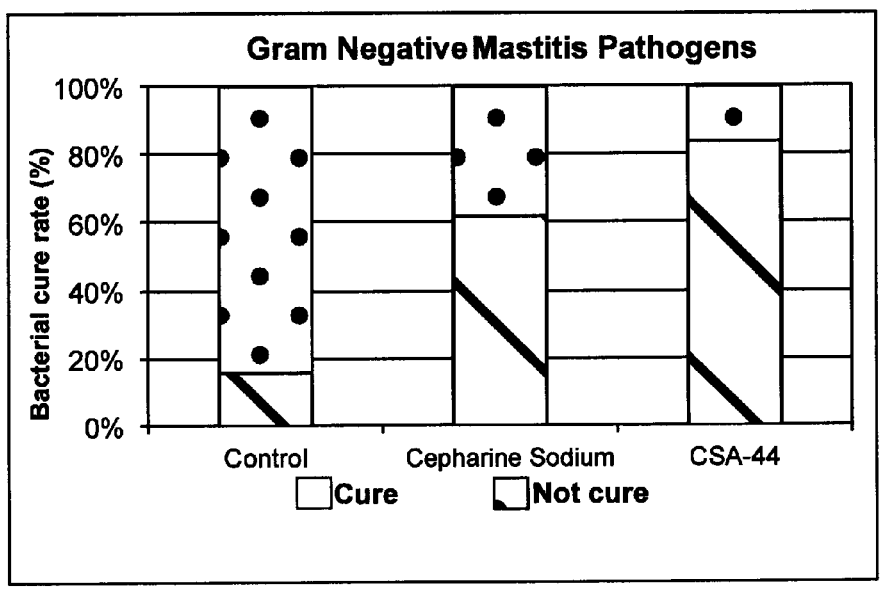
FIG. 2B is a graph that illustrates and compares cure rates for clinical mastitis caused by gram negative bacteria in lactating dairy cattle when untreated (control), when treated with cepharine sodium, and when treated with CSA-44.

Test data for gram negative bacteria are set forth in Table 2 below and graphically illustrated in FIG. 2B.

TABLE 2

| Administered Drug | Gram Negative | | |
|---|---|---|---|
| | Cure (number) | Not Cure (number) | % Cure |
| Control | 3 | 15 | 17 |
| Cephapirin Sodium | 11 | 7 | 61 |
| CSA-44 | 16 | 3 | 84 |

Figure 2C:
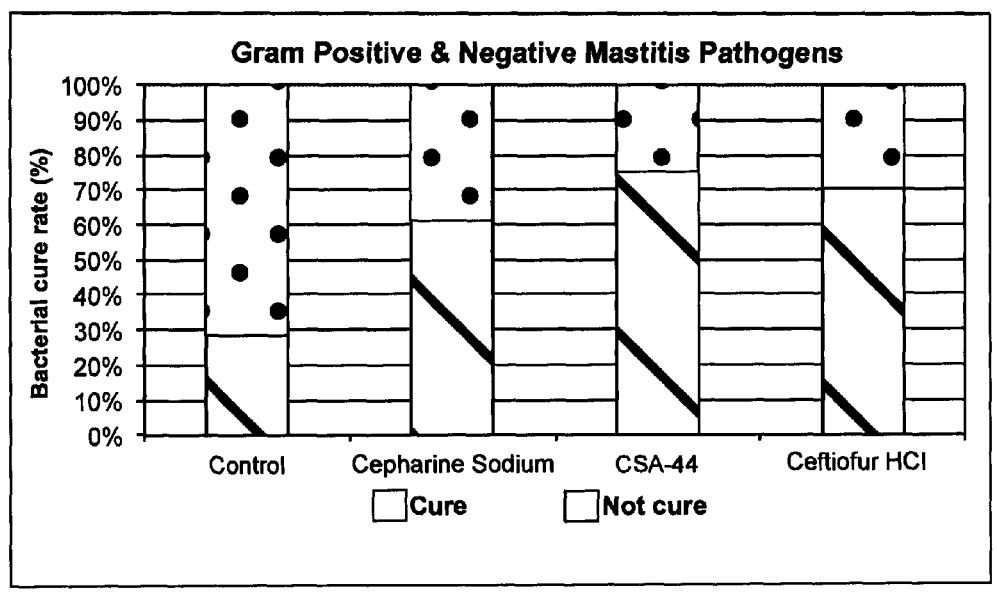
FIG. 2C is a graph that illustrates and compares cure rates for clinical mastitis caused by gram positive and negative bacteria in lactating dairy cattle when untreated (control), when treated with cepharine sodium, when treated with CSA-44, and when treated with ceftiofur HCl.

Test data for combined gram positive and gram negative bacteria are set forth in Table 3 below and graphically illustrated in FIG. 2C.

TABLE 3

| Administered Drug | Gram Positive | | |
|---|---|---|---|
| | Cure (number) | Not Cure (number) | % Cure |
| Control | 11 | 28 | 28 |
| Cephapirin Sodium | 32 | 20 | 62 |
| CSA-44 | 45 | 15 | 75 |
| Ceftiofur HCl* | 38 | 16 | 70 |

*Freedom Of Information Summary, Original New Animal Drug Application NADA 141-238: sterile suspension of ceftiofur hydrochloride. "For the treatment of clinical mastitis in lactating dairy cattle associated with coagulase-negative *staphylococci*, *Streptococcus dysgalactae*, and *Eshcherica coli*."

Based on the results of this is pre-NADA clinical trial and previous preliminary data, a dosage of 60 and 120 mg of CSA-44 (provided as CSA-44 HCl in saline and or nonionic polymer and cellulose preparation per 10 mL syringe administered three times by intramammary infusion at a 24-hour interval was selected as the dosage regimen for further testing.

Example 2

Animal Safety

The purpose of this example was to study the effects on dairy cows relative to udder irritation of intramammary infusion of a sterile formulation of CSA-44 containing either 60 mg or 120 mg of CSA-44 per 10 mL plastet into both front quarters. More particularly, the study evaluated the safety of intramammary infusion of 120 mg, 150 mg and 200 mg CSA-44 hydrochloride sterile saline (0.9% NaCl) suspension, respectively, in each of two front quarters daily for three consecutive days with an approximate 24-hour interval between infusions.

Three lactating female Holstein dairy cattle ranging from 2 to 5 years of age and representing low milk producers (13.2 kg to 24.0 kg/day) and high milk producers (25.0 kg to 31.9 kg/day) were used in the study. Cows were enrolled based on the absence of mastitis pathogens, absence of clinical mastitis (normal strip cup and udder palpation), a somatic cell count (SCC) less than or equal to 200,000 per mL, and no edema or teat lesions.

Within each of the lactation/production subgroups (1st lactation high producers, 1st lactation low producers, ≥2nd lactation high producers, or ≥2nd lactation low producers), cows were assigned to receive either three doses of CSA-44 by intramammary infusion. There were no non-treated controls.

Following a 3-day pre-treatment clinical observation and milk sample collection period, animals received their assigned treatment. Measurements and observations continued during the treatment period and through Day 3 (60 hours) post treatment.

A CSA-44 sterile saline suspension (120 mg, 150 mg, or 200 mg) was administered as an intramammary infusion into both front quarters once at a 24-hour interval for three consecutive days. The following clinical and production measures were evaluated for a total of either 14 milkings: appearance of foremilk (strip cup evaluation), physical condition of udder, milk production, and general health.

The results of the study were as follows. Individual udder palpation and strip cup scores were normal during the 3-day pre-treatment period. None of the animals in either the three doses group showed any abnormality in their general health during the pre-treatment period.

The milk quality appearance and strip cup response for all dosages during treatment showed no change in milk quality following intramammary infusion. There were no overall differences in udder physical condition scores, strip cup analyses, or milk production (milk weight and percent milk fat) in response to treatment with three doses of CSA-44.

These data support the conclusion that the sterile saline formulation containing 120 mg, 150 mg or 200 mg CSA-44 per 10 mL dose is clinically safe and not irritating to the mammary tissue of lactating dairy cattle when infused once daily for up to three consecutive days.

Example 3

Human Food Safety

The objective of this study was to validate a method for the determination of CSA-44 in bovine milk by HPLC with MS detection. The protocol has been designed to fulfill the requirements outlined in the FDA/CVM Guidance for Industry #208[1].

[1] Guidance for Industry #208: Studies to Evaluate the Metabolism and Residue Kinetics of Veterinary Drugs in Food-Producing Animals: Validation of Analytical Methods used in Residue Depletion Studies. VICH GL49. U.S. Department of Health and Human Services, Food and Drug Administration, Center for Veterinary Medicine. Sep. 15, 2011

A GLP-compliant total residue study was conducted in 3 healthy, lactating Holstein cows. Cows tested were in the middle of their 2nd or 3rd lactation. The more specific objective was to evaluate the safety of intramammary infusion of 120, 150 and 200 mg dosages of CSA-44 hydrochloride sterile saline (0.9% NaCl) suspension, respectively, in each of two front quarters daily for three consecutive days with an approximate 24-hour interval between infusions.

Three lactating female Holstein dairy cattle ranging from 2 to 5 years of age and representing low milk producers (13.2 kg to 24.0 kg/day) and high milk producers (25.0 kg to 31.9 kg/day) were used in the study. Cows were enrolled based on the absence of mastitis pathogens, absence of clinical mastitis (normal strip cup and udder palpation), a somatic cell count (SCC) less than or equal to 200,000 per mL, and no edema or teat lesions.

Within each lactation/production subgroup (1st lactation high producers, 1st lactation low producers, ≥2nd lactation high producers, and ≥2nd lactation low producers), cows were assigned to receive one of the three doses of CSA-44 by intramammary infusion. Following a 3-day pre-treatment clinical observation and milk sample collection period, animals received their assigned treatment.

A CSA-44 sterile saline suspension (120 mg, 150 mg or 200 mg) was administered as an intramammary infusion into both front quarters once at a 24-hour interval for three consecutive days.

Sterile milk samples were collected prior to administration of CSA-44, prior to each subsequent CSA-44 treatment, and prior to each milking for the next 60 hours for a total of either 14 milkings.

CSA-44, the reference standard, was supplied by the CSA Biotechnologies, LLC, located in Spanish Fork, Utah, USA (Sponsor). The chemical purity and batch number were included in the method validation report. The deuterated internal standard (ISTD), CSA-44 D2, was supplied by the Sponsor. The control sample matrix, raw bovine milk, was supplied by the Sponsor. The source of the milk was provided in the method validation report.

During method development, the estimated limit of detection (LOD) was determined to be 7.8 ng/mL, the estimated limit of quantitation (LOQ) was determined to be 15.6 ng/mL, and the upper limit of quantitation was determined to be 1,000 ng/mL.

The following schema (validation design) was used to determine specificity, LOD, LOQ, precision, accuracy, selectivity, and linearity:

| Fortification Concentration | Animal/Source ID† | | |
|---|---|---|---|
| | Day/Run 1 | Day/Run 2 | Day/Run 3 |
| 0 (Control) | B, F, D | A, C, C | B, E, F |
| eLOD* | B, C, E | D, F, F | A, B, E |
| eLOQ (3 X eLOD)* | C, C, E | A, B, E | D, F, D |
| Lower part of Validation Range | A, B, E | A, C, D | B, E, F |
| Middle of Validation Range | B, C, E | C, E, F | A, D, F |
| Upper Part of Validation Range | A, B, B | D, F, F | A, C, E |

*eLOD (estimated LOD) and eLOQ (estimated LOQ) is determined from preliminary studies conducted during method development.
†Source is identified by the letters A through F. Each source randomly selected such that each source is represented at least once at each concentration across the 3 validation runs In this design, drug-free matrix was collected from 6 separate sources (animals) and screened for any possible analyte contamination. On each of three days, samples were spiked according to the table above and analyzed along with a calibration curve on each day. In addition, the following Stability evaluations were performed:

Stability in Matrix.

Drug-free matrix was fortified with known quantities of analyte and stored under the appropriate conditions. These samples were periodically assayed at specified intervals (e.g. initially, 1 week, 1 month, 3 months). If the samples were frozen, freeze/thaw studies were conducted (3 freeze/thaw cycles—one cycle per day at a minimum). The recommended protocol for assessing stability in matrix is the analysis of two different concentrations in triplicate near the high and low end of the validation range.

Processed Sample Stability.

Often, the samples are processed one day and assayed on a second day or because of an instrument failure are stored additional days, e.g. over a weekend. The stability of the analyte in the process sample extract might be examined as necessary to determine stability under processed sample storage conditions. Examples of storage conditions would be 4 to 24 hours at room temperature and 48 hours at 4° C. Other storage conditions might be investigated consistent with the method requirements. The recommended protocol for assessing processed sample stability is the analysis of two different concentrations in triplicate near the high and low end of the validation range. Processed sample stability is considered adequate if the mean concentration obtained at the specified stability time point agrees with the initial assay results or with freshly fortified and processed control sample assay results within the established acceptance criteria.

The results from the 3 runs used to determine LOD, LOQ, linearity, intra- and inter-day precision and accuracy, and selectivity are considered acceptable if the intra- and inter-day precision and accuracy are within ±15% of nominal (±20% at the LOQ). The drug was considered stable if the results of the evaluations performed were within ±15% of nominal.

It is predicted that the study will show that CSA-44 will be undetectable in milk within 60-72 hours, and that residues of CSA-44 in the milk will be substantially depleted within 24-48 hours.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for treating or preventing clinical mastitis in a mammal, comprising:
administering an effective amount of a cationic steroidal anti-microbial compound (CSA) formulation that is effective in treating or preventing clinical mastitis caused by one or more different microbes, including at least clinical mastitis caused by *Prototheca*, to the intramammary organ of a mammal, the CSA formulation containing at least one CSA compound of Formula I, or a pharmaceutically acceptable salt thereof:

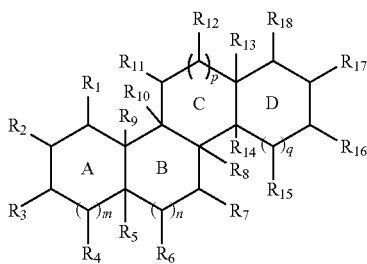

(I)

wherein
rings A, B, C, and D are independently saturated;
m, n, p, and q are independently 0 or 1;
$R_1$, $R_2$, $R_4$, $R_5$, $R_6$, $R_8$, $R_9$, $R_{10}$, $R_{11}$, $R_{13}$, $R_{14}$, $R_{15}$, $R_{16}$, and $R_{17}$ are independently selected from the group consisting of hydrogen and substituted or unsubstituted ($C_1$-$C_6$) alkyl;
$R_3$, $R_7$, $R_{12}$, and $R_{18}$ are independently selected from the group consisting of hydrogen, substituted or unsubstituted ($C_1$-$C_{18}$) alkyl, substituted or unsubstituted ($C_1$-$C_{18}$) hydroxyalkyl, substituted or unsubstituted ($C_1$-$C_{18}$) alkyloxy-($C_1$-$C_{18}$) alkyl, substituted or unsubstituted ($C_1$-$C_{18}$) alkylcarboxy-($C_1$-$C_{18}$) alkyl, substituted or unsubstituted ($C_1$-$C_{18}$) alkylamino-($C_1$-$C_{18}$) alkyl, substituted or unsubstituted ($C_1$-$C_{18}$) alkylamino-($C_1$-$C_{18}$) alkylamino, substituted or unsubstituted ($C_1$-$C_{18}$) alkylamino-($C_1$-$C_{18}$) alkylamino-($C_1$-$C_{18}$) alkylamino, substituted or unsubstituted ($C_1$-$C_{18}$) aminoalkyl, substituted or unsubstituted aryl, substituted or unsubstituted arylamino-($C_1$-$C_{18}$) alkyl, substituted or unsubstituted ($C_1$-$C_{18}$) haloalkyl, substituted or unsubstituted ($C_2$-$C_6$) alkenyl, substituted or unsubstituted ($C_2$-$C_6$) alkynyl, oxo, substituted or unsubstituted ($C_1$-$C_{18}$) aminoalkyloxy, substituted or unsubstituted ($C_1$-$C_{18}$) aminoalkyloxy-($C_1$-$C_{18}$) alkyl, substituted or unsubstituted ($C_1$-$C_{18}$) aminoalkylcarboxy, substituted or unsubstituted ($C_1$-$C_{18}$) aminoalkylaminocarbonyl, substituted or unsubstituted ($C_1$-$C_{18}$) aminoalkylcarboxamido, substituted or unsubstituted di($C_1$-$C_{18}$ alkyl)aminoalkyl, substituted or unsubstituted C-carboxy($C_1$-$C_{18}$) alkyl, $H_2N$—$HC(Q_5)$-$C(O)$—$O$—, $H_2N$—$HC(Q_5)$-$C(O)$—$N(H)$—, substituted or unsubstituted ($C_1$-$C_{18}$) azidoalkyloxy, substituted or unsubstituted ($C_1$-$C_{18}$) cyanoalkyloxy, substituted or unsubstituted ($C_1$-$C_{18}$) guanidinoalkyloxy, substituted or unsubstituted ($C_1$-$C_{18}$) quaternary ammonium alkylcarboxy, and substituted or unsubstituted ($C_1$-$C_{18}$) guanidinoalkyl carboxy, where $Q_5$ is a side chain of an amino acid;
provided that at least two of $R_3$, $R_7$, $R_{12}$ and $R_{18}$ are independently selected from the group consisting of aminoalkyloxy, aminoalkylcarboxy, alkylaminoalkyl, and di(alkyl)aminoalkyl.

2. The method of claim 1, wherein the CSA formulation is administered by at least one of injection into the mammary organ or injection through the teat of the mammary organ.

3. The method of claim 1, wherein the mammal is a dairy cow.

4. The method of claim 3, wherein the dairy cow is lactating and has a somatic cell count (SCC) greater than 500,000 cells/mL at the time of administering the CSA.

5. The method of claim 4, the method comprising taking the dairy cow out of production for a period of time of 3 days or less while administering the CSA formulation.

6. The method of claim 1, wherein the at least one CSA compound comprises a compound of Formula (IA), or a pharmaceutically acceptable salt thereof:

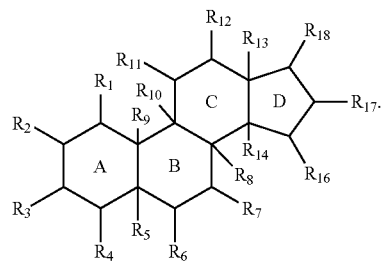

(IA)

7. The method of claim 1, wherein $R_3$, $R_7$, $R_{12}$, and $R_{18}$ are independently selected from the group consisting of hydrogen, an unsubstituted ($C_1$-$C_6$) alkyl, unsubstituted ($C_1$-$C_6$) hydroxyalkyl, unsubstituted ($C_1$-$C_{16}$) alkyloxy-($C_1$-$C_5$) alkyl, unsubstituted ($C_1$-$C_{16}$) alkylcarboxy-($C_1$-$C_5$) alkyl, unsubstituted ($C_1$-$C_{16}$) alkylamino-($C_1$-$C_5$)alkyl, ($C_1$-$C_{16}$) alkylamino-($C_1$-$C_5$) alkylamino, unsubstituted ($C_1$-$C_{16}$) alkylamino-($C_1$-$C_{16}$) alkylamino-($C_1$-$C_5$) alkylamino, an unsubstituted ($C_1$-$C_{16}$) aminoalkyl, an unsubstituted arylamino-($C_1$-$C_5$) alkyl, an unsubstituted ($C_1$-$C_5$) aminoalkyloxy, an unsubstituted ($C_1$-$C_{16}$) aminoalkyloxy-($C_1$-$C_5$) alkyl, an unsubstituted ($C_1$-$C_5$) aminoalkylcarboxy, an unsubstituted ($C_1$-$C_5$) aminoalkylaminocarbonyl, an unsubstituted ($C_1$-$C_5$) aminoalkylcarboxamido, an unsubstituted di($C_1$-$C_5$ alkyl)amino-($C_1$-$C_5$) alkyl, unsubstituted C-carboxy($C_1$-$C_{18}$)alkyl, unsubstituted ($C_1$-$C_5$) guanidinoalkyloxy, unsubstituted ($C_1$-$C_{16}$) quaternary ammonium alkylcarboxy, and unsubstituted ($C_1$-$C_{16}$) guanidinoalkylcarboxy, provided that at least two of $R_3$, $R_7$, or $R_{12}$ include a cationic moiety attached to the sterol backbone via a hydrolysable linkage and $R_{18}$ is selected from the group consisting of aminoalkyloxy, aminoalkylcarboxy, alkylaminoalkyl, di(alkyl)aminoalkyl, alkoxycarbonylalkyl, alkylcarbonyloxyalkyl, C-carboxyalkyl, alkylaminoalkyl, alkyoxycarbonylalkyl, and alkylcarboxyalkyl.

8. The method of claim 1, wherein $R_1$, $R_2$, $R_4$, $R_5$, $R_6$, $R_8$, $R_{10}$, $R_{11}$, $R_{14}$, $R_{16}$, and $R_{17}$ are each hydrogen; and $R_9$ and $R_{13}$ are each methyl.

9. The method of claim 1, wherein $R_3$, $R_7$, $R_{12}$, and $R_{18}$ are independently selected from the group consisting of aminoalkyloxy; aminoalkylcarboxy; alkylaminoalkyl; alkoxycarbonylalkyl; alkylcarbonylalkyl; di(alkyl)aminoalkyl; C-carboxyalkyl; alkoxycarbonylalkyl; and alkylcarboxyalkyl.

10. The method of claim 1, wherein
R$_3$, R$_7$, and R$_{12}$ are independently selected from the group consisting of aminoalkyloxy and aminoalkylcarboxy; and
R$_{18}$ is selected from the group consisting of alkylaminoalkyl; alkoxycarbonylalkyl; alkylcarbonyloxyalkyl; di(alkyl)aminoalkyl; C-carboxyalkyl; alkylaminoalkyl; alkyoxycarbonylalkyl; and alkylcarboxyalkyl.

11. The method of claim 1, wherein R$_3$, R$_7$, and R$_{12}$ are the same.

12. The method of claim 1, wherein R$_3$, R$_7$, and R$_{12}$ are each aminoalkylcarboxy.

13. The method of claim 12, wherein R$_{18}$ is alkylcarboxyalkyl.

14. The method of claim 12, wherein R$_3$, R$_7$, and R$_{12}$ are amino-C$_3$-alkyl-carboxy and R$_{18}$ is selected from the group consisting of C$_8$-alkoxy-carbonyl-C$_4$-alkyl; C-carboxy-C$_4$-alkyl; C$_6$-alkoxy-carbonyl-C$_4$-alkyl; and C$_6$-alkyl-carboxy-C$_4$-alkyl.

15. The method of claim 1, wherein the at least one CSA compound comprises a compound of Formula (IB), or a pharmaceutically acceptable salt thereof:

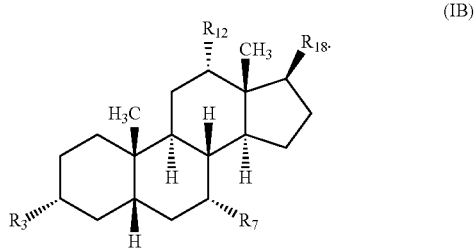

(IB)

16. The method of claim 15, wherein the compound of Formula (IB) is selected from the group of:

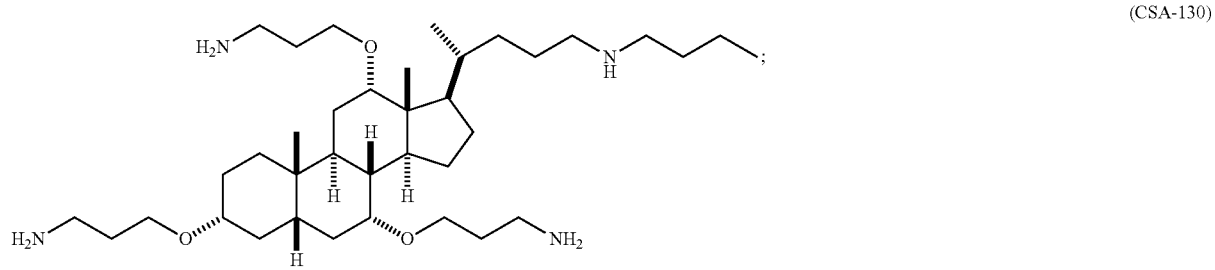

(CSA-130)

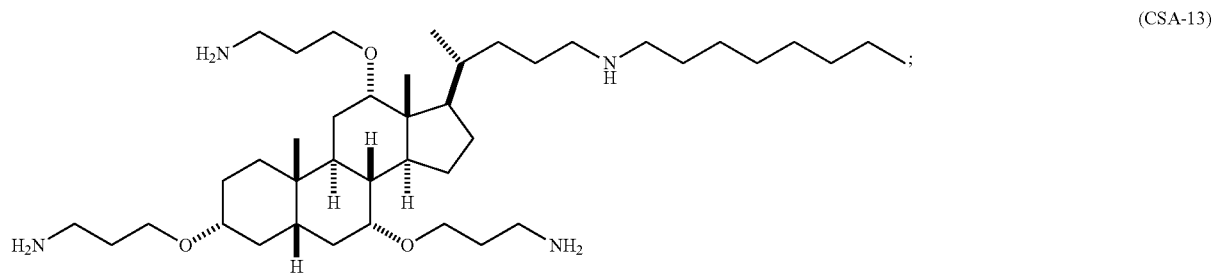

(CSA-13)

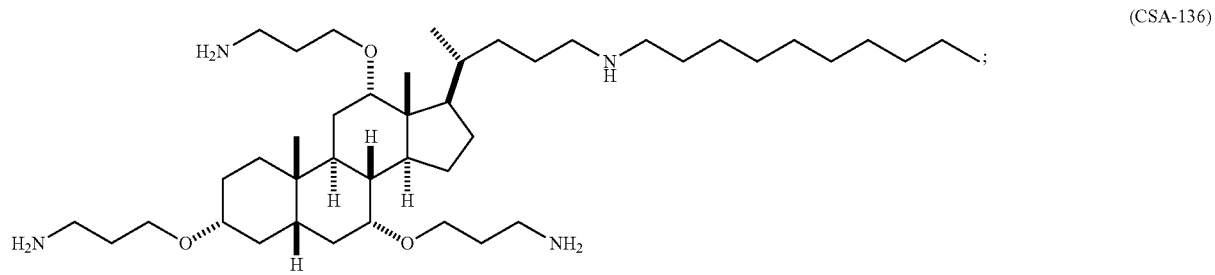

(CSA-136)

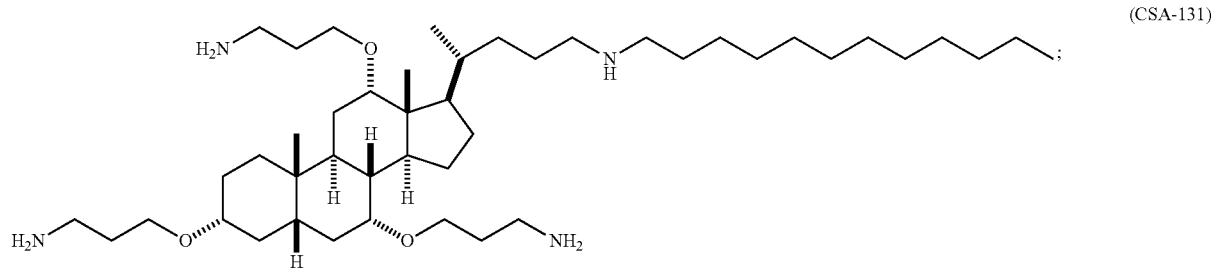

(CSA-131)

-continued
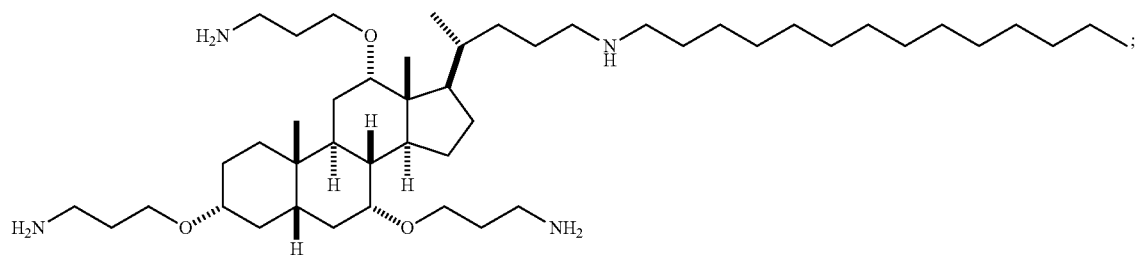
(CSA-134)
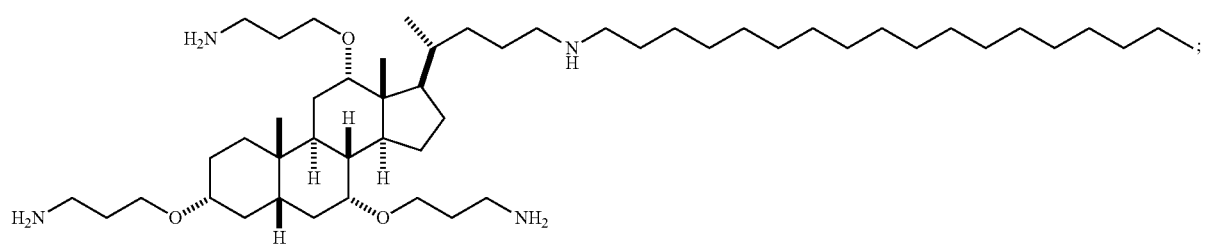
(CSA-132)
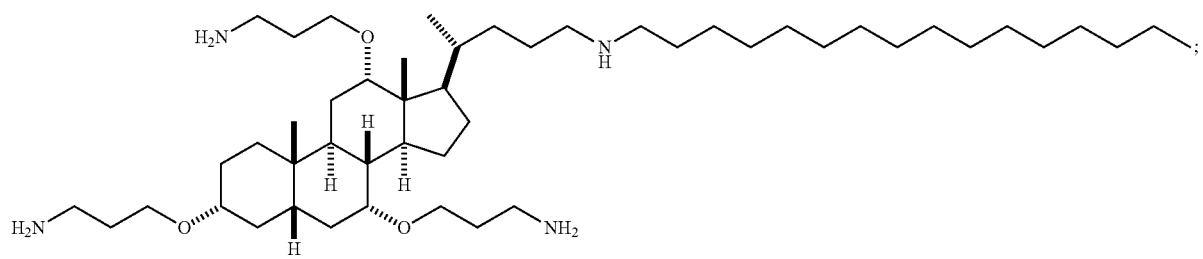
(CSA-135)
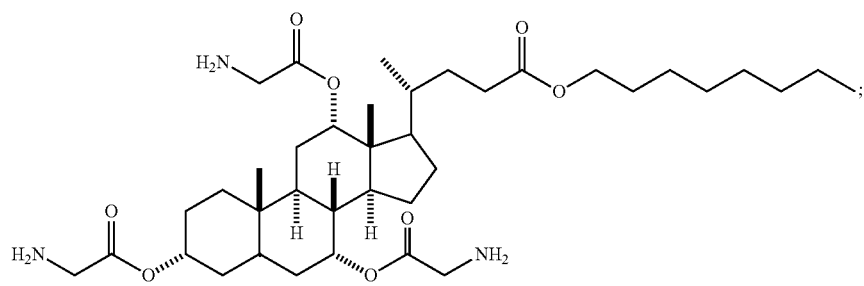
(CSA-43)
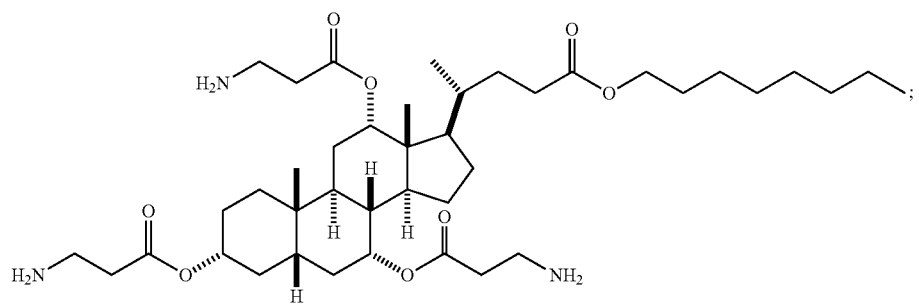
(CSA-44)

-continued
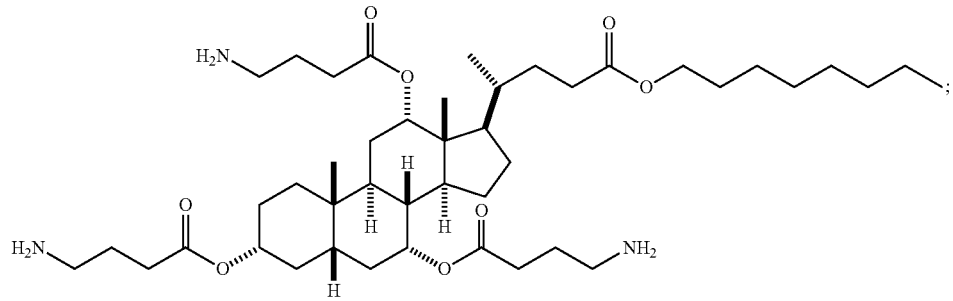
(CSA-45)
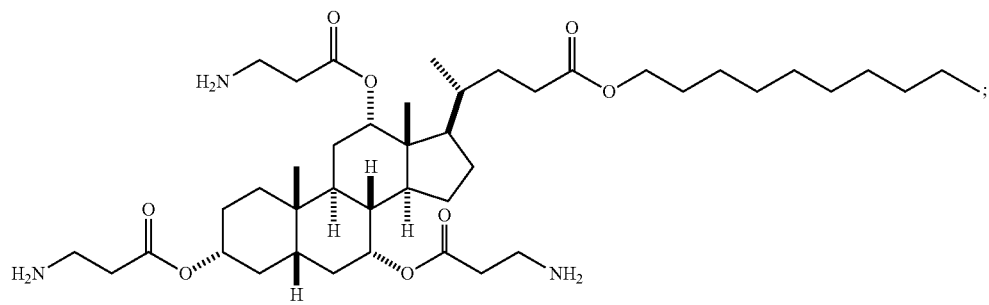
(CSA-144)
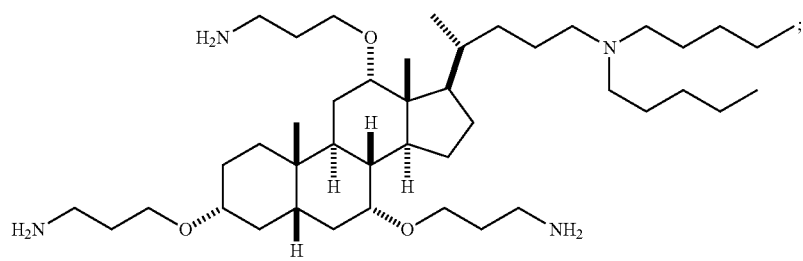
(CSA-90)
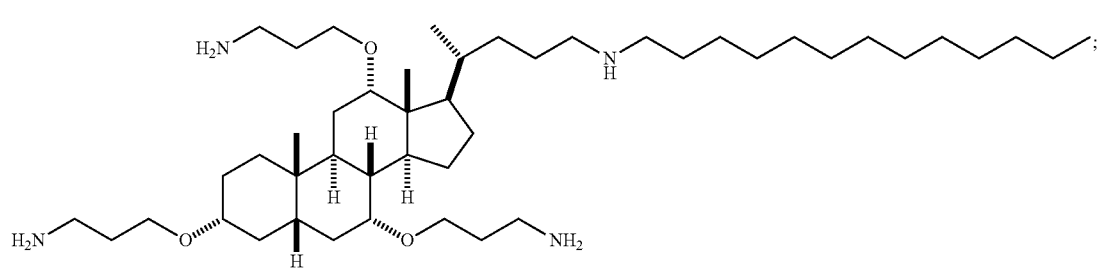
(CSA-138)
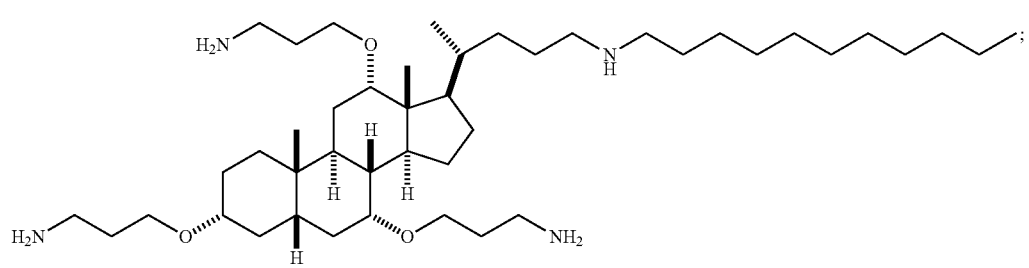
(CSA-137)

-continued

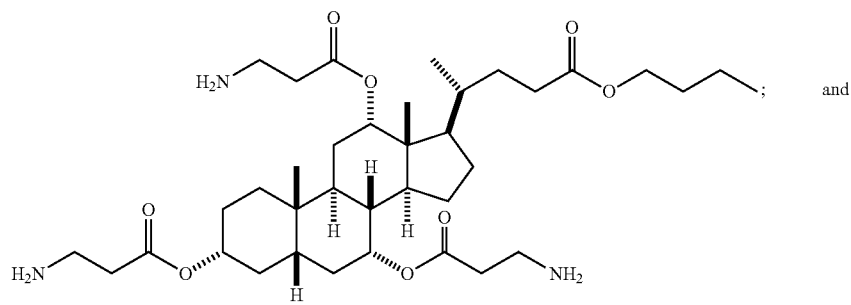
(CSA-141)
and

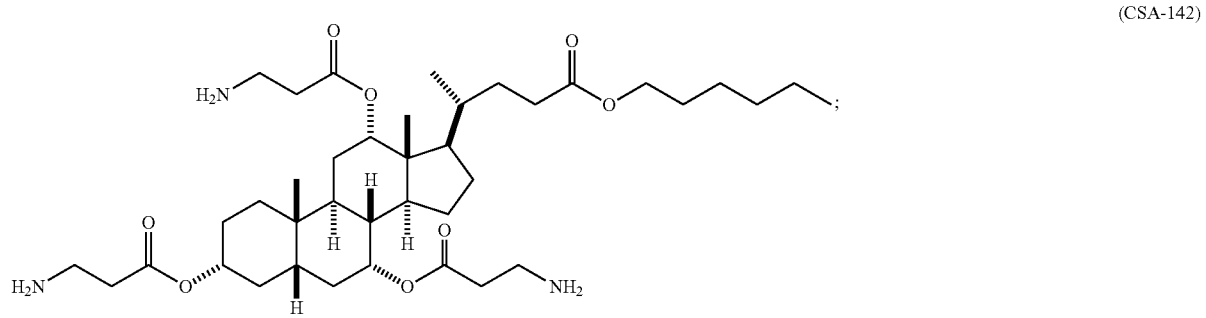
(CSA-142)

17. The method of claim 15, wherein the compound of Formula (IB) is selected from:

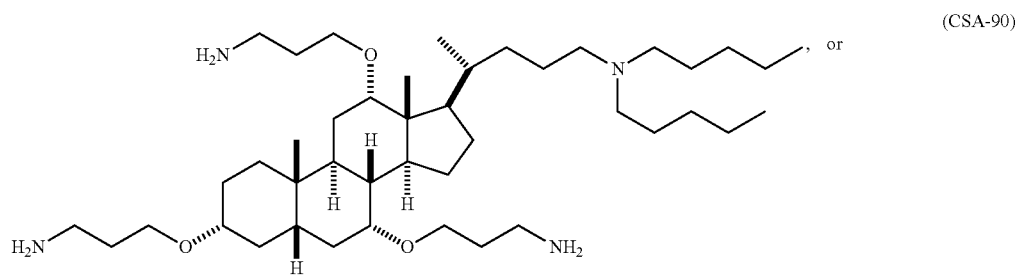
(CSA-90)
or

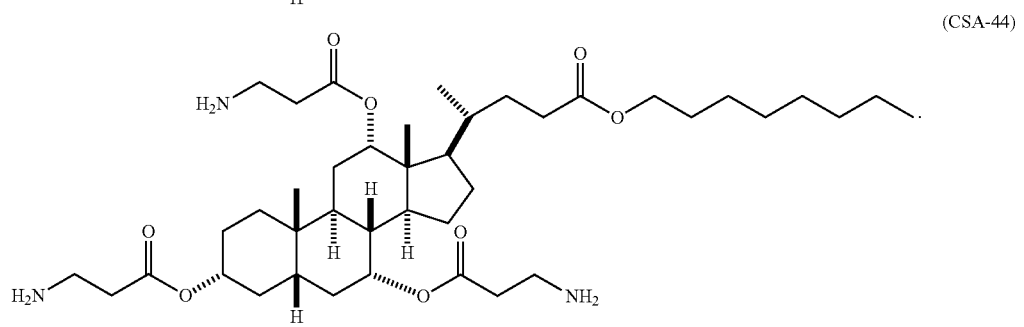
(CSA-44)

18. The method of claim 1, wherein the pharmaceutically acceptable salt is a hydrochloride salt or a tri-hydrochloride salt.

19. A method for treating or preventing clinical mastitis in a lactating dairy cow, comprising:
   injecting an effective amount of a cationic steroidal antimicrobial compound (CSA) formulation that is effective in treating or preventing clinical mastitis caused by one or more different microbes, including at least clinical mastitis caused by *Prototheca* to an intra-mammary organ of the lactating dairy cow, the CSA formulation containing at least one CSA compound of Formula I, or a pharmaceutically acceptable salt thereof:

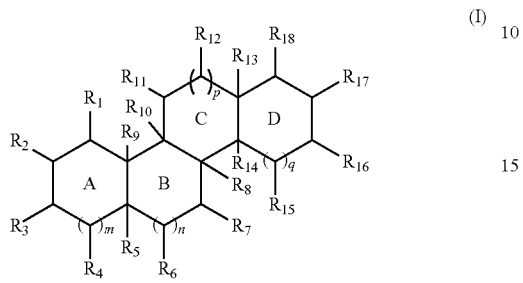

wherein
rings A, B, C, and D are independently saturated;
m, n, p, and q are independently 0 or 1;
$R_1, R_2, R_4, R_5, R_6, R_8, R_9, R_{10}, R_{11}, R_{13}, R_{14}, R_{15}, R_{16}$, and $R_{17}$ are independently selected from the group consisting of hydrogen and substituted or unsubstituted ($C_1$-$C_6$) alkyl;
$R_3, R_7, R_{12}$, and $R_{18}$ are independently selected from the group consisting of hydrogen, hydroxyl, substituted or unsubstituted ($C_1$-$C_{18}$) alkyl, substituted or unsubstituted ($C_1$-$C_{18}$) hydroxyalkyl, substituted or unsubstituted ($C_1$-$C_{18}$) alkyloxy-($C_1$-$C_{18}$) alkyl, substituted or unsubstituted ($C_1$-$C_{18}$) alkylcarboxy-($C_1$-$C_{18}$) alkyl, substituted or unsubstituted ($C_1$-$C_{18}$) alkylamino-($C_1$-$C_{18}$) alkyl, substituted or unsubstituted ($C_1$-$C_{18}$) alkylamino-($C_1$-$C_{18}$) alkylamino, substituted or unsubstituted ($C_1$-$C_{18}$) alkylamino-($C_1$-$C_{18}$) alkylamino-($C_1$-$C_{18}$) alkylamino, substituted or unsubstituted ($C_1$-$C_{18}$) aminoalkyl, substituted or unsubstituted aryl, substituted or unsubstituted arylamino-($C_1$-$C_{18}$) alkyl, substituted or unsubstituted ($C_1$-$C_{18}$) haloalkyl, substituted or unsubstituted ($C_2$-$C_6$) alkenyl, substituted or unsubstituted ($C_2$-$C_6$) alkynyl, oxo, substituted or unsubstituted ($C_1$-$C_{18}$) aminoalkyloxy, substituted or unsubstituted ($C_1$-$C_{18}$) aminoalkyloxy-($C_1$-$C_{18}$) alkyl, substituted or unsubstituted ($C_1$-$C_{18}$) aminoalkylcarboxy, substituted or unsubstituted ($C_1$-$C_{18}$) aminoalkylaminocarbonyl, substituted or unsubstituted ($C_1$-$C_{18}$) aminoalkylcarboxamido, substituted or unsubstituted di($C_1$-$C_{18}$ alkyl) aminoalkyl, substituted or unsubstituted C-carboxy($C_1$-$C_{18}$) alkyl, $H_2N$—$HC(Q_5)$-$C(O)$—$O$—, $H_2N$—$HC(Q_5)$-$C(O)$—$N(H)$—, substituted or unsubstituted ($C_1$-$C_{18}$) azidoalkyloxy, substituted or unsubstituted ($C_1$-$C_{18}$) cyanoalkyloxy, substituted or unsubstituted ($C_1$-$C_{18}$) guanidinoalkyloxy, substituted or unsubstituted ($C_1$-$C_{18}$) quaternary ammonium alkylcarboxy, and substituted or unsubstituted ($C_1$-$C_{18}$) guanidinoalkyl carboxy, where $Q_5$ is a side chain of an amino acid;
provided that at least two of $R_3, R_7, R_{12}$ and $R_{18}$ are independently selected from the group consisting of aminoalkyloxy, aminoalkylcarboxy, alkylaminoalkyl, and di(alkyl)aminoalkyl.

20. A method for treating or preventing clinical mastitis in a lactating dairy cow, comprising:
injecting an effective amount of a cationic steroidal antimicrobial compound (CSA) formulation that is effective in treating or preventing clinical mastitis caused by one or more different microbes, including at least clinical mastitis caused by *Prototheca*, to an intra-mammary organ of the lactating dairy cow,
wherein the CSA formulation comprises a compound having a sterol backbone of Formula (TB) or a pharmaceutically acceptable salt thereof:

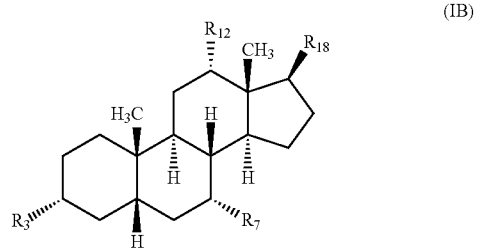

where,
$R_3, R_7$, and $R_{12}$ each include a cationic moiety attached to the sterol backbone via a hydrolysable linkage and $R_{18}$ is selected from the group consisting of hydrogen, hydroxyl, substituted or unsubstituted ($C_1$-$C_{18}$) alkyl, substituted or unsubstituted ($C_1$-$C_{18}$) hydroxyalkyl, substituted or unsubstituted ($C_1$-$C_{18}$) alkyloxy-($C_1$-$C_{18}$) alkyl, substituted or unsubstituted ($C_1$-$C_{18}$) alkylcarboxy-($C_1$-$C_{18}$) alkyl, substituted or unsubstituted ($C_1$-$C_{18}$) alkylamino-($C_1$-$C_{18}$) alkyl, substituted or unsubstituted ($C_1$-$C_{18}$) alkylamino-($C_1$-$C_{18}$) alkylamino, substituted or unsubstituted ($C_1$-$C_{18}$) alkylamino-($C_1$-$C_{18}$) alkylamino-($C_1$-$C_{18}$) alkylamino, substituted or unsubstituted ($C_1$-$C_{18}$) aminoalkyl, substituted or unsubstituted aryl, substituted or unsubstituted arylamino-($C_1$-$C_{18}$) alkyl, substituted or unsubstituted ($C_1$-$C_{18}$) haloalkyl, substituted or unsubstituted ($C_2$-$C_6$) alkenyl, substituted or unsubstituted ($C_2$-$C_6$) alkynyl, oxo, substituted or unsubstituted ($C_1$-$C_{18}$) aminoalkyloxy, substituted or unsubstituted ($C_1$-$C_{18}$) aminoalkyloxy-($C_1$-$C_{18}$) alkyl, substituted or unsubstituted ($C_1$-$C_{18}$) aminoalkylcarboxy, substituted or unsubstituted ($C_1$-$C_{18}$) aminoalkylaminocarbonyl, substituted or unsubstituted ($C_1$-$C_{18}$) aminoalkylcarboxamido, substituted or unsubstituted di($C_1$-$C_{18}$ alkyl) aminoalkyl, substituted or unsubstituted C-carboxy($C_1$-$C_{18}$) alkyl, $H_2N$—$HC(Q_5)$-$C(O)$—$O$—, $H_2N$—$HC(Q_5)$-$C(O)$—$N(H)$—, substituted or unsubstituted ($C_1$-$C_{18}$) azidoalkyloxy, substituted or unsubstituted ($C_1$-$C_{18}$) cyanoalkyloxy, substituted or unsubstituted ($C_1$-$C_{18}$) guanidinoalkyloxy, substituted or unsubstituted ($C_1$-$C_{18}$) quaternary ammonium alkylcarboxy, and substituted or unsubstituted ($C_1$-$C_{18}$) guanidinoalkyl carboxy, where $Q_5$ is a side chain of an amino acid.

21. The method of claim 20, wherein the compound of Formula (IB) is selected from the group of:

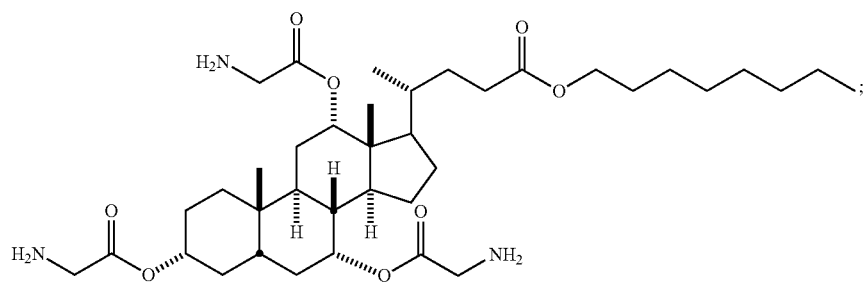
(CSA-43)
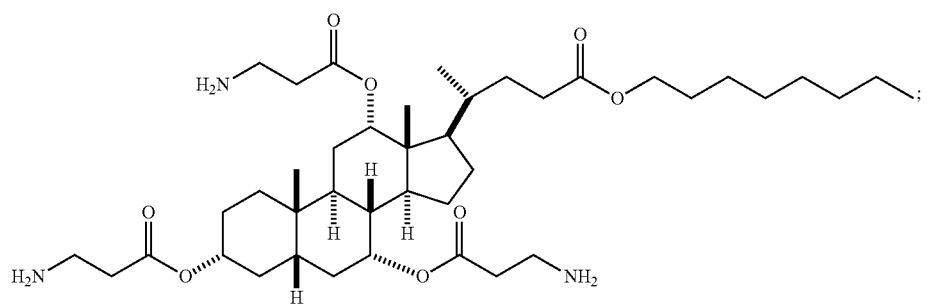
(CSA-44)
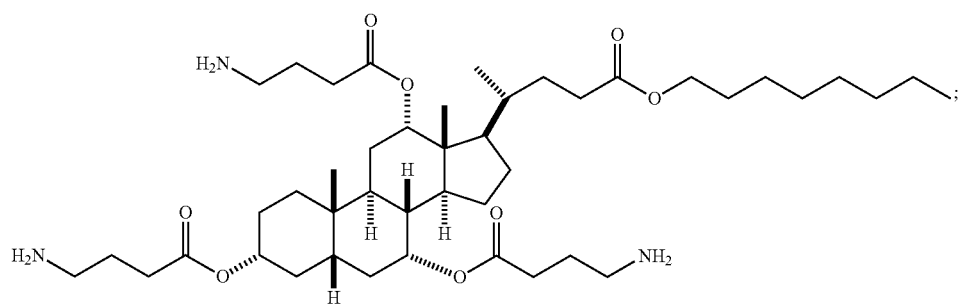
(CS-45)
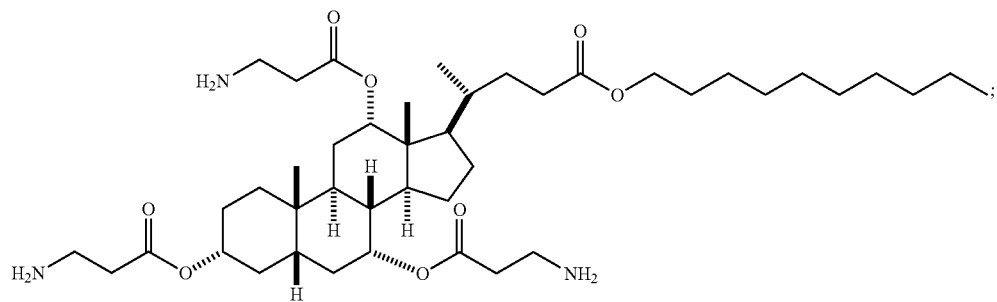
(CSA-144)
and
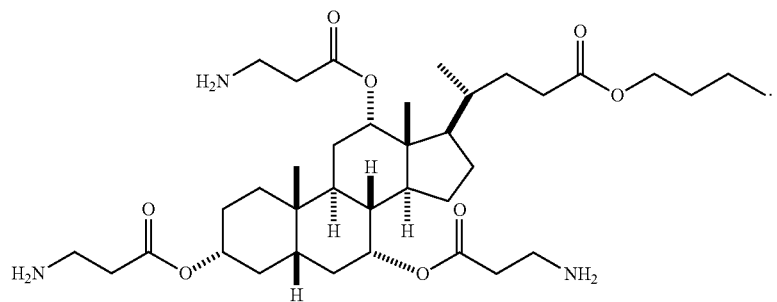
(CSA-141)

22. The method of claim 20, wherein the compound of Formula (IB) is selected from:
(CSA-142)
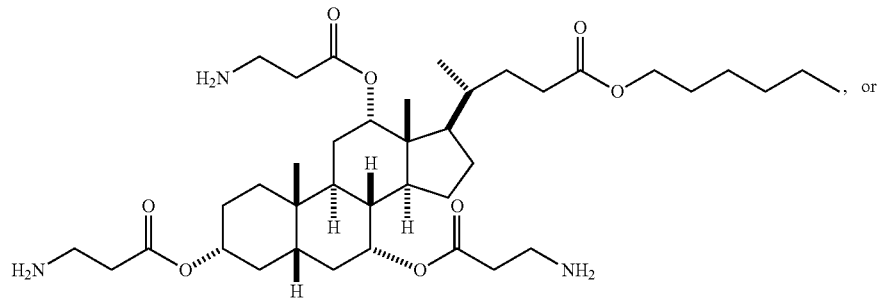
, or
(CSA-44)
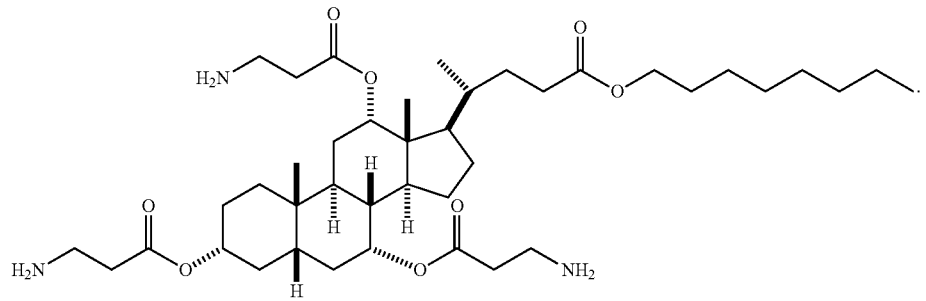
.
* * * * *